US008415480B2

(12) United States Patent
Page et al.

(10) Patent No.: US 8,415,480 B2

(45) Date of Patent: Apr. 9, 2013

(54) THIAZOLIDINE CARBOXAMIDE DERIVATIVES AS MODULATORS OF THE PROSTAGLANDIN F RECEPTOR

(75) Inventors: Patrick Naxos Page, Saint Julien-en Genevois (FR); Catherine Jorand-Lebrun, Contamine-Sarzin (FR); Anna Quattropani, Geneva (CH); Vincent Pomel, Groisy (FR); Matthias Schwarz, Geneva (CH); Estelle Hamelin, Oxon (GB); Russell J. Thomas, Siena (IT)

(73) Assignee: Merck Serono SA, Coinsins (CH)

( * ) Notice: Subject to any disclaimer, the term of this patent is extended or adjusted under 35 U.S.C. 154(b) by 625 days.

(21) Appl. No.: 12/140,682

(22) Filed: Jun. 17, 2008

(65) Prior Publication Data

US 2009/0215749 A9 Aug. 27, 2009

Related U.S. Application Data

(62) Division of application No. 10/508,014, filed as application No. PCT/EP03/50083 on Mar. 27, 2003, now abandoned.

(30) Foreign Application Priority Data

Mar. 28, 2002 (EP) .................................... 02100314

(51) Int. Cl.

| | |
|---|---|
| ***A61K 31/4402*** | (2006.01) |
| ***A61K 31/426*** | (2006.01) |
| ***C07D 417/12*** | (2006.01) |
| ***C07D 277/46*** | (2006.01) |

(52) U.S. Cl.

USPC ........ 548/200; 514/365; 514/342; 546/269.7; 548/181

(58) Field of Classification Search ................... 548/200

See application file for complete search history.

(56) References Cited

U.S. PATENT DOCUMENTS

| | | | | |
|---|---|---|---|---|
| 4,016,270 | A * | 4/1977 | Pharriss et al. | 514/174 |
| 4,904,680 | A | 2/1990 | Matsui et al. | |
| 5,338,755 | A | 8/1994 | Wagnon et al. | |
| 6,271,201 | B1 | 8/2001 | Siler-Khodr | |
| 6,645,939 | B1 | 11/2003 | Durette et al. | |
| 2005/0215605 | A1 | 9/2005 | Page et al. | |

FOREIGN PATENT DOCUMENTS

| | | | |
|---|---|---|---|
| JP | 64-50818 | | 2/1989 |
| WO | 98/08822 | | 3/1998 |
| WO | 99/06390 | | 2/1999 |
| WO | 03/082278 | A1 | 10/2003 |

OTHER PUBLICATIONS

J.A. Russell et al, "Sex, parturition and motherhood without oxytocin?", Journal of Endocrinology, vol. 157, pp. 343-359, 1998.

Yukihiko Sugimoto et al, "Failure of parturition in mice lacking the prostaglandin F receptor", Science, vol. 277, pp. 681-683, Aug. 1, 1997.

McCracken, The impact of population pressure on conservation and development, Research in Reproduction, vol. 16, pp. 102, 1984.

Amar Chatterjee, Prostaglandins, vol. 12, No. 6, pp. 1053-1059, 1976.

B. J. Williams et al, "Effect of sodium cloprostenol and flunixin meglumine on luteolysis and the time of birth in bitches", Journal of Reproduction and Fertility, vol. 116, No. 1, pp. 103-111, 1999.

Ricardo Mattos et al, "Effects of dietary fatty acids on reproduction in ruminants", Reviews of Reproduction, vol. 5, No. 1, pp. 38-45, 2000.

Yoko Takanami-Onishi et al, Possible involvement of p38 mitogen-activated protein kinase in decidual function in parturition, "Biochemical and Biophysical Research Communications", vol. 288, No. 5, pp. 1155-1161, 2001.

P. Schauer, et al., Caplus document 79:74124, "Antimicrobial activity of some derivatives of thiazolidine carbonic acid and some alkylidene and arylidene derivatives of 3-hydrazinopyridazines and 3-hydrazino-6-chloropyridazine 1-oxide", Advan. Antimicrob. Antineoplastic Chemother., Proc. Int. Congr. Chemother., $7^{th}$ (1972), Meeting Date 1971, vol. 1, Issue 1, 1973, p. 1.

* cited by examiner

*Primary Examiner* — Laura L. Stockton

(74) *Attorney, Agent, or Firm* — Oblon, Spivak, McClelland, Maier & Neustadt, L.L.P.

(57) ABSTRACT

The present invention is related to thiazolidine carboxamide derivatives of formula (II) for the treatment and/or prophylaxis of preterm labor, premature birth, dysmenorrhea and for stopping labor prior to cesarean delivery.

II

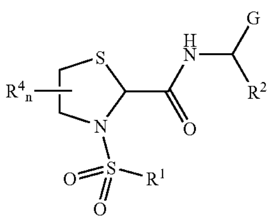

11 Claims, No Drawings

THIAZOLIDINE CARBOXAMIDE DERIVATIVES AS MODULATORS OF THE PROSTAGLANDIN F RECEPTOR

CROSS-REFEREMCE TO RELEATED APPLICATIONS

The present application is a divisional of U.S. Ser. No. 10/508,014, filed on May 12, 2005, which is a National State (371) of PCT/EP03/50083, filed on Mar. 27, 2003, which claims priority to EP 02100314.0, filed on Mar. 28, 2002.

FIELD OF THE INVENTION

This present invention is related to thiazolidine carboxamide derivatives of formula (II) for the treatment and/or prophylaxis of preterm labor, premature birth, dysmenorrhea and for stopping labor prior to cesarean delivery. Specifically, the present invention is related to substituted thiazolidine carboxamide derivatives for the modulation, notably the inhibition of the activity or function of the prostaglandin receptors, particularly of the prostaglandin $F_{2\alpha}$ receptor. Also, the present invention is related to novel thiazolidine carboxamide derivatives of formulae (I) and (Ia).

BACKGROUND OF THE INVENTION

In the field of obstetrics, one of the most important problems is the management of preterm labor and premature birth as they represent a major cause of perinatal morbidity and mortality.

In recent years, strong evidence has accumulated indicating that the hormone oxytocin plays a major role in initiating labor in mammals, notably in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process.

In parturition, the high circulating concentrations of progesterone induce uterine quiescence while the uterus acquires contractile ability. Shortly before term, plasma progesterone concentrations fall, oxytocin receptor expression in the uterus increases markedly, and uterine contractile activity increases. At term, the contractions rise to a crescendo, resulting in delivery as a result of two interacting positive feedback loop. The first is a local uterine loop: within the uterus itself, prostaglandins and other uterotonic factors are produced and released in response to uterine contractions. The second loop involves the hypothalamus: in response to uterine contractions and vaginal and cervical distension, magnocellular oxytocin neurons in the hypothalamus increase their activity resulting in the release of oxytocin from their axon terminals in the posterior pituitary; the released oxytocin acts upon the uterus both to stimulate the further production of prostaglandins and to contribute further to the contractions of the uterus. (*Journal of Endocrinology* 157, p. 343-359 (1998) by J. A Russell and al.).

For the treatment of preterm labor, several approaches have been considered such as the use of magnesium sulfate, ethanol or therapeutic agents acting as $\beta_2$ adrenergic agonists or oxytocin antagonists:

- With the use of magnesium sulfate, it has been observed that plasma concentrations above the therapeutic range of 4 to 8 mg/dL can cause inhibition of cardiac conduction and neuromuscular transmission, respiratory depression and cardiac arrest, thus making this agent unsuitable notably when the renal function is impaired.
- Ethanol is effective in preventing premature labor, but it does not produce a corresponding reduction in the incidence of fetal respiratory distress. Also, ethanol is assumed to have a negative impact on the fetus.
- The $\beta_2$-adrenergic receptor generally causes an inhibitory action within the cells wherein it is expressed (muscles, heart, uterus etc). $\beta_2$-adrenergic agonists are used to activate said inhibitory action of the receptor. Hence, $\beta_2$-adrenergic agonists are sympathomimetics which—among others—inhibit uterine contractility. Known $\beta_2$-adrenergic agonists for the treatment of preterm labor are Ritodrine, Terbutaline and Albuterol.
- Oxytocin antagonists: Oxytocin (OT) is a peptide hormone causing the contraction of the uterus of mammals during labor. Oxytocin (OT) receptors increase dramatically during the course of pregnancy. The concentration of OT receptors has been shown to correlate with spontaneous uterine activity. In the last few years, a number of papers have suggested that the hormone oxytocin may be a physiological initiator of labor in several mammalian species including humans. Furthermore, oxytocin is believed to exert this effect in two different parts, either by directly contracting the uterine myometrium and by enhancing the synthesis and release of contractile prostaglandins from the uterine endometrium/decidua. Therefore, by blocking oxytocin, the direct (contractile) and indirect (enhanced prostaglandin synthesis) effects of oxytocin on the uterus may be achieved.

Prostaglandins (PGs), more particularly prostaglandin $F_{2\alpha}$ ($PGF_{2\alpha}$), play a key role in the normal physiology of several tissues including ovary, oviduct, uterus, testis, lung and possibly eye and heart and is implicated in reproductive functions such as ovulation, luteolysis and parturition. It is well known that parturition is initiated when prostaglandin $F_{2\alpha}$ interacts with FP (Prostaglandin F receptor) in ovarian luteal cells of the pregnant mice to induce luteolysis. (*Science* vol. 277 p. 681-687 (1997) by Yuhihiko Sugimoto et al). Actions of $PGF_{2\alpha}$ are mediated by the PGF receptor (FP), which is a heterotrimeric guanosine triphosphate—binding protein (G protein)—coupled rhodopsin type receptor specific to this PG (*Science* vol. 277, p. 681-83 (1998) by Yuhihiko Sugimoto et al.). These prostaglandins belong to a group of eicosanoids that are produced by the enzymatic activity of cyclooxygenase. Together with the thromboxanes, prostaglandins constitute the prostanoid subgroup of the eicosanoids. Prostaglandins (PGs) mediate various physiological processes such as fever generation and inflammation. Aspirin and related drugs act through inhibition of PG biosynthesis.

$PGF_{2\alpha}$ is synthesized, to varying degrees, by almost every tissue in the body and is a stimulant of several different types of physiological functions including granulose lutein cell death, myometrial smooth muscle contraction, Leydig cell testosterone synthesis regulation, regulation of oviductal cilia beating, bronchoconstriction, and bone metabolism. They are synthesized in fetal and maternal membranes and act to ripen the cervix and contract the myometrium. $PGF_{2\alpha}$ is a major prostaglandin for enhancing uterine contractility.

Specific prostaglandin receptors ($EP_1$, $EP_2$, $EP_4$ and FP) are expressed in the human myometrium. Activation of $EP_2$ and $EP_4$ receptors results in smooth muscle relaxation whereas activation of the $PGF_{2\alpha}$-selective receptor (FP receptor) results in contraction. Indeed, the prostaglandin $F_{2\alpha}$ receptor acts via a G protein-coupled receptor, coupled to activation of phospholipase C and increases in $IP_3$ that release $Ca^{2+}$ from intracellular stores. The increases in intracellular calcium that ensue lead to increased contraction of smooth muscle via activation of myosin light chain kinase. Also, it is known that mice lacking the FP receptor have normal fertility but no labor at term. However healthy pups were delivered by cesarean cut. One of the most important roles of $PGF_{2\alpha}$ is in reproductive biology as a luteolytic agent. In the non-pregnant state, at the end of the luteal phase, increased pulsatile serum levels of $PGF_{2\alpha}$(of uterine origin) cause apoptotic cell death of the granulosam lutein cells (*Res. Reprod.* 16:1-2 (1984) by McCracken).

There is recent evidence for up-regulation of the contractile FP receptor with the onset and during progression of labor. Also, recent reports indicate that oxytocin induces production of PGs in human myometrial cells via upregulation of COX-2. Such a mechanism may explain the sustained release of PGs in uterine tissue, promoting labor. Therefore, there is strong evidence that interfering with the prostaglandin pathway by blocking selectively the contractile FP receptor will delay the progression of labor. A compound able to block the interaction between $PGF_{2\alpha}$ and its receptor, i.e. a $PGF_{2\alpha}$-receptor antagonist, is therefore assumed to be more efficacious for treating preterm labor than current regimens.

Because of the involvement of $PGF_{2\alpha}$ in birth initiation, several approaches have already been performed to test new $PGF_{2\alpha}$ inhibitors. Indomethacin is a well known prostaglandin inhibitor and has already been tested to study the possible mode of action of prostaglandins (*Prostaglandins,* 12(6) p. 1053-9 (1976) by Chatterjee A.). In *J. Reprod. Fertil.,* 116(1), p. 103-111 (1999) Williams B. J. et al observed that flunixin meglumine disrupted the normal 13,14-dihydro-15-keto prostaglandin $F_{2\alpha}$ profile but did not abolish prostaglandin synthesis completely or delay the onset of labor in treated animals. Mattos R. et al (*Rev. Reprod.,* 5(1), p. 38-45 (2000) use polyunsaturated fatty acids such as linoleic, linolenic, eicosapentaenoic and docosahexaenoic acids which may inhibit prostaglandin $F_{2\alpha}$.

Recently, a phenol derivative known as p38 inhibitor (4-[5-(4-fluorophenyl)-4-(4-pyridyl)-imidazol-2-yl]phenol) has been tested and it has been observed that said compound inhibited both prostaglandin $F_{2\alpha}$ production and COX-2 expression induced by stimulation with IL-1β(*Biochem. Biophys. Res. Commun.,* 288(5), p. 1155-1161 (2001) by Chuoku Chiba).

Tsumura & Co proposed prostaglandin $F_{2\alpha}$ inhibitor active to relax the smooth muscle of uterine and effective for the remedy of abdominal pain caused by abortion, premature labor and dysfunction, by using a phthalide derivative as an active component (JP-01050818). In their patent (U.S. Pat. No. 6,271,201), Board of Regents, the University of Texas System discloses a method for regulating placental cell production of thromboxane and $PGF_{2\alpha}$ comprising treating placenta cells with a pharmacologically effective amount of insulin-like growth factor I sufficient to inhibit thromboxane and prostaglandin $F_{2\alpha}$ production without affecting prostacyclin or prostaglandin $E_2$ production.

SUMMARY OF THE INVENTION

The present invention relates to the use of thiazolidine carboxamide derivatives of formula (II), (II)

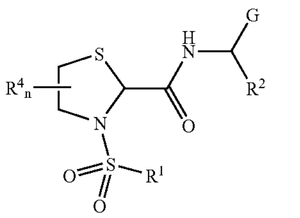

as well as pharmaceutically acceptable salts thereof, for the preparation of pharmaceutical compositions for the treatment and/or prevention of preterm labor, premature birth, dysmenorrhea, and for stopping labor prior to cesarean delivery. Compounds of this invention are inhibitors of prostaglandin receptors, particularly of the prostaglandin $F_{2\alpha}$ receptor (FP).

Also, the present invention relates to novel thiazolidine carboxamide derivatives of formula (I), wherein G' is an aryl, heteroaryl or cycloalkyl or a heterocycloalkyl moiety.

(I)

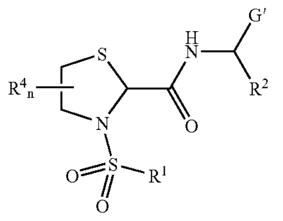

In particular the present invention relates to novel thiazolidine carboxamide derivatives of formula (Ia):

(Ia)

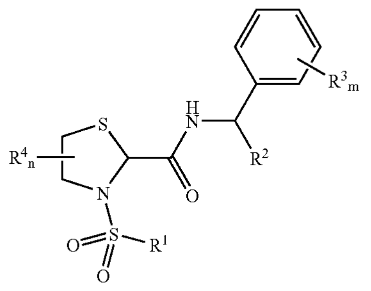

DETAILED DESCRIPTION OF THE INVENTION

It has now been found that compounds of the present invention are modulators of the Prostaglandin receptor, in particular of the Prostaglandin $F_{2\alpha}$ receptor (FP) function. When the Prostaglandin $F_{2\alpha}$ receptor (FP) is bound by the compounds of the present invention, $PGF_{2\alpha}$ is antagonized by being blocked from its receptor and thus being unable to exert its biological or pharmacological effects. The compounds of the present invention are therefore useful in the treatment and prevention of preterm labor, premature birth and for stopping labor prior to cesarean delivery.

The compounds of the present invention are also useful in the treatment of dysmenorrhea which may be defined as a cyclic pain associated with menses during ovulatory cycles. The pain is thought to result from uterine contractions and ischemia, probably mediated by the effect of prostaglandins produced in the secretory endometrium. By blocking both the effects of prostaglandin $F_{2\alpha}$ on the uterus, a FP antagonist is more efficacious for treating dysmenorrhea than current regimens.

In particular, compounds of the present invention are useful in the treatment and prevention of prostaglandin related disorders of mammals and especially humans. It is a purpose of this invention to provide a method of antagonizing the functions of prostaglandins, particularly prostaglandin $F_{2\alpha}$, in disease states in mammals. It is another purpose of this invention to develop a method of preventing or treating prostaglandin $F_{2\alpha}$ related disorders by antagonizing the binding of said prostaglandin to its receptor.

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenanthrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl ($-CH=CH_2$), n-2-propenyl (allyl, $-CH_2CH=CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl ($-C\equiv CH$), propargyl ($-CH_2C\equiv CH$), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group $-C(O)OH$.

"$C_1$-$C_5$-alkyl carboxy" refers to $C_1$-$C_5$-alkyl groups having an carboxy substituent, including 2-carboxyethyl and the like.

"Acyl" refers to the group $-(O)R$ where R includes "$C_1$-$C_6$-alkyl", "aryl", "heteroaryl", "$C_1$-$C_6$-alkyl aryl" or "$C_1$-$C_6$-alkyl heteroaryl".

"$C_1$-$C_5$-alkyl acyl" refers to $C_1$-$C_5$-alkyl groups having an acyl substituent, including 2-acetylethyl and the like.

"Acyloxy" refers to the group $-OC(O)R$ where R includes "$C_1$-$C_6$-alkyl", "aryl", "hetero-aryl", "$C_1$-$C_6$-alkyl aryl" or "$C_1$-$C_6$-alkyl heteroaryl".

"$C_1$-$C_5$-alkyl acyloxy" refers to $C_1$-$C_5$-alkyl groups having an acyloxy substituent, including 2-(acetyloxy)ethyl and the like.

"Alkoxy" refers to the group $-O-R$ where R includes "$C_1$-$C_6$-alkyl" or "aryl" or "hetero-aryl" or "$C_1$-$C_6$-alkyl aryl" or "$C_1$-$C_6$-alkyl heteroaryl". Preferred alkoxy groups include by way of example, methoxy, ethoxy, phenoxy and the like.

"$C_1$-$C_5$-alkyl alkoxy" refers to $C_1$-$C_5$-alkyl groups having an alkoxy substituent, including 2-ethoxyethyl and the like.

"Alkoxycarbonyl" refers to the group $-C(O)OR$ where R includes H, "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_5$-alkyl alkoxycarbonyl" refers to $C_1$-$C_5$-alkyl groups having an alkoxycarbonyl substituent, including 2-(benzyloxycarbonyl)ethyl and the like.

"Aminocarbonyl" refers to the group $-C(O)NRR'$ where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"$C_1$-$C_5$-alkyl aminocarbonyl" refers to $C_1$-$C_5$-alkyl groups having an aminocarbonyl substituent, including 2-(dimethylaminocarbonyl)ethyl and the like.

"Acylamino" refers to the group $-NRC(O)R'$ where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_5$-alkyl acylamino" refers to $C_1$-$C_5$-alkyl groups having an acylamino substituent, including 2-(propionylamino)ethyl and the like.

"Ureido" refers to the group $-NRC(O)NR'R''$ where each R, R', R'' is independently hydrogen or "$C_1$-$C_6$-alkyl" or "aryl" or "heteroaryl" or "$C_1$-$C_6$-alkyl aryl" or "$C_1$-$C_6$-alkyl heteroaryl" "cycloalkyl" or "heterocycloalkyl", and where R' and R'', together with the nitrogen atom to which they are attached, can optionally form a 3-8-membered hetero-cycloalkyl ring.

"$C_1$-$C_5$-alkyl ureido" refers to $C_1$-$C_5$-alkyl groups having an ureido substituent, including 2-(N'-methylureido)ethyl and the like.

"Amino" refers to the group $-NRR'$ where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_5$-alkyl amino" refers to $C_1$-$C_5$-alkyl groups having an amino substituent, including 2-(1-pyrrolidinyl)ethyl and the like.

"Ammonium" refers to a positively charged group —$N^+RR'R''$, where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "aryl", "heteroaryl", "$C_1$-$C_6$-alkyl aryl" or "$C_1$-$C_6$-alkyl heteroaryl".

"$C_1$-$C_5$-alkyl sulfonyloxy" refers to $C_1$-$C_5$-alkyl groups having a sulfonyloxy substituent, including 2-(methylsulfonyloxy)ethyl and the like.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_1$-$C_6$-alkyl aryl" or "$C_1$-$C_6$-alkyl heteroaryl".

"$C_1$-$C_5$-alkyl sulfonyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "aryl", "heteroaryl", "$C_1$-$C_6$-alkyl aryl" or "$C_1$-$C_6$-alkyl heteroaryl".

"$C_1$-$C_5$-alkyl sulfinyl" refers to $C_1$-$C_5$-alkyl groups having a sulfinyl substituent, including 2-(methylsulfinyl)ethyl and the like.

"Sulfonyl" refers to groups —S—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred sulfanyl groups include methylsulfanyl, ethylsulfanyl, and the like.

"$C_1$-$C_5$-alkyl sulfonyl" refers to $C_1$-$C_5$-alkyl groups having a sulfanyl substituent, including 2-(ethylsulfanyl)ethyl and the like.

"Sulfonylamino" refers to a group —$NRSO_2$—R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_5$-alkyl sulfonylamino" refers to $C_1$-$C_5$-alkyl groups having a sulfonylamino substituent, including 2-(ethylsulfonylamino)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cyclo-alkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "heteroaryl", "sulfinyl", "sulfonyl", "alkoxy", "sulfonyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, animals formed by ring closure for instance in an effort to obtain a protective group.

"Pharmaceutically acceptable salts or complexes" refers to salts or complexes of the below-identified compounds of formulae (I) and (II) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quaternary ammonium salt of the formula —NR, $R',R''^{+}Z^{-}$, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamate, mandelate, and diphenylacetate).

"Pharmaceutically active derivative" refers to any compound that upon administration to the recipient is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

A first aspect of the present invention consists in the use of compounds of formula (II)

(II)

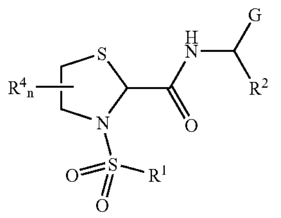

as well as its geometrical isomers, its optically active forms as enantiomers, diastereomers and its racemate forms, as well as pharmaceutically acceptable salts and pharmaceutically active derivatives thereof, for the preparation of a medicament for the treatment and/or prevention of preterm labor, premature birth, dysmenorrhea, and for stopping labor prior to cesarean delivery.

The substituents within formula (II) are defined as follows:

G is selected from the group consisting of substituted or unsubstituted $C_1$-$C_6$-alkyl aryl, substituted or unsubstituted $C_1$-$C_6$-alkyl heteroaryl, substituted or unsubstituted $C_1$-$C_6$-alkyl cycloalkyl, substituted or unsubstituted $C_1$-$C_6$-alkyl heteroaryl, substituted or unsubstituted aryl, substituted or unsubstituted heteroaryl, substituted or unsubstituted $C_3$-$C_8$-cycloalkyl or -heterocycloalkyl, said cycloalkyl or aryl or heteroaryl groups may be fused with cycloalkyl or aryl or heteroaryl groups.

$R^1$ is selected from the group consisting of substituted or unsubstituted aryl, substituted or unsubstituted heteroaryl, substituted or unsubstituted $C_3$-$C_8$-cycloalkyl or -heterocyclo-alkyl, said (hetero)cycloalkyl or aryl or heteroaryl groups may be fused with (hetero)-cycloalkyl or aryl or heteroaryl groups.

$R^2$ is H, carboxy, acyl, alkoxycarbonyl, aminocarbonyl, substituted or unsubstituted $C_1$-$C_5$-alkyl carboxy, substituted or unsubstituted $C_1$-$C_5$-alkyl acyl, substituted or unsubstituted $C_1$-$C_5$-alkyl alkoxycarbonyl, substituted or unsubstituted $C_1$-$C_5$-alkyl aminocarbonyl, substituted or unsubstituted $C_1$-$C_5$-alkyl acyloxy, substituted or unsubstituted $C_1$-$C_5$-alkyl acylamino, substituted or unsubstituted $C_1$-$C_5$-alkyl ureido, substituted or unsubstituted $C_1$-$C_5$-alkyl amino, substituted or unsubstituted $C_1$-$C_5$-alkyl alkoxy, substituted or unsubstituted $C_1$-$C_5$-alkyl sulfanyl, substituted or unsubstituted $C_1$-$C_5$-alkyl sulfinyl, substituted or unsubstituted $C_1$-$C_5$-alkyl sulfonyl, substituted or unsubstituted $C_1$-$C_8$-alkyl sulfonylamino, substituted or unsubstituted $C_1$-$C_5$-alkyl sulfonyloxy, substituted or unsubstituted $C_1$-$C_6$-alkyl, substituted or unsubstituted $C_1$-$C_6$-alkenyl, substituted or unsubstituted $C_2$-$C_6$-alkynyl, substituted or unsubstituted aryl, substituted or unsubstituted heteroaryl, substituted or unsubstituted $C_3$-$C_8$-cycloalkyl, substituted or unsubstituted heterocycloalkyl, substituted or unsubstituted $C_1$-$C_6$-alkyl aryl, substituted or unsubstituted $C_2$-$C_6$-alkyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, or substituted or unsubstituted $C_2$-$C_6$-alkynyl heteroaryl.

Alternatively, $R^2$ and G may form a $C_3$-$C_8$-cycloalkyl ring.

$R^4$ is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl.

n is an integer from 0 to 2.

According to one embodiment, G is an aryl group, e.g., a substituted or unsubstituted phenyl, like a biphenyl.

Compounds according to formula (II) are particularly useful for the treatment, including the acute management and the prophylaxis, of preterm labor.

In one embodiment of the present invention, the compounds according to formula (II) are suitable for the modulation, notably the inhibition of the activity of prostaglandins and particularly prostaglandin $F_{2\alpha}$. It is therefore believed that the compounds of the present invention are also particularly useful for the treatment and/or prevention of disorders which are mediated by prostaglandin $F_{2\alpha}$. Said treatment involves the modulation—notably the inhibition or the down regulation—of the prostaglandin function.

A further aspect of the invention consists in novel thiazolidine carboxamide derivatives of formula (I), wherein G' is a substituted or unsubstituted aryl, substituted or unsubstituted heteroaryl, substituted or unsubstituted $C_3$-$C_8$-cycloalkyl or -heterocycloalkyl, said cycloalkyl or aryl or heteroaryl groups may be fused with cycloalkyl or aryl or heteroaryl groups.

I

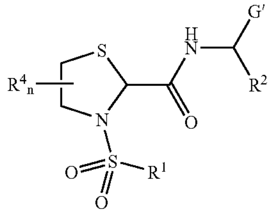

More preferred compounds have the formula (Ia):

(Ia)

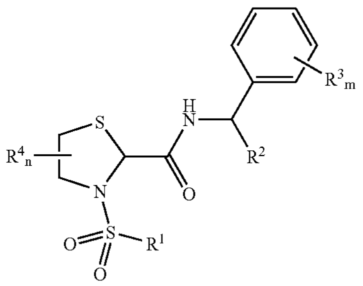

Formulae (I), (Ia) and (II) comprise also the geometrical isomers, the optically active forms, including enantiomers, diastereoisomers and its racemate forms, as well as pharmaceutically acceptable salts and pharmaceutically active derivatives thereof.

Substituents in formulae (I) and/or (Ia) are defined as follows:

$R^1$ is selected from the group consisting of substituted or unsubstituted aryl, substituted or unsubstituted heteroaryl, substituted or unsubstituted $C_3$-$C_8$-cycloalkyl or -heterocyclo-alkyl, said (hetero)cycloalkyl or aryl or heteroaryl groups may be fused with (hetero)cyclo-alkyl or aryl or heteroaryl groups.

In a more preferred embodiment according to the invention, $R^1$ is selected from the group consisting of an aryl or heteroaryl group optionally substituted with one or several substituents selected from the group consisting of aryl, heteroaryl, halogen, alkoxy, sulfanyl, straight or branched $C_1$-$C_6$-alkyl.

$R^2$ is selected from the group consisting of H, carboxy, acyl, substituted or unsubstituted alkoxycarbonyl, substituted or unsubstituted aminocarbonyl, substituted or unsubstituted $C_1$-$C_5$-alkyl carboxy, substituted or unsubstituted $C_1$-$C_5$-alkyl acyl, substituted or unsubstituted $C_1$-$C_5$-alkyl alkoxycarbonyl, substituted or unsubstituted $C_1$-$C_5$-alkyl aminocarbonyl, substituted or unsubstituted $C_1$-$C_5$-alkyl acyloxy, substituted or unsubstituted $C_1$-$C_5$-alkyl acylamino, substituted or unsubstituted $C_1$-$C_5$-alkyl ureido, substituted or unsubstituted $C_1$-$C_5$-alkyl amino, substituted or unsubstituted $C_1$-$C_5$-alkyl alkoxy, substituted or unsubstituted $C_1$-$C_5$-alkyl sulfanyl, substituted or unsubstituted $C_1$-$C_5$-alkyl sulfinyl, substituted or unsubstituted $C_1$-$C_5$-alkyl sulfonyl, substituted or unsubstituted $C_1$-$C_5$-alkyl sulfonylamino, substituted or unsubstituted $C_1$-$C_5$-alkyl sulfonyloxy, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl, substituted or unsubstituted heteroaryl, substituted or unsubstituted $C_3$-$C_8$-cycloalkyl, substituted or unsubstituted heterocycloalkyl, substituted or unsubstituted $C_1$-$C_6$-alkyl aryl, substituted or unsubstituted $C_2$-$C_6$-alkyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, or substituted or unsubstituted $C_2$-$C_6$-alkynyl heteroaryl.

In a preferred embodiment, $R^2$ is selected from the group consisting of carboxy, acyl, substituted or unsubstituted alkoxycarbonyl, aminocarbonyl, substituted or unsubstituted $C_1$-$C_5$-alkyl carboxy, substituted or unsubstituted $C_1$-$C_5$-alkyl acyl, substituted or unsubstituted $C_1$-$C_5$-alkyl alkoxycarbonyl, substituted or unsubstituted $C_1$-$C_5$-alkyl aminocarbonyl, substituted or unsubstituted $C_1$-$C_5$-alkyl acyloxy, substituted or unsubstituted $C_1$-$C_8$-alkyl acylamino, substituted or unsubstituted $C_1$-$C_5$-alkyl ureido, substituted or unsubstituted $C_1$-$C_5$-alkyl amino, substituted or unsubstituted $C_1$-$C_5$-alkyl alkoxy, substituted or unsubstituted $C_1$-$C_5$-alkyl sulfanyl, substituted or unsubstituted $C_1$-$C_5$-alkyl sulfinyl, substituted or unsubstituted $C_1$-$C_5$-alkyl sulfonyl, substituted or unsubstituted $C_1$-$C_5$-alkyl sulfonylamino, substituted or unsubstituted $C_1$-$C_5$-alkyl sulfonyloxy, substituted or unsubstituted aryl, substituted or unsubstituted heteroaryl.

More specifically, $R^2$ may be a group $C_1$-$C_3$-alkyl-A-$R^5$, wherein:

A is O or N—B—$R^6$.

B is a bond, an amino acid residue (e.g. alanine, phenylalanine, valine, leucine, isoleucine, proline, glycine, methionine, tryptophane, threonine, serine, etc.), (C═O), (C═O)—O, (C═O)—$NR^7$, or $SO_2$.

$R^5$, $R^6$ and $R^7$ are independently from each other selected from the group consisting of H, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl, substituted or unsubstituted heteroaryl, substituted or unsubstituted $C_3$-$C_8$-cycloalkyl or heterocycloalkyl, substituted or unsubstituted $C_1$-$C_6$-alkyl aryl, substituted or unsubstituted $C_1$-$C_6$-alkyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl aryl or heteroaryl, substituted or unsubstituted $C_2$-$C_6$-alkynyl aryl or -heteroaryl.

$R^5$ and B—$R^6$ (in particular if B is a bond), and similarly $R^6$ and $R^7$ (if B is (C═O)—$NR^7$), together with the respective nitrogen atoms to which they are attached, can optionally form substituted or unsubstituted heterocycloalkyl rings.

In an even more preferred embodiment, $R^2$ is $C_1$-$C_3$-alkyl-A-$R^5$ wherein A is O and $R^5$ is H, or A is N—B—$R^6$ with B being a bond, and $R^5$ and $R^6$ being each independently from each other selected from the group consisting of substituted or unsubstituted $C_1$-$C_3$-alkyl, e.g. $C_1$-$C_3$-alkyl hydroxy, $C_1$-$C_3$-alkyl carboxy, $C_1$-$C_3$-alkyl aminocarbonyl, $C_1$-$C_3$-alkyl alkoxycarbonyl, substituted or unsubstituted $C_1$-$C_3$-alkyl aryl, substituted or unsubstituted $C_1$-$C_3$-alkyl heteroaryl, substituted or unsubstituted $C_1$-$C_3$-alkyl cycloalkyl, substituted or unsubstituted $C_1$-$C_3$-alkyl heterocycloalkyl, substituted or unsubstituted $C_1$-$C_3$-alkyl hydroxy, substituted or unsubstituted $C_1$-$C_3$-alkyl carboxy, substituted or unsubstituted $C_1$-$C_3$-alkyl aminocarbonyl, substituted or unsubstituted $C_1$-$C_3$-alkyl alkoxycarbonyl.

According to a further preferred embodiment, $R^2$ is a substituted or unsubstituted phenyl, pyrid-2-yl, pyrid-3-yl, or pyrid-4-yl.

Said phenyl, pyrid-2-yl, pyrid-3-yl, or pyrid-4-yl moieties may optionally be substituted by at least one substituent selected from the group consisting of H, hydroxy, halogen, carboxy, acyl, aminocarbonyl, acylamino, $C_1$-$C_3$-alkyl amino, $C_1$-$C_3$-alkyl alkoxy, $C_1$-$C_3$-alkyl carboxy, $C_1$-$C_3$-alkyl acyl, $C_1$-$C_3$-alkyl aminocarbonyl, $C_1$-$C_3$-alkyl acylamino, $C_1$-$C_3$-alkyl ureido, $C_1$-$C_3$-alkyl sulfanyl, $C_1$-$C_3$-alkyl sulfinyl, $C_1$-$C_3$-alkyl sulfonyl, $C_1$-$C_3$-alkyl sulfonylamino. Most preferred substituents are methoxy, carboxy-methoxy, hydroxy-methyl, carboxymethyl, sulfonyloxymethyl, dimethylaminomethyl, 4-morpholinylmethyl, 1-piperidinylmethyl, 1-pyrrolidinylmethyl, (4-methyl-1-piperazinyl)-methyl, ethoxy, 2-methoxyethoxy, 2-hydroxyethoxy, 2-carboxymethoxy, 2-sulfonyloxy-ethoxy, 2-(dimethyl-amino)ethoxy, 2-(4-morpholinyl)ethoxy, 2-(1-pyrrolidinyl)ethoxy, 2-(1-piperidinyl)ethoxy, 2-(4-methyl-1-piperazinyl)ethoxy, 2-hydroxyethyl, 2-methoxyethyl, 2-carboxyethyl, 2-sulfonyloxyethyl, 2-(dimethylamino)ethyl, 2-(4-morpholinyl)ethyl, 2-(1-pyrrolidinyl)ethyl, 2-(1-piperidinyl)ethyl, 2-(4-methyl-1-piperazinyl)ethyl, propoxy, 3-methoxypropoxy, 3-hydroxypropoxy, 3-carboxypropoxy, 3-sulfonyloxypropoxy, 3-(dimethylamino)propoxy, 3-(4-morpholinyl)propoxy, 3-(1-pyrrolidinyl)propoxy, 3-(1-piperidinyl)propoxy, 3-(4-methyl-1-piperazinyl)propoxy, 3-hydroxypropyl, 3-methoxypropyl, 3-carboxypropyl, 3-sulfonyloxypropyl, 3-(dimethylamino)propyl, 3-(4-morpholinyl)propyl, 3-(1-pyrrolidinyl)-propyl, 3-(1-piperidinyl)propyl, 3-(4-methyl-1-piperazinyl)propyl.

$R^3$ is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl, heteroaryl, substituted or unsubstituted $C_3$-$C_8$-cycloalkyl or substituted or unsubstituted heterocycloalkyl, substituted or unsubstituted $C_1$-$C_6$-alkyl aryl, substituted or unsubstituted $C_1$-$C_6$-alkyl heteroaryl, substituted or unsubstituted $C_1$-$C_3$-alkyl cycloalkyl, substituted or unsubstituted $C_1$-$C_3$-alkyl heterocycloalkyl, substituted or unsubstituted $C_2$-$C_6$-alkenyl-aryl or -heteroaryl, substituted or unsubstituted $C_2$-$C_6$-alkynyl aryl or -heteroaryl, carboxy, cyano, halogen, hydroxy, alkoxy, nitro, acylamino, ureido, sulfonylamino, sulfanyl, or sulfonyl.

m is an integer from 0 to 3 and n is an integer from 0 to 2.

$R^4$ is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl.

In a particularly preferred embodiment, $R^1$ is a phenyl substituted with a group selected from straight or branched $C_1$-$C_5$-alkyl or aryl, $R^2$ is selected from the group consisting of $C_1$-$C_3$-alkyl-A-$R^5$ wherein A is O and $R^5$ is H, or A is N—B—$R^6$ with B being a bond and $R^5$ and $R^6$ being each independently selected from the group consisting of $C_1$-$C_3$-alkyl, $C_1$-$C_3$-alkyl aryl, $C_1$-$C_3$-alkyl heteroaryl, $C_1$-$C_3$-alkyl-hydroxy.

In a more particularly preferred embodiment, $R^1$ is a biphenyl or a tert-butyl phenyl group, $R^2$ is $C_1$-$C_3$-alkyl-A-$R^5$, wherein A is O and $R^5$ is H, or A is N—B—$R^6$, $R^5$ and $R^6$ are each independently from each other $C_1$-$C_3$-alkyl, $C_1$-$C_3$-alkyl aryl, $C_1$-$C_3$-alkyl heteroaryl, or $C_1$-$C_3$-alkyl hydroxy, B is a bond, $R^3$ is fluorine, m is either 0, 1, or 2, and n is 0.

In another more particularly preferred embodiment, $R^1$ is a biphenyl or a tert-butyl phenyl group, $R^2$ is pyrid-2-yl, carrying one or several substituents selected from the group consisting of H, OH, alkoxy, $C_1$-$C_3$-alkyl amino, $C_1$-$C_3$-alkyl hydroxy, $C_1$-$C_3$-alkyl carboxy, $C_1$-$C_3$-alkyl sulfonyloxy, $R^3$ is fluorine, m is either 0, 1, or 2, and n is 0.

Compounds of the present invention are in particular those of the group consisting of:

(2R)-3-([1,1'-biphenyl]-4-ylsulfonyl)-N-[(1S)-3-hydroxy-1-phenylpropyl]-1,3-thiazolidine-2-carboxamide (2R)-3-([1,1'-biphenyl]-4-ylsulfonyl)-N—[(R)-phenyl(2-pyridinyl)methyl]-1,3-thiazolidine-2-carboxamide (2R)-3-[(4-tert-butylphenyl)sulfonyl]-N-[(1S)-3-hydroxy-1-phenylpropyl]-1,3-thiazolidine-2-carboxamide (2R)—N-[(1S)-3-hydroxy-1-phenylpropyl]-3-[(4-tert-pentylphenyl)sulfonyl]-1,3-thiazolidine-2-carboxamide (2S)-2-({[3-([1,1'-biphenyl]-4-ylsulfonyl)-1,3-thiazolidin-2-yl]carbonyl}amino)-3-phenylpropanoic acid (2S)-2-[({3-[(5-chloro-3-methyl-1-benzothien-2-yl)sulfonyl]-1,3-thiazolidin-2-yl}carbonyl)amino]-3-phenylpropanoic acid (2S)-3-([1,1'-biphenyl]-4-ylsulfonyl)-N-((1S)-3-{methyl[2-(2-pyridinyl)ethyl]amino}-1-phenylpropyl)-1,3-thiazolidine-2-carboxamide (2S)-3-([, 1'-biphenyl]-4-ylsulfonyl)-N-[(1S)-1-phenyl-2-propenyl]-1,3-thiazolidine-2-carboxamide (2S)-3-([1,1'-biphenyl]-4-ylsulfonyl)-N-[(1S)-3-(diethylamino)-1-phenylpropyl]-1,3-thiazolidine-2-carboxamide (2S)-3-([1,1'-biphenyl]-4-ylsulfonyl)-N-[(1S)-3-hydroxy-1-phenylpropyl]-1,3-thiazolidine-2-carboxamide (2S)-3-([1,1'-biphenyl]-4-ylsulfonyl)-N—[(R)-phenyl(2-pyridinyl)methyl]-1,3-thiazolidine-2-carboxamide (2S)-3-([1,1'-biphenyl]-4-ylsulfonyl)-N-{(1S)-3-[(2-furylmethyl(methyl)amino]-1-phenylpropyl}-1,3-thiazolidine-2-carboxamide (2S)-3-([1,1'-biphenyl]-4-ylsulfonyl)-N-{(1S)-3-[(2-hydroxyethyl)(methyl)amino]-1-phenylpropyl}-1,3-thiazolidine-2-carboxamide (2S)-3-([1,1'-biphenyl]-4-ylsulfonyl)-N-{(1S)-3-[2-(2-hydroxyethyl)-1-piperidinyl]-1-phenylpropyl}-1,3-thiazolidine-2-carboxamide (2S)-3-([1,1'-biphenyl]-4-ylsulfonyl)-N-{(1S)-3-[4-(2-methoxyphenyl)-1-piperazinyl]-1-phenylpropyl}-1,3-thiazolidine-2-carboxamide (2S)-3-[(4-tert-butylphenyl)sulfonyl]-N-[(1S)-3-hydroxy-1-phenylpropyl]-1,3-thiazolidine-2-carboxamide (2S)-3-phenyl-2-{[(3-{[5-(2-pyridinyl)-2-thienyl]sulfonyl}-1,3-thiazolidin-2-yl)carbonyl]amino}propanoic acid (2S)—N-[(1S)-3-hydroxy-1-phenylpropyl]-3-[(4-tert-pentylphenyl)sulfonyl]-1,3-thiazolidine-2-carboxamide (2S)—N-{(1S)-3-[benzyl(methyl)amino]-1-phenylpropyl}-3-([1,1'-biphenyl]-4-ylsulfonyl)-1,3-thiazolidine-2-carboxamide 3-([1,1'-biphenyl]-4-ylsulfonyl)-N-(1-phenyl-3-{[(2S)-tetrahydro-2-furanylmethyl]amino}-propyl)-1,3-thiazolidine-2-carboxamide 3-([1,1'-biphenyl]-4-ylsulfonyl)-N-(1-phenyl-3-{[2-(1-piperidinyl)ethyl]amino}propyl)-1,3-thiazolidine-2-carboxamide 3-([1,1'-biphenyl]-4-ylsulfonyl)-N-(1-phenyl-3-{[2-(2-pyridinyl)ethyl]amino}propyl) 1,3-thiazolidine-2-carboxamide 3-([1,1'-biphenyl]-4-ylsulfonyl)-N-(1-phenyl-3-{[2-(3-pyridinyl)ethyl]amino}propyl)-1,3-thiazolidine-2-carboxamide 3-([1,1'-biphenyl]-4-ylsulfonyl)-N-(1-phenylpropyl)-1,3-thiazolidine-2-carboxamide 3-([1,1'-biphenyl]-4-ylsulfonyl)-N-(2,3-difluorobenzyl)-1,3-thiazolidine-2-carboxamide 3-([1,1'-biphenyl]-4-ylsulfonyl)-N-(2,4-difluorobenzyl)-1,3-thiazolidine-2-carboxamide 3-([1,1'-biphenyl]-4-ylsulfonyl)-N-(2,5-difluorobenzyl)-1,3-thiazolidine-2-carboxamide 3-([1,1'-biphenyl]-4-ylsulfonyl)-N-(2,6-difluorobenzyl)-1,3-thiazolidine-2-carboxamide 3-([1,1'-biphenyl]-4-ylsulfonyl)-N-(2-chloro-4-fluorobenzyl)-1,3-thiazolidine-2-carboxamide 3-([1,1'-biphenyl]-4-ylsulfonyl)-N-(2-fluorobenzyl)-1,3-thiazolidine-2-carboxamide 3-([1,1'-biphenyl]-4-ylsulfonyl)-N-(2-furylmethyl)-1,3-thiazolidine-2-carboxamide 3-([1,1'-biphenyl]-4-ylsulfonyl)-N-(2-methoxybenzyl)-1,3-thiazolidine-2-carboxamide 3-([1,1'-biphenyl]-4-ylsulfonyl)-N-(2-methylbenzyl)-1,3-thiazolidine-2-carboxamide 3-([1,1'-biphenyl]-4-ylsulfonyl)-N-(2-phenylpropyl)-1,3-thiazolidine-2-carboxamide 3-([1,1'-biphenyl]-4-ylsulfonyl)-N-(2-thienylmethyl)-1,3-thiazolidine-2-carboxamide 3-([1,1'-biphenyl]-4-ylsulfonyl)-N-(3,4-difluorobenzyl)-1,3-thiazolidine-2-carboxamide 3-([1,1'-biphenyl]-4-ylsulfonyl)-N-(3-{[(2R)-2-hydroxy-2-phenylethyl]amino}-1-phenylpropyl)-1,3-thiazolidine-2-carboxamide 3-([1,1'-biphenyl]-4-ylsulfonyl)-N-(3-{[(2S)-2-hydroxypropyl]amino}-1-phenylpropyl)-1,3-thiazolidine-2-carboxamide 3-([1,1'-biphenyl]-4-ylsulfonyl)-N-(3-{[(5-methyl-2-furyl)methyl]amino}-1-phenylpropyl)-1,3-thiazolidine-2-carboxamide 3-([1,1'-biphenyl]-4-ylsulfonyl)-N-(3-{[2-(1H-indol-3-yl)ethyl]amino}-1-phenylpropyl)-1,3-thiazolidine-2-carboxamide 3-([1,1'-biphenyl]-4-ylsulfonyl)-N-(3-{[2-(1-methyl-2-pyrrolidinyl)ethyl]amino}-1-phenylpropyl)-1,3-thiazolidine-2-carboxamide 3-([1,1'-biphenyl]-4-ylsulfonyl)-N-(3-{[2-(4-morpholinyl)ethyl]amino}-1-phenylpropyl)-1,3-thiazolidine-2-carboxamide 3-([1,1'-biphenyl]-4-ylsulfonyl)-N-(3-{[2-(dimethylamino)ethyl]amino}-1-phenylpropyl)-1,3-thiazolidine-2-carboxamide 3-([1,1'-biphenyl]-4-ylsulfonyl)-N-(3-{[3-(2-oxo-1-pyrrolidinyl)propyl]amino}-1-phenyl-propyl)-1,3-thiazolidine-2-carboxamide 3-([1,1'-biphenyl]-4-ylsulfonyl)-N-(3-{[3-(4-morpholinyl)propyl]amino}-1-phenylpropyl)-1,3-thiazolidine-2-carboxamide 3-([1,1'-biphenyl]-4-ylsulfonyl)-N-(3-{methyl[(14S)-1-phenylethyl]amino}-1-phenyl-propyl)-1,3-thiazolidine-2-carboxamide 3-([1,1'-biphenyl]-4-ylsulfonyl)-N-(3-{methyl[(1S)-1-phenylethyl]amino}-1-phenylpropyl)-1,3-thiazolidine-2-carboxamide 3-([1,1'-biphenyl]-4-ylsulfonyl)-N-(3-{methyl[2-(2-pyridinyl)ethyl]amino}-1-phenyl-propyl)-1,3-thiazolidine-2-carboxamide 3-([1,1'-biphenyl]-4-ylsulfonyl)-N-(3-chloro-4-fluorobenzyl)-1,3-thiazolidine-2-carboxamide 3-([1,1'-biphenyl]-4-ylsulfonyl)-N-(3-fluorobenzyl)-1,3-thiazolidine-2-carboxamide 3-([1,1'-biphenyl]-4-ylsulfonyl)-N-(3-hydroxy-1-phenylpropyl)-1,3-thiazolidine-2-carboxamide 3-([1,1'-biphenyl]-4-ylsulfonyl)-N-(3-methylbenzyl)-1,3-thiazolidine-2-carboxamide 3-([1,1'-biphenyl]-4-ylsulfonyl)-N-(3-phenoxy-1-phenylpropyl)-1,3-thiazolidine-2-carboxamide 3-([1,1'-biphenyl]-4-ylsulfonyl)-N-(3-pyridinylmethyl)-1,3-thiazolidine-2-carboxamide 3-([1,1'-biphenyl]-4-ylsulfonyl)-N-(4-fluorobenzyl)-1,3-thiazolidine-2-carboxamide 3-([1,1'-biphenyl]-4-ylsulfonyl)-N-(4-phenoxybenzyl)-1,3-thiazolidine-2-carboxamide 3-([1,1'-biphenyl]-4-ylsulfonyl)-N-[(1,5-dimethyl-1H-pyrrol-2-yl)methyl]-1,3-thiazolidine-2-carboxamide 3-([1,1'-biphenyl]-4-ylsulfonyl)-N-[(1-oxido-2-pyridinyl)methyl]-1,3-thiazolidine-2-carboxamide 1-oxide
3-([1,1'-biphenyl]-4-ylsulfonyl)-N-[(1R)-2-hydroxy-1-phenylethyl]-1,3-thiazolidine-2-carboxamide
3-([1,1'-biphenyl]-4-ylsulfonyl)-N-[(1R)-3-hydroxy-1-phenylpropyl]-1,3-thiazolidine-2-carboxamide
3-([1,1'-biphenyl]-4-ylsulfonyl)-N-[(1S)-1-phenylethyl]-1,3-thiazolidine-2-carboxamide
3-([1,1'-biphenyl]-4-ylsulfonyl)-N-[(1S)-3-hydroxy-1-phenylpropyl]-1,3-thiazolidine-2-carboxamide
3-([1,1'-biphenyl]-4-ylsulfonyl)-N—[(R)-{6-[2-(dimethylamino)ethoxy]-2-pyridinyl}-(phenyl)methyl]-1,3-thiazolidine-2-carboxamide
3-([1,1'-biphenyl]-4-ylsulfonyl)-N—[(R)-phenyl(2-pyridinyl)methyl]-1,3-thiazolidine-2-carboxamide
3-([1,1'-biphenyl]-4-ylsulfonyl)-N—[(S)-phenyl(2-pyridinyl)methyl]-1,3-thiazolidine-2-carboxamide
3-([1,1'-biphenyl]-4-ylsulfonyl)-N-[1-(2,6-difluorophenyl)-3-hydroxypropyl]-1,3-thiazolidine-2-carboxamide
3-([1,1'-biphenyl]-4-ylsulfonyl)-N-[1-(2-chlorophenyl)-3-hydroxypropyl]-1,3-thiazolidine-2-carboxamide
3-([1,1'-biphenyl]-4-ylsulfonyl)-N-[1-(2-furyl)-3-hydroxypropyl]-1,3-thiazolidine-2-carboxamide
3-([1,1'-biphenyl]-4-ylsulfonyl)-N-[1-(3,4-dichlorophenyl)-3-hydroxypropyl]-1,3-thiazolidine-2-carboxamide
3-([1,1'-biphenyl]-4-ylsulfonyl)-N-[1-(3-chlorophenyl)-3-hydroxypropyl]-1,3-thiazolidine-2-carboxamide
3-([1,1'-biphenyl]-4-ylsulfonyl)-N-[1-(3-furyl)-3-hydroxypropyl]-1,3-thiazolidine-2-carboxamide
3-([1,1'-biphenyl]-4-ylsulfonyl)-N-[1-(4-chlorophenyl)-3-hydroxypropyl]-1,3-thiazolidine-2-carboxamide
3-([1,1'-biphenyl]-4-ylsulfonyl)-N-[1-(4-chlorophenyl)ethyl]-1,3-thiazolidine-2-carboxamide
3-([1,1'-biphenyl]-4-ylsulfonyl)-N-[1-(4-fluorophenyl)-3-hydroxypropyl]-1,3-thiazolidine-2-carboxamide
3-([1,1'-biphenyl]-4-ylsulfonyl)-N-[1-(4-fluorophenyl)ethyl]-1,3-thiazolidine-2-carboxamide
3-([1,1'-biphenyl]-4-ylsulfonyl)-N-[1-phenyl-2-(1-pyrrolidinyl)ethyl]-1,3-thiazolidine-2-carboxamide
3-([1,1'-biphenyl]-4-ylsulfonyl)-N-[1-phenyl-3-({[(1S,2R,3R,5S)-2,6,6-trimethylbicyclo-[3.1.1]hept-3-yl]methyl}amino)propyl]-1,3-thiazolidine-2-carboxamide
3-([1,1'-biphenyl]-4-ylsulfonyl)-N-[1-phenyl-3-(1-piperazinyl)propyl]-1,3-thiazolidine-2-carboxamide
3-([1,1'-biphenyl]-4-ylsulfonyl)-N-[1-phenyl-3-(1-piperidinyl)propyl]-1,3-thiazolidine-2-carboxamide
3-([1,1'-biphenyl]-4-ylsulfonyl)-N-[1-phenyl-3-(1-pyrrolidinyl)propyl]-1,3-thiazolidine-2-carboxamide
3-([1,1'-biphenyl]-4-ylsulfonyl)-N-[2-(4-morpholinyl)-1-phenylethyl 1]-1,3-thiazolidine-2-carboxamide
3-([1,1'-biphenyl]-4-ylsulfonyl)-N-[2-(dimethylamino)-1-phenylethyl]1,3-thiazolidine-2-carboxamide
3-([1,1'-biphenyl]-4-ylsulfonyl)-N-[3-((3R)-3-(hydroxymethyl)-3,4-dihydro-2(1H)-isoquinolinyl)-1-phenylpropyl]-1,3-thiazolidine-2-carboxamide
3-([1,1'-biphenyl]-4-ylsulfonyl)-N-[3-((3S)-3-(hydroxymethyl)-3,4-dihydro-2(1H)-isoquinolinyl)-1-phenylpropyl]-1,3-thiazolidine-2-carboxamide
3-([1,1'-biphenyl]-4-ylsulfonyl)-N-[3-(1,3-dioxo-1,3-dihydro-2H-isoindol-2-yl)-1-phenylpropyl]-1,3-thiazolidine-2-carboxamide
3-([1,1'-biphenyl]-4-ylsulfonyl)-N-[3-(2,5-dihydro-1H-pyrrol-1-yl)-1-phenylpropyl]-1,3-thiazolidine-2-carboxamide
3-([1,1'-biphenyl]-4-ylsulfonyl)-N-[3-(3,5-dimethyl-1-piperidinyl)-1-phenylpropyl]-1,3-thiazolidine-2-carboxamide
3-([1,1'-biphenyl]-4-ylsulfonyl)-N-[3-(3,6-dihydro-1(2H)-pyridinyl)-1-phenylpropyl]-1,3-thiazolidine-2-carboxamide
3-([1,1'-biphenyl]-4-ylsulfonyl)-N-[3-(3-hydroxy-1-piperidinyl)-1-phenylpropyl]-1,3-thiazolidine-2-carboxamide
3-([1,1'-biphenyl]-4-ylsulfonyl)-N-[3-(3-hydroxy-1-pyrrolidinyl)-1-phenylpropyl]-1,3-thiazolidine-2-carboxamide
3-([1,1'-biphenyl]-4-ylsulfonyl)-N-[3-(3-methyl-1-piperidinyl)-1-phenylpropyl]-1,3-thiazolidine-2-carboxamide
3-([1,1'-biphenyl]-4-ylsulfonyl)-N-[3-(4-hydroxy-1-piperidinyl)-1-phenylpropyl]-1,3-thiazolidine-2-carboxamide
3-([1,1'biphenyl]-4-ylsulfonyl)-N-[3-(4-hydroxy-4-phenyl-1-piperidinyl)-1-phenylpropyl]-1,3-thiazolidine-2-carboxamide
3-([1,1'-biphenyl]-4-ylsulfonyl)-N-[3-(4-methyl-1-piperazinyl)-1-phenylpropyl]-1,3-thiazolidine-2-carboxamide
3-([1,1'-biphenyl]-4-ylsulfonyl)-N-[3-(4-morpholinyl)-1-phenylpropyl]-1,3-thiazolidine-2-carboxamide
3-([1,1'-biphenyl]-4-ylsulfonyl)-N-[3-(diethylamino)-1-phenylpropyl]-1,3-thiazolidine-2-carboxamide
3-([1,1'-biphenyl]-4-ylsulfonyl)-N-[3-(dimethylamino)-1-phenylpropyl]-1,3-thiazolidine-2-carboxamide
3-([1,1'-biphenyl]-4-ylsulfonyl)-N-[3-hydroxy-1-(2-methoxyphenyl)propyl]-1,3-thiazolidine-2-carboxamide
3-([1,1'-biphenyl]-4-ylsulfonyl)-N-[3-hydroxy-1-(2-methylphenyl)propyl]-1,3-thiazolidine-2-carboxamide
3-([1,1'-biphenyl]-4-ylsulfonyl)-N-[3-hydroxy-1-(3-methoxyphenyl)propyl]-1,3-thiazolidine-2-carboxamide
3-([1,1'-biphenyl]-4-ylsulfonyl)-N-[3-hydroxy-1-(3-pyridinyl)propyl]-1,3-thiazolidine-2-carboxamide
3-([1,1'-biphenyl]-4-ylsulfonyl)-N-[3-hydroxy-1-(4-methoxyphenyl)propyl]-1,3-thiazolidine-2-carboxamide
3-([1,1'-biphenyl]-4-ylsulfonyl)-N-[3-hydroxy-1-(4-methylphenyl)propyl]-1,3-thiazolidine-2-carboxamide
3-([1,1'-biphenyl]-4-ylsulfonyl)-N-[phenyl(2-pyridinyl)methyl]-1,3-thiazolidine-2-carboxamide
3-([1,1'-biphenyl]-4-ylsulfonyl)-N-{1-phenyl-3-[(2-phenylethyl)amino]propyl}-1,3-thiazolidine-2-carboxamide
3-([1,1'-biphenyl]-4-ylsulfonyl)-N-{1-phenyl-3-[(2-phenylpropyl)amino]propyl}-1,3-thiazolidine-2-carboxamide
3-([1,1'-biphenyl]-4-ylsulfonyl)-N-{1-phenyl-3-[(2-pyridinylmethyl)amino]propyl}-1,3-thiazolidine-2-carboxamide
3-([1,1'-biphenyl]-4-ylsulfonyl)-N-{1-phenyl-3-[(3-pyridinylmethyl)amino]propyl}-1,3-thiazolidine-2-carboxamide
3-([1,1'-biphenyl]-4-ylsulfonyl)-N-{1-phenyl-3-[(tetrahydro-2-furanylmethyl)amino]-propyl}-1,3-thiazolidine-2-carboxamide
3-([1,1'-biphenyl]-4-ylsulfonyl)-N-{1-phenyl-3-[4-(1-pyrrolidinyl)-1-piperidinyl]propyl}-1,3-thiazolidine-2-carboxamide
3-([1,1'-biphenyl]-4-ylsulfonyl)-N-{3-[(2-furylmethyl)(methyl)amino]-1-phenylpropyl}-1,3-thiazolidine-2-carboxamide
3-([1,1'-biphenyl]-4-ylsulfonyl)-N-{3-[(2-furylmethyl)amino]-1-phenylpropyl}-1,3-thiazolidine-2-carboxamide
3-([1,1'-biphenyl]-4-ylsulfonyl)-N-{3-[(2-hydroxy-2-phenylethyl)(methyl)amino]-1-phenylpropyl}-1,3-thiazolidine-2-carboxamide
3-([1,1'-biphenyl]-4-ylsulfonyl)-N-{3-[(2-hydroxy-2-phenylethyl)amino]-1-phenylpropyl}-1,3-thiazolidine-2-carboxamide 3-([1,1'-biphenyl]-4-ylsulfonyl)-N-{3-[(2-hydroxycyclohexyl)amino]-1-phenylpropyl}-1,3-thiazolidine-2-carboxamide
3-([1,1'-biphenyl]-4-ylsulfonyl)-N-{3-[(2-hydroxyethyl)(methyl)amino]-1-phenylpropyl}-1,3-thiazolidine-2-carboxamide
3-([1,1'-biphenyl]-4-ylsulfonyl)-N-{3-[(2-hydroxyethyl)amino]-1-phenylpropyl}-1,3-thiazolidine-2-carboxamide
3-([1,1'-biphenyl]-4-ylsulfonyl)-N-{3-[(2-hydroxypropyl)amino]-1-phenylpropyl}-1,3-thiazolidine-2-carboxamide
3-([1,1'-biphenyl]-4-ylsulfonyl)-N-{3-[(2R)-2-(hydroxymethyl)pyrrolidinyl]-1-phenyl-propyl}-1,3-thiazolidine-2-carboxamide
3-([1,1'-biphenyl]-4-ylsulfonyl)-N-{3-[(2R)-2-(methoxymethyl)pyrrolidinyl]-1-phenyl-propyl}-1,3-thiazolidine-2-carboxamide
3-([1,1'-biphenyl]-4-ylsulfonyl)-N-{3-[(2S)-2-(methoxymethyl)pyrrolidinyl]-1-phenyl-propyl}-1,3-thiazolidine-2-carboxamide
3-([1,1'-biphenyl]-4-ylsulfonyl)-N-{3-[(3,5-difluorobenzyl)amino]-1-phenylpropyl}-1,3-thiazolidine-2-carboxamide
3-([1,1'-biphenyl]-4-ylsulfonyl)-N-{3-[(3-hydroxy-3-phenylpropyl)(methyl)amino]-1-phenylpropyl}-1,3-thiazolidine-2-carboxamide
3-([1,1'-biphenyl]-4-ylsulfonyl)-N-{3-[(3-hydroxypropyl)amino]-1-phenylpropyl}-1,3-thiazolidine-2-carboxamide
3-([1,1'-biphenyl]-4-ylsulfonyl)-N-{3-[(3R)-3-hydroxypyrrolidinyl]-1-phenylpropyl}-1,3-thiazolidine-2-carboxamide
3-([1,1'-biphenyl]-4-ylsulfonyl)-N-{3-[(4-fluorobenzyl)amino]-1-phenylpropyl}-1,3-thiazolidine-2-carboxamide
3-([1,1'-biphenyl]-4-ylsulfonyl)-N-{3-[[3-(dimethylamino)propyl](methyl)amino]-1-phenylpropyl}-1,3-thiazolidine-2-carboxamide
3-([1,1'-biphenyl]-4-ylsulfonyl)-N-{3-[2-(hydroxymethyl)-1-piperidinyl]-1-phenylpropyl}-1,3-thiazolidine-2-carboxamide
3-([1,1'-biphenyl]-4-ylsulfonyl)-N-{3-[3-(hydroxymethyl)-1-piperidinyl]-1-phenylpropyl}-1,3-thiazolidine-2-carboxamide
3-([1,1'-biphenyl]-4-ylsulfonyl)-N-{3-[4-(2-hydroxyethyl)-1-piperidinyl]-1-phenylpropyl}-1,3-thiazolidine-2-carboxamide
3-([1,1'-biphenyl]-4-ylsulfonyl)-N-{3-[4-(hydroxymethyl)-1-piperidinyl]-1-phenylpropyl}-1,3-thiazolidine-2-carboxamide
3-([1,1'-biphenyl]-4-ylsulfonyl)-N-{3-[methyl(2-phenylethyl)amino]-1-phenylpropyl}-1,3-thiazolidine-2-carboxamide
3-[(3',4'-dichloro[,1'-biphenyl]-4-yl)sulfonyl]-N-[1-(2-furyl)-3-hydroxypropyl]-1,3-thiazolidine-2-carboxamide
3-[(4'-chloro[1,1'-biphenyl]-4-yl)sulfonyl]-N-[1-(2-furyl)-3-hydroxypropyl]-1,3-thiazolidine-2-carboxamide
3-[(4-chlorophenyl)sulfonyl]-N-(2-pyridinylmethyl)-1,3-thiazolidine-2-carboxamide
3-[(4-chlorophenyl)sulfonyl]-N-{4-[({[(2-ethylhexyl)amino]carbonyl}amino)methyl]benzyl}-1,3-thiazolidine-2-carboxamide
3-[(4-chlorophenyl)sulfonyl]-N-{4-[({[(2-phenylethyl)amino]carbonyl}amino)methyl]benzyl}-1,3-thiazolidine-2-carboxamide
3-[(4-chlorophenyl)sulfonyl]-N-{4-[({[(4-methylbenzyl)amino]carbonyl}amino)methyl]benzyl}-1,3-thiazolidine-2-carboxamide
3-[(4'-fluoro[1,1'-biphenyl]-4-yl)sulfonyl]-N-[1-(2-furyl)-3-hydroxypropyl]-1,3-thiazolidine-2-carboxamide
3-[(4-iodophenyl)sulfonyl]-N-{4-[({[(4-methylbenzyl)amino]carbonyl}amino)methyl]-benzyl}-1,3-thiazolidine-2-carboxamide
3-[(4-tert-butylphenyl)sulfonyl]-N-(1,2-diphenylethyl)-1,3-thiazolidine-2-carboxamide
3-[(4-tert-butylphenyl)sulfonyl]-N-(1-phenylethyl)-1,3-thiazolidine-2-carboxamide
3-[(4-tert-butylphenyl)sulfonyl]-N-(2,3-dihydro-1H-inden-1-yl)-1,3-thiazolidine-2-carboxamide
3-[(4-tert-butylphenyl)sulfonyl]-N-(2-furylmethyl)-1,3-thiazolidine-2-carboxamide
3-[(4-tert-butylphenyl)sulfonyl]-N-(2-phenylpropyl)-1,3-thiazolidine-2-carboxamide
3-[(4-tert-butylphenyl)sulfonyl]-N-(3-hydroxy-1-phenylpropyl)-1,3-thiazolidine-2-carboxamide
3-[(4-tert-butylphenyl)sulfonyl]-N-(3-pyridinylmethyl)-1,3-thiazolidine-2-carboxamide
3-[(4-tert-butylphenyl)sulfonyl]-N-[2-(1H-indol-3-yl)-1-methylethyl]-1,3-thiazolidine-2-carboxamide
3-[(4-tert-butylphenyl)sulfonyl]-N-{[1-(4-chlorophenyl)cyclopropyl]methyl}-1,3-thiazolidine-2-carboxamide
3-[(4-tert-butylphenyl)sulfonyl]-N-{4-[3-(dimethylamino)propoxy]benzyl}-1,3-thiazolidine-2-carboxamide
3-{[5-(3-isoxazolyl)-2-thienyl]sulfonyl}-N-{4-[({[(2-phenylethyl)amino]carbonyl}-amino)methyl]benzyl}-1,3-thiazolidine-2-carboxamide ethyl {4-[(3S)-3-({[(2S)-3-([1,1'-biphenyl]-4-ylsulfonyl)-1,3-thiazolidin-2-yl]carbonyl}-amino)-3-phenylpropyl]-1-piperazinyl}acetate
methyl[[(3S)-3-({[(2S)-3-([1,1'-biphenyl]-4-ylsulfonyl)-1,3-thiazolidin-2-yl]carbonyl}-amino)-3-phenylpropyl](methyl)amino]acetate
5 N-(2,2-diphenylethyl)-3-(8-quinolinylsulfonyl)-1,3-thiazolidine-2-carboxamide
N-(2-aminobenzyl)-3-([1,1'-biphenyl]-4-ylsulfonyl)-1,3-thiazolidine-2-carboxamide
N-(3-{[2-(acetylamino)ethyl]amino}-1-phenylpropyl)-3-([1,1'-biphenyl]-4-ylsulfonyl)-1,3-thiazolidine-2-carboxamide
N-(3-amino-1-phenylpropyl)-3-([1,1'-biphenyl]-4-ylsulfonyl)-1,3-thiazolidine-2-carboxamide
N-(3-aminobenzyl)-3-[(4-tert-butylphenyl)sulfonyl]-1,3-thiazolidine-2-carboxamide
N-(3-hydroxy-1-phenylpropyl)-3-[(4-phenoxyphenyl)sulfonyl]-1,3-thiazolidine-2-carboxamide
N-(4-aminobenzyl)-3-[(4-tert-butylphenyl)sulfonyl]-1,3-thiazolidine-2-carboxamide
N-[(1R)-1-benzyl-2-hydroxyethyl]-3-([1,1'-biphenyl]-4-ylsulfonyl)-1,3-thiazolidine-2-carboxamide
N-[(6-amino-3-pyridinyl)methyl]-3-[(4-tert-butylphenyl)sulfonyl]-1,3-thiazolidine-2-carboxamide
N-[1-(1,3-benzodioxol-5-yl)-3-hydroxypropyl]-3-([1,1'-biphenyl]-4-ylsulfonyl)-1,3-thiazolidine-2-carboxamide
N-[1-(1-benzofuran-2-yl)-3-hydroxypropyl]-3-([1,1'-biphenyl]-4-ylsulfonyl)-1,3-thiazolidine-2-carboxamide
N-[1-(2-furyl)-3-hydroxypropyl]-3-[(2'-methyl[1,1'-biphenyl]-4-yl)sulfonyl]-1,3-thiazolidine-2-carboxamide
N-[1-(2-furyl)-3-hydroxypropyl]-3-[(4'-methoxy[1,1'-biphenyl]-4-yl)sulfonyl]-1,3-thiazolidine-2-carboxamide
N-[1-(2-furyl)-3-hydroxypropyl]-3-[(4'-methyl[1,1'-biphenyl]-4-yl)sulfonyl]-1,3-thiazolidine-2-carboxamide
N-[3-(1-azepanyl)-1-phenylpropyl]-3-([1,1'-biphenyl]-4-ylsulfonyl)-1,3-thiazolidine-2-carboxamide
N-[3-(4-acetyl-1-piperazinyl)-1-phenylpropyl]-3-([1,1'-biphenyl]-4-ylsulfonyl)-1,3-thiazolidine-2-carboxamide
N-[3-(4-benzyl-4-hydroxy-1-piperidinyl)-1-phenylpropyl]-3-([1,1'-biphenyl]-4-ylsulfonyl)-1,3-thiazolidine-2-carboxamide N-[3-(acetylamino)-1-phenylpropyl]-3-([1,1'-biphenyl]-4-ylsulfonyl)-1,3-thiazolidine-2-carboxamide N-[3-(benzylamino)-1-phenylpropyl]-3-([1,1'-biphenyl]-4-ylsulfonyl)-1,3-thiazolidine-2-carboxamide N-[4-({[(hexylamino)carbonyl]amino}methyl)benzyl]-3-(phenylsulfonyl)-1,3-thiazolidine-2-carboxamide N-[4-({[(hexylamino)carbonyl]amino}methyl)benzyl]-3-{[5-(3-isoxazolyl)-2-thienyl]sulfonyl}-1,3-thiazolidine-2-carboxamide N-{3-[(1-adamantylmethyl)amino]-1-phenylpropyl}-3-([1,1'-biphenyl]-4-ylsulfonyl)-1,3-thiazolidine-2-carboxamide N-{3-[(2R)-2-(anilinomethyl)pyrrolidinyl]-1-phenylpropyl}-3-([1,1'-biphenyl]-4-ylsulfonyl)-1,3-thiazolidine-2-carboxamide 5 N-{3-[(2S)-2-(anilinomethyl)pyrrolidinyl]-1-phenylpropyl}-3-([1,1'-biphenyl]-4-ylsulfonyl)-1,3-thiazolidine-2-carboxamide N-{3-[benzyl(2-hydroxyethyl)amino]-1-phenylpropyl}-3-([1,1'-biphenyl]-4-ylsulfonyl)-1,3-thiazolidine-2-carboxamide N-{3-[benzyl(methyl)amino]-1-phenylpropyl}-3-([1,1'-biphenyl]-4-ylsulfonyl)-1,3-thiazolidine-2-carboxamide N-{4-[({[(2-ethylhexyl)amino]carbonyl}amino)methyl]benzyl}-3-[(4-iodophenyl)-sulfonyl]-1,3-thiazolidine-2-carboxamide N-benzhydryl-3-([1,1'-biphenyl]-4-ylsulfonyl)-1,3-thiazolidine-2-carboxamide N-benzhydryl-3-(8-quinolinylsulfonyl)-1,3-thiazolidine-2-carboxamide N-benzyl {3-[(4-tert-butylphenyl)sulfonyl]-1,3-thiazolidin-2-yl}methanamine N-benzyl-3-([1,1'-biphenyl]-4-ylsulfonyl)-1,3-thiazolidine-2-carboxamide N-benzyl-3-[(4-tert-butylphenyl)sulfonyl]-1,3-thiazolidine-2-carboxamide tert-butyl 3-{[({3-[(4-tert-butylphenyl)sulfonyl]-1,3-thiazolidin-2-yl}carbonyl)amino]-methyl}phenylcarbamate tert-butyl 5-{2-[({3-[(4-tert-butylphenyl)sulfonyl]-1,3-thiazolidin-2-yl}carbonyl)amino]-ethyl}-2-pyridinylcarbamate (3S)-3-({[(2S)-3-(biphenyl-4-ylsulfonyl)-1,3-thiazolidin-2-yl]carbonyl}amino)-3-(2,6-difluorophenyl)propyl L-valinate (3S)-3-(2,6-difluorophenyl)-3-[({(2S)-3-[(2'-fluorobiphenyl-4-yl)sulfonyl]-1,3-thiazolidin-2-yl}carbonyl)amino]propyl L-valinate (3S)-3-({[(2S-3-(biphenyl-4-ylsulfonyl)-1,3-thiazolidin-2-yl]carbonyl}amino)-3-phenylpropyl L-valinate (3S)-3-[({(2S)-3-[(2'-fluorobiphenyl-4-yl)sulfonyl]-1,3-thiazolidin-2-yl}carbonyl)amino]-3-phenylpropyl L-valinate 3-({[(3S)-3-({[3-(biphenyl-4-ylsulfonyl)-1,3-thiazolidin-2-yl]carbonyl}amino)-3-phenylpropyl]amino}sulfonyl)benzoic acid (2S)—N-[(1S)-1-(2,6-difluorophenyl)-3-hydroxypropyl]-3-[(2'-fluorobiphenyl-4-yl)sulfonyl]-1,3-thiazolidine-2-carboxamide (2S)-3-[(2'-fluorobiphenyl-4-yl)sulfonyl]-N—[(R)-phenyl(pyridin-2-yl)methyl]-1,3-thiazolidine-2-carboxamide (2S)-3-[(2'-fluorobiphenyl-4-yl)sulfonyl]-N—[(S)-(1-methylpiperidin-4-yl)(phenyl)methyl]-1,3-thiazolidine-2-carboxamide 3-(biphenyl-4-ylsulfonyl)-N-[(2-chloropyridin-4-yl)(phenyl)methyl]-1,3-thiazolidine-2-carboxamide 3-(biphenyl-4-ylsulfonyl)-N-[(6-hydroxypyridin-3-yl)(phenyl)methyl]-1,3-thiazolidine-2-carboxamide (2S)-3-[(2'-fluorobiphenyl-4-yl)sulfonyl]-N—[(R)-phenyl(pyridin-4-yl)methyl]-1,3-thiazolidine-2-carboxamide (2S)-3-[(4-iodophenyl)sulfonyl]-N—[(R)-phenyl(pyridin-2-yl)methyl]-1,3-thiazolidine-2-carboxamide 3-(biphenyl-4-ylsulfonyl)-N-[[5-(2-hydroxyethyl)-1,2,4-oxadiazol-3-yl](phenyl)methyl]-1,3-thiazolidine-2-carboxamide 5 methyl 2-methyl-2-(4-{[2-({[(R)-phenyl(pyridin-2-yl)methyl]amino}carbonyl)-1,3-thiazolidin-3-yl]sulfonyl}phenyl)propanoate (2S)-3-(biphenyl-4-ylsulfonyl)-N-[(1S)-1-(4-fluorophenyl)-3-hydroxypropyl]-1,3-thiazolidine-2-carboxamide 3-(biphenyl-4-ylsulfonyl)-N-[(6-chloropyridin-3-yl)(phenyl)methyl]-1,3-thiazolidine-2-carboxamide (2S)-3-(biphenyl-4-ylsulfonyl)-N-{(1S)-3-[methyl(methylsulfonyl)amino]-1-phenyl-propyl}-1,3-thiazolidine-2-carboxamide 3-{[4-(2-fluoro-1,1-dimethylethyl)phenyl]sulfonyl}-N—[(R)-phenyl(pyridin-2-yl)methyl]-1,3-thiazolidine-2-carboxamide (2S)-3-[(4-bromophenyl)sulfonyl]-N—[(R)-phenyl(pyridin-2-yl)methyl]-1,3-thiazolidine-2-carboxamide (3S)-3-phenyl-3-[(f{(2S)-3-[(4-vinylphenyl)sulfonyl]-1,3-thiazolidin-2-yl}carbonyl)amino]-propyl L-valinate 3-(biphenyl-4-ylsulfonyl)-N-[{5-[2-(dimethylamino)ethoxy]pyridin-2-yl}(phenyl)methyl]-1,3-thiazolidine-2-carboxamide 3-(biphenyl-4-ylsulfonyl)-N-[[6-(dimethylamino)pyridin-3-yl](phenyl)methyl]-1,3-thiazolidine-2-carboxamide 3-(biphenyl-4-ylsulfonyl)-N-[phenyl(1-L-valylpiperidin-4-yl)methyl]-1,3-thiazolidine-2-carboxamide Still a further aspect of the present invention is the use of the novel compounds of formula (I) as medicament.

Still a further object of the present invention is a process for preparing 1,3-thiazolidine-2-carboxamide derivatives according to formula (I).

The 1,3-thiazolidine-2-carboxamide derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Generally, the 1,3-thiazolidine-2-carboxamide derivatives of the present invention may be obtained by several synthetic approaches, using both solution-phase and solid-phase chemistry protocols.

According to one process, illustrated in Scheme 1 below, 1,3-thiazolidine-2-carboxamide derivatives according to the general formula (I), whereby $R^1$, $R^2$, $R^4$, G' and n are as above defined, may be prepared from the corresponding carboxylic acid compounds (111), amines (IV), and sulfonyl chlorides (VI), using standard solution-phase chemistry protocols well known to the practitioner skilled in the art. Intermediates of formula V, wherein PG is a suitable N-protecting group (such as Boc, Fmoc, Cbz, and others), can be obtained from the corresponding carboxylic acid compounds (III) and amines (IV) using standard amide coupling conditions well known to the practitioner skilled in the art. Removal of the N-protecting group (e.g., in cases where PG is Boc, using dilute TFA in DCM, or HCl in Dioxane/DCM mixtures), followed by treatment with sulfonylchlorides (VI) in conjunction with a suitable base (such as TEA, DIEA, pyridine, and others), yields products of general formula (I).

Scheme 1

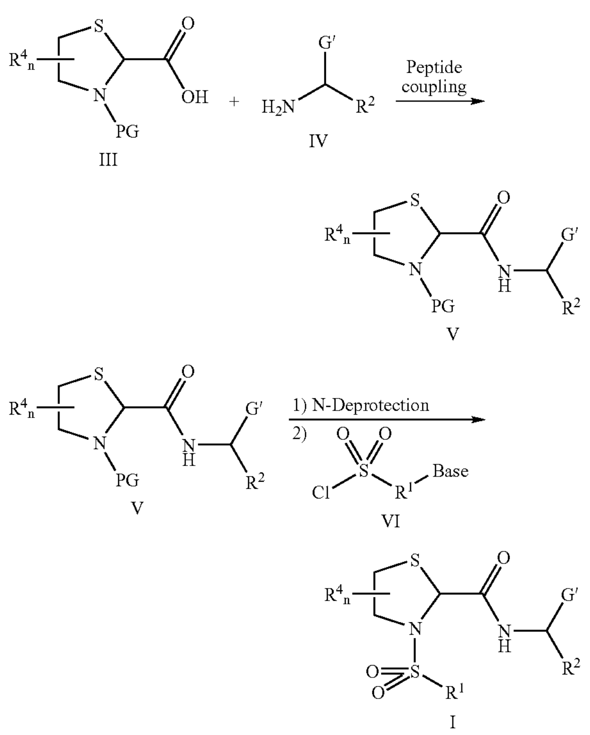

III, IV, V, VI, I

According to another process, illustrated below in Scheme 2,1,3-thiazolidine-2-carboxylic acid derivatives (VII) may be reacted with sulfonyl chlorides (VI), using well known standard solution-phase chemistry protocols, such as e.g. the Schotten-Baumann conditions, affording intermediates of general formula (VIII). The latter can subsequently be reacted with amines (IV) using standard peptide coupling conditions well known to the practitioner skilled in the art, to yield products of general formula (I).

Scheme 2

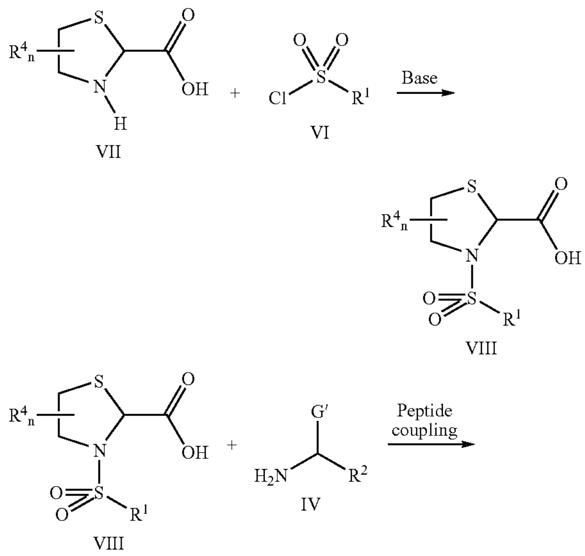

VII, VI, VIII, VIII, IV

-continued

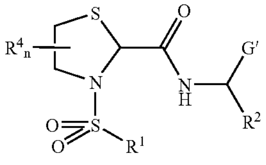

I

According to yet another process, illustrated in Scheme 3, 1,3-thiazolidine-2-carboxylic acid ester derivatives (IX) may be reacted with sulfonyl chlorides (VI), followed by saponification of the ester moiety using standard reagents like NaOH, HCl, Boron tribromide, $KOSi(CH_3)_3$, or others, to allow isolation of the corresponding carboxylic acid intermediates (VIII). The latter are then reacted with amines (IV) using standard amide coupling conditions well known to the practitioner skilled in the art to yield products of general formula (I).

Scheme 3

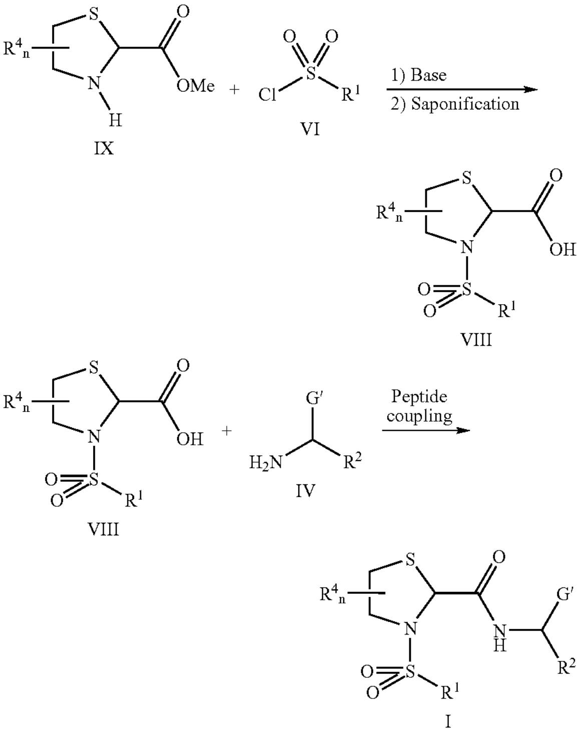

IX, VI, VIII, VIII, IV, I

The racemic 1,3-thiazolidine-2-carboxylic acid derivatives (III), (VII), and (IX) presented in Schemes 1-3 are either obtained from commercial sources, or prepared from commercially available starting materials by standard methods detailed in the literature.

The sulfonyl chlorides (VI) presented in Schemes 1-3, wherein $R^1$ is as above defined, are either commercially available or prepared by standard methods well known to the person skilled in the art, e.g. by treatment of the corresponding sulfonic acids (X) with chlorination agents, such as, e.g., $SO_2Cl_2$, $SOCl_2$, dimethylphosgeniminium chloride, and others, or by treatment of a suitable precursor (XI) with a chlorosulfonylation reagent, such as, e.g. $ClSO_3H$ (see Scheme 4).

Scheme 4

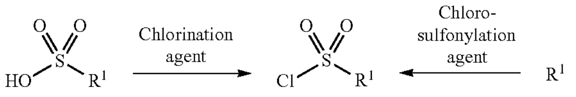

X VI XI

The sulfonic acids (X) and precursors (XI) are either obtained from commercial sources or synthesized from commercial starting materials, using standard methods well known to those skilled in the art, of which some are exemplified in Scheme 5 and described hereinafter in the Examples. Thus, e.g., bromobenzenesulfonates (XII) may be reacted with boronic acids (XIII) in presence of a palladium catalyst to yield the sulfonic acids (X). Alternatively, bromobenzenesulfonates (XII) may be converted into the corresponding sulfonic esters (XIV) by treatment with, e.g., thionyl chloride followed by 2-methyl-1-propanol. Sulfonic esters (XIV) can then be transformed in to the corresponding boronic acid derivatives (XV) using, e.g., triisopropylborate in the presence of n-butyllithium. Palladium(0) catalysed cross-coupling between the boronic acid derivatives (XV) and suitable substituted or unsubstituted aryl or heteroaryl halides affords the desired sulfonic acids (X).

may be obtained using, e.g., the process shown in Scheme 6. Therein, substituted or unsubstituted aromatic or heteroaromatic aldehydes (XVI) are reacted with commercially available aminoalcohols (XVII) to form the corresponding imines (XVIII), followed by addition of a carbanion species (XIX), such as, e.g., a Grignard reagent, organocuprate or organolithium reagents, or others, using standard conditions well known to the person skilled in the art. The resulting secondary amines (XX) can subsequently be converted into the corresponding primary amine analogues (IV) by oxidative cleavage using, e.g., periodic acid, as described hereinafter in the Examples. This process also allows for the obtention of optically pure amines (IV*), by means of using optically active aminoalcohols (XVII*), as described hereinafter in Scheme z.

Scheme 6

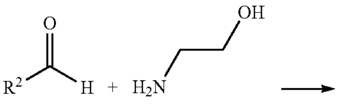

XVI XVII

Scheme 5

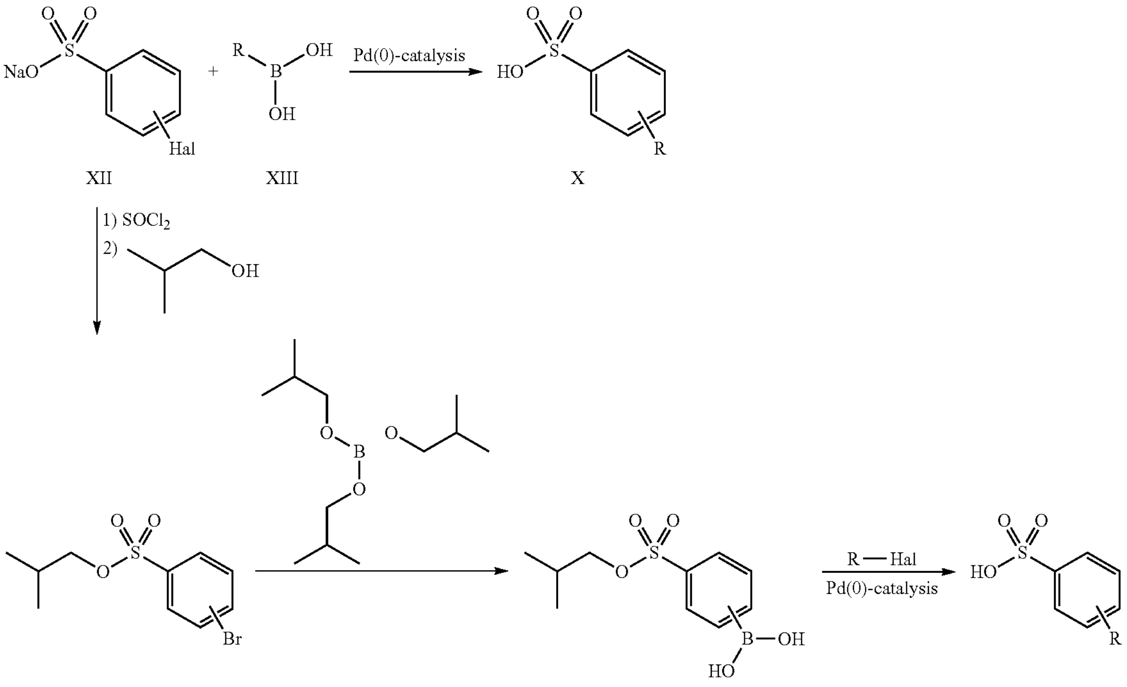

XII XIII X

XIV XV X

[Hal = Cl, Br, J; R = subst. or unsubst. aryl, heteroaryl]

The amine compounds (IV) presented in Schemes 1-3, wherein $R^2$ and G' are as above defined, are either obtained from commercial sources or made from commercial starting materials using standard protocols well known to the person skilled in the art, as shown in the below Schemes and illustrated hereinafter in the Examples.

In those cases where $R^2$ and G' are substituted or unsubstituted aryl or heteroaryl moieties, the amine compounds (IV)

-continued

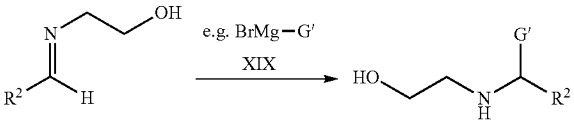

XVIII XX

-continued

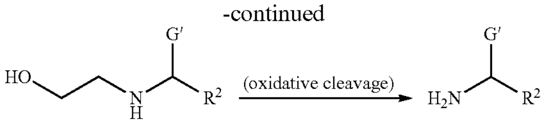

XX IV

[$R^2$ = substituted or unsubstitued aryl or heteroaryl]

The substituted or unsubstituted aryl and heteroaryl aldehydes (XVI or XVI*) are either obtained from commercial sources, or made by one of the numerous pertinent processes detailed in the literature and well known the person skilled in the art. As an exemplification, one such process is shown in Scheme 7 and described hereinafter in the Examples.

Scheme 7

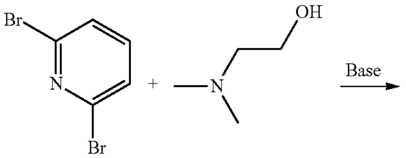

XXI XXII

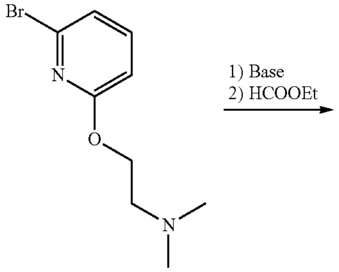

XXIII

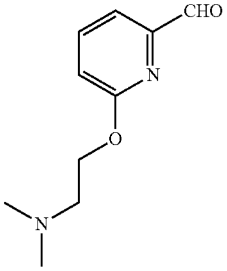

XVI

Others substituted or unsubstituted aryl and heteroaryl aldehydes (XVI*) are either obtained from commercial sources, or made by one of the numerous pertinent processes detailed in the literature and well known the person skilled in the art. As an other exemplification, one such process is shown in Scheme 8 and described hereinafter in the Examples.

Scheme 8

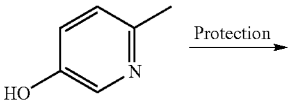

XXI*

-continued

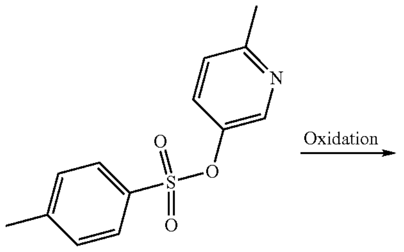

XXII*

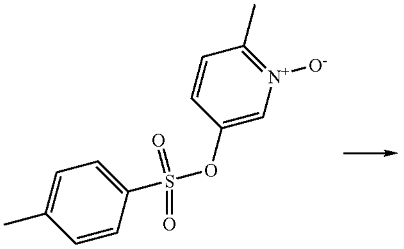

XXIII*

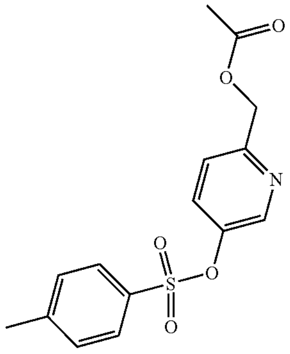

XXIV*

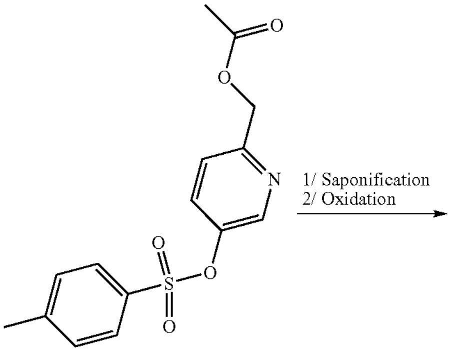

XXIV*

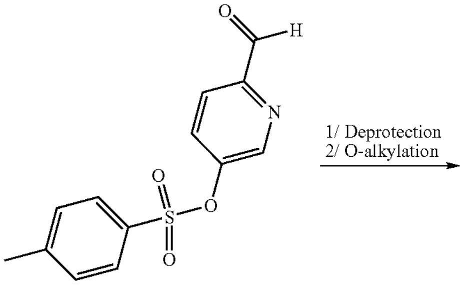

XXV*

-continued

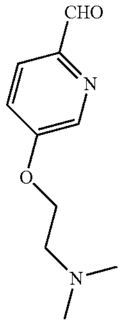

XVI*

In those cases where $R^2$ and G' are substituted or unsubstituted aryl or heteroaryl or heterocyclic moieties, the amine compounds (IV) may be obtained using, e.g., the process shown in Scheme 9. Therein, substituted or unsubstituted aromatic (XVII*) are reacted with acyl chlorides (XVIII*) to form the corresponding ketones (XIX*), or by reaction of substituted or unsubstituted lithiated aromatic (XXXXI*) with nitriles derivatives (XXXXII*). The ketones (XIX*) were then treated with hydroxylamine to give the corresponding oxime (XXXXIII'). Subsequent reduction of the oxime (XXXXIII') with an appropriated reductive agent, using standard conditions well known to the person skilled in the art, allow to access to the amine compounds (IV) as described hereinafter in the Examples.

Scheme 10

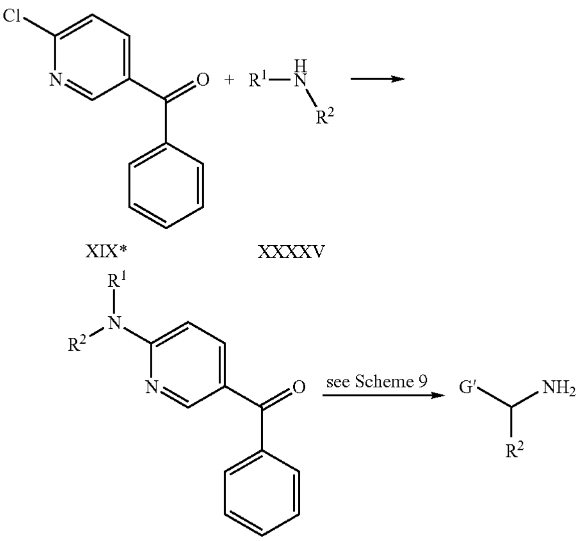

XIX* XXXXV

XXXXVI IV

The amine compounds (IV) presented in Schemes 1-3, in which $R^2$ represents a moiety of the general structure $C_1$-$C_6$-alkyl-A-$R^5$, whereby the substituents A and $R^5$ are as above defined, are either commercially available or may be obtained using, e.g., one of the processes exemplified in Scheme 7-9 and described hereinafter in the Examples. A particularly preferred process consists in the transformation of one functional moiety ($R^2$) into a different one ($R^{2'}$), using any known functional group interconversion protocols. As illustrated in Scheme 11, and described hereinafter in the Examples, these functional group interconversions can be effected on the level of either the free amines (IV, IV'), or the suitably protected amines (XXIV, XXIV'), or the 1,3-thiazolidine-2-carboxam- Scheme 9

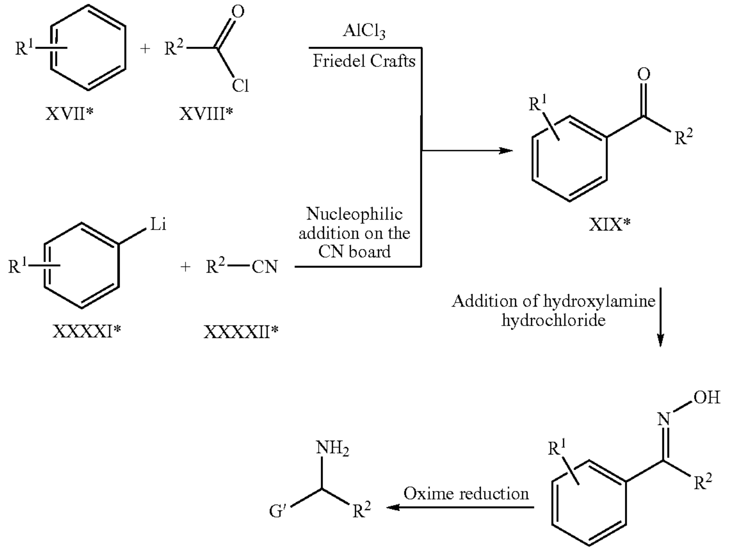

XVII* XVIII* XIX* XXXXI* XXXXII* IV XXXXIII*

[$R^2$ = substituted or unsubstituted aryl or heteroaryl]

The amines (IV) where $R^2$ and G' are substituted or unsubstituted aryl or heteroaryl or heterocyclic moieties, can be obtained from the ketone XIX* as shown below in Scheme 10, by treatment with an appropriate amine (XXXXV) to give compound XXXXVI after nucleophile substitution. Following subsequent treatments as outlined above in Scheme 9, the corresponding amines IV were isolated as pure compounds.

ide compounds (V, V') or (I, I'). The choice of the best synthetic strategy will be governed by the nature of the functional groups to be interconverted, and the compatibility of the required reaction conditions with other functional groups present in the corresponding compounds, as will be well appreciated by the person skilled in the art. Amongst the most preferred starting materials (IV), and the corresponding derivatives (XXIV), (V), and (I), are those wherein $R^2$ is —COOH and/or —$CH_2COOH$, i.e., alpha- and/or beta-amino acids, which are either obtained from commercial sources or made by one of the numerous processes described in the literature. From the intermediates (XXV) derived thereof, in which R is as defined in Scheme 11, a wide range of derivatives, such as e.g. (XXVI)-(XXXVI), in which $R^4$, $R^5$, $R^6$, $R^7$, n, G' and B are as above defined, can be obtained by reaction sequences including oxidations, reductions, O- and N-alkylations, reductive alkylations and aminations, chain-elongations, Mitsunobu reactions, Acylation, debocylation, Wittig reactions, acylations, sulfonylations and any other appropriate transformations leading to functional group interconversions, some of which being exemplified in Scheme 11. The synthetic examples cited in Scheme 11 are meant to illustrate the concept of functional group interconversion as applied to compounds of general structures (IV), (XXIV), (V), and (I), wherein R, $R^2$ and G' are as defined in the above description and in Scheme 11, and are not construed to be viewed as limiting the scope of said synthetic approach.

Scheme 11

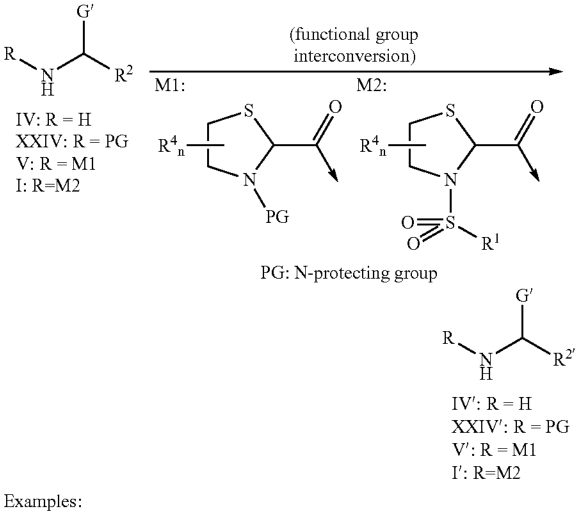

Examples:

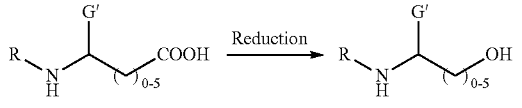

XXV XXVI

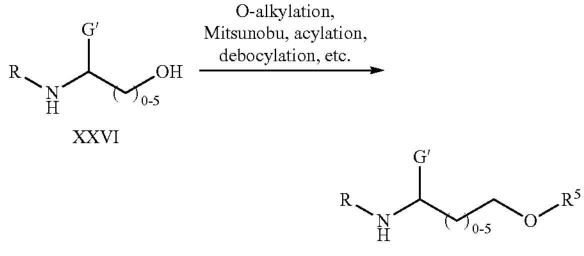

XXVII

-continued

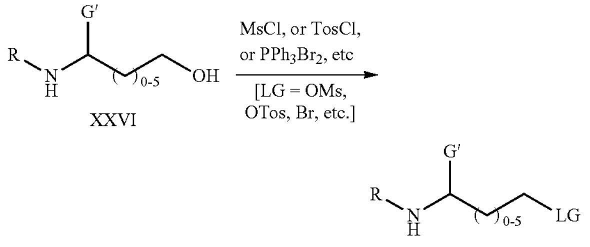

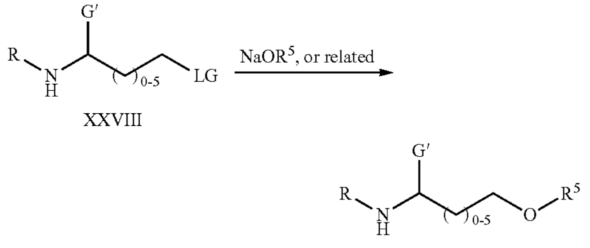

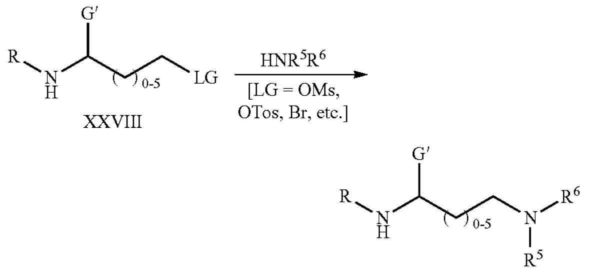

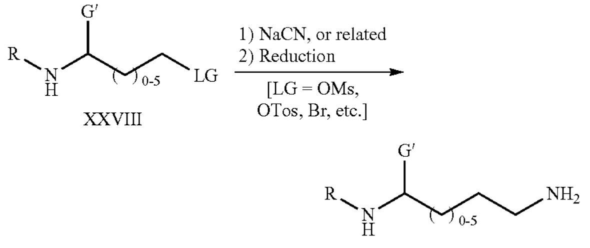

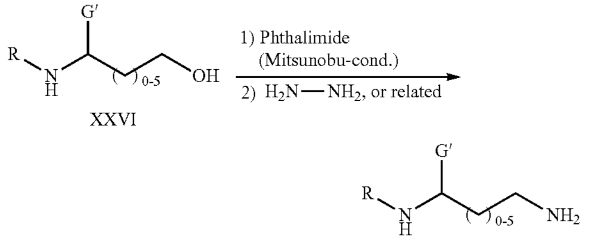

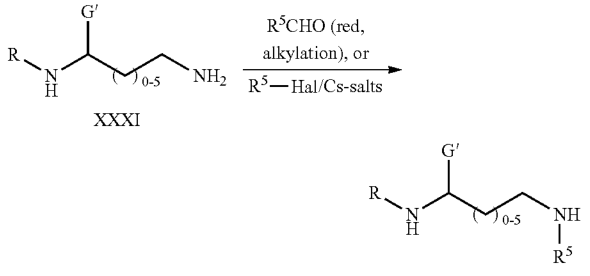

-continued

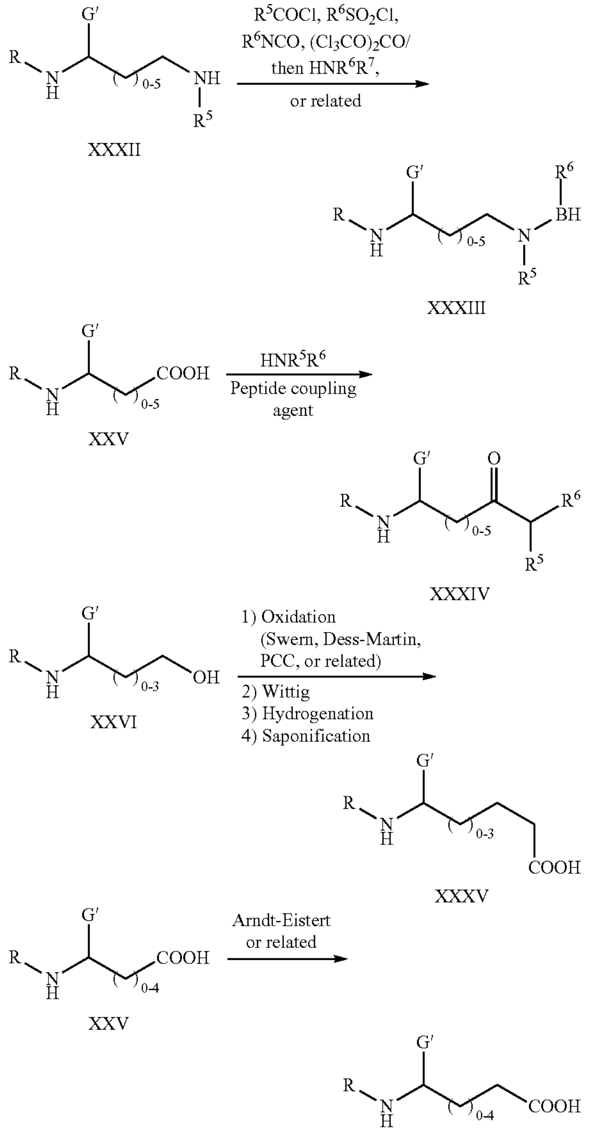

XXXII XXXIII XXV XXXIV XXVI XXXV XXV XXXVI

The processes outlined in the above Schemes, in particular Schemes 1-3, usually afford mixtures of stereoisomers, such as diastereomers and/or enantiomers, when racemic starting materials (III), (IV), (VII), and/or (IX) are used, due to the presence of at least one, most often two, and in some cases three or more, asymmetric carbon atoms in the compounds of general formula (I). Pure stereoisomers can be obtained from the mixtures by current separation methods, including, e.g., flash chromatography, HPLC, crystallization, and others.

According to another process, less complex mixtures of stereoisomers up to pure stereoisomers can be obtained by using the corresponding optically pure starting materials (III*), (IV*), (VII*), and/or (IX*) for the syntheses outlined in the above Schemes, in particular Schemes 1-3. Optically pure amines (IV*) are either obtained from commercial sources or made by current methods known to the person skilled in the art, including stereoselective chemical synthesis, chemical resolution, enzymatic resolution, or combinations thereof, as exemplified in Scheme 12 and in the Examples hereinafter. Thus, optically pure amines (IV*) can be obtained, e.g., by adapting the process outlined in Scheme 6 above, by means of using a chiral auxiliary (XVII*), such as, e.g., valinol or others, which are obtained in optically pure form either from commercial sources or by standard methods described in the literature (Scheme 7-9, Example A). Alternatively, as shown in Scheme 12 (Example B), chiral amines (IV*) may be obtained by enzymatic resolution of appropriate racemic precursors (IV), and subsequently transformed into other chiral amines (IV'*) by standard functional group interconversion methods, such as those outlined in Scheme 11 above. Similarly to the obtention of enantiomerically pure amines (IV*), optically pure 1,3-thiazolidine-2-carboxylic acid derivatives (III*), (VII*), and/or (IX*) can be obtained by stereoselective chemical synthesis, chemical resolution, enzymatic resolution, or combinations thereof. The Examples cited above and shown in Scheme 11 are meant to illustrate the preparation of optically pure starting materials, and are not construed to be viewed as limiting the scope of said synthetic approach.

Scheme 12

Example A: stereoselective synthesis with chiral auxillary

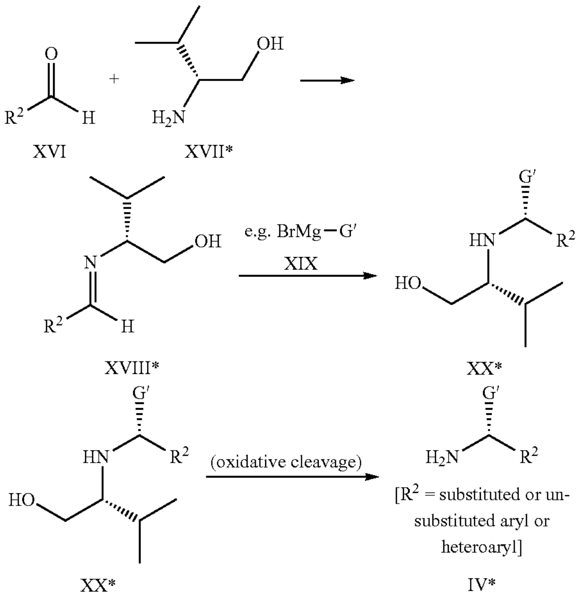

XVI XVII* XVIII* XX* XX* IV*

Example B: enzymatic resolution of racemic starting materials

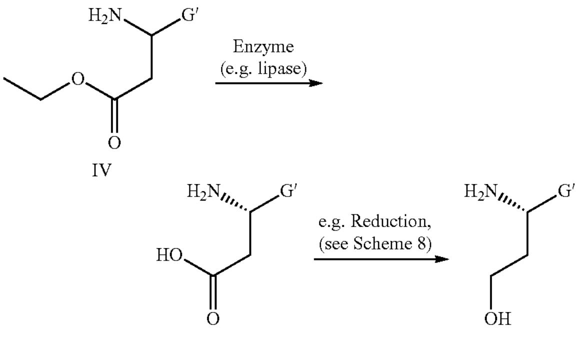

IV IV* IV'*

According to yet another process, illustrated in Scheme 13, the carboxylic acid intermediates (VIII) may be reacted with amines (IV) to lead to the corresponding carboxylic acid intermediate (Ia). The primary amide compound (Ib) was isolated after formation of the anhydride mixture of the carboxylic acid compound (Ia) and treatment with an excess of ammonia. Dehydration of the primary amide (Ib) with cyanuric chloride allow to access to the nitrile derivative (Ic), which was subsequently treated with hydroxylamine to give the amidoxime (Id). The amidoxime intermediate (Id) was then reacted with an appropriated carboxylic acid using standard amide coupling conditions and heated up to allow cyclisation and formation of the final compound oxadiazole using conditions well known to the practitioner skilled in the art to yield products of general formula (I).

Scheme 13

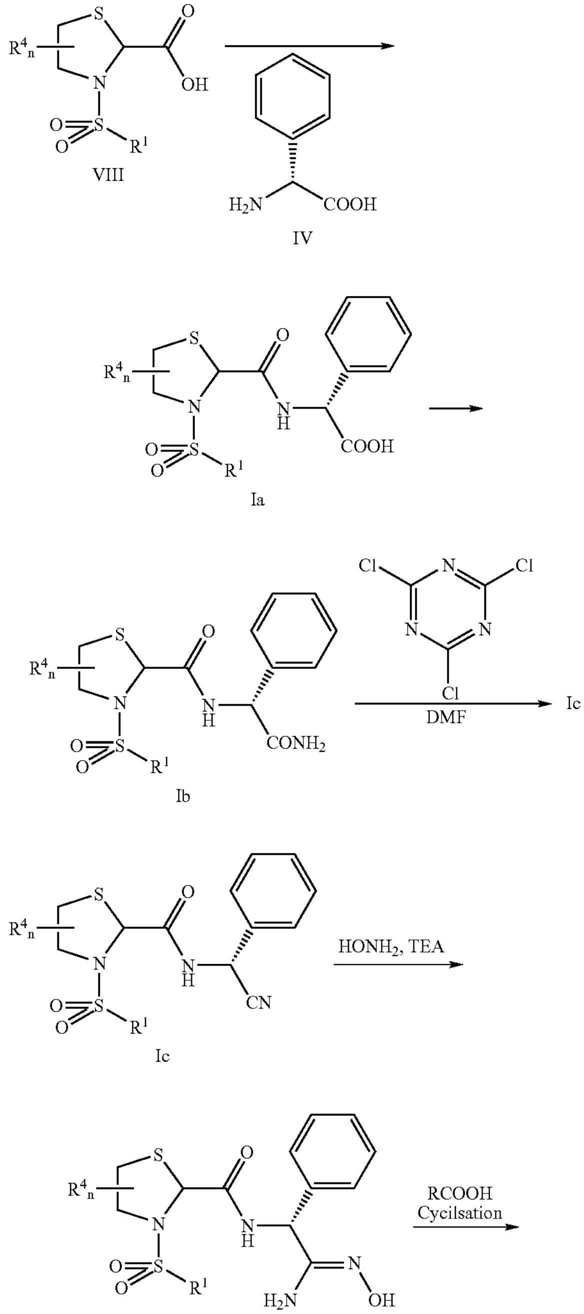

VIII IV Ia Ib Ic Id

-continued

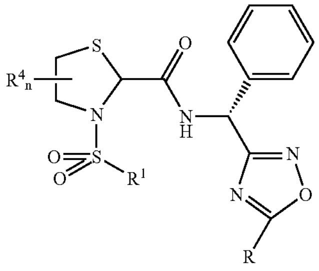

I

The processes hitherto outlined describe the synthesis of 1,3-thiazolidine-2-carboxamide derivatives of general formula (I) by solution-phase methods. According to yet another approach, 1,3-thiazolidine-2-carboxamide derivatives of formula (I), wherein the substituents $R^1$, $R^2$, $R^4$, G' and n are as above defined, are prepared by solid-phase protocols, such as, e.g., that outlined in Schemes 1-12 and described hereinafter in the Examples. Therein, the filled circles symbolize the resin beads to which the corresponding compounds are linked during the solid phase synthesis. Thus, suitably N-protected 1,3-thiazolidine-2-carboxylic acids (III) are reacted, e.g., with Kaiser oxime resin using, e.g., standard carbodiimide-mediated coupling conditions well known to the practitioner skilled in the art, followed by removal of the protecting group. The resulting intermediates are treated with sulfonyl chlorides (VI) in the presence of a base, affording resin-bound intermediates of general formula (XXXIX). In order to obtain the final compounds of general formula (I), the linkage to the resin is cleaved by prolonged treatment with amines (IV) and, in certain cases, low percentages of a weak acid, such as HOAc. Other derivatives of formula (I) are prepared using known modifications to, or variations of, the Scheme 14 reaction sequence. Further to the above mentioned Kaiser oxime resin, other suitable reagents, notably resins, known to a person skilled in the art, could be employed for the solid-phase synthesis of compounds of general formula (I).

Scheme 14

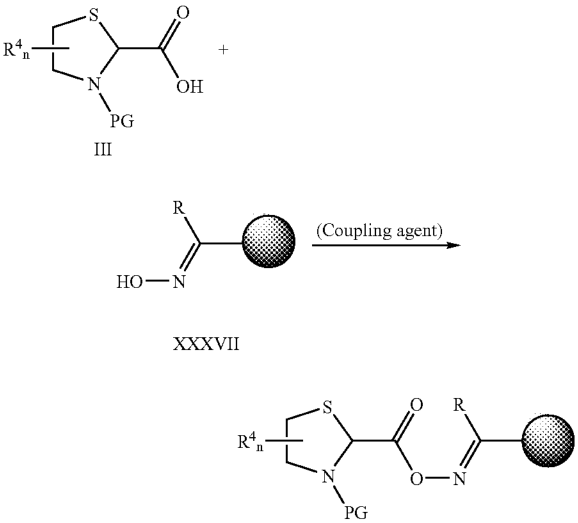

III XXXVII XXXVIII

-continued

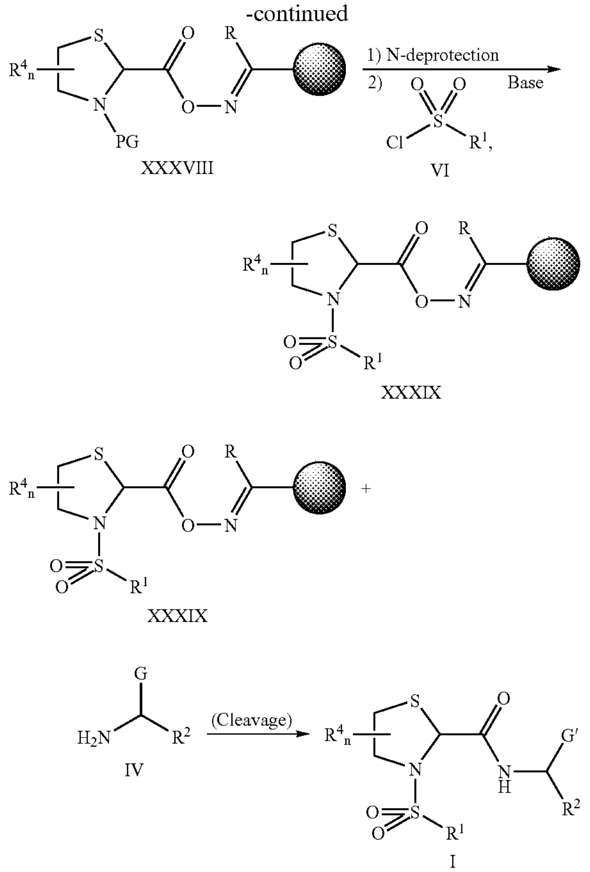

XXXVIII

VI

XXXIX

+

XXXIX

IV

I

If the above set out general synthetic methods are not applicable to obtaining compounds according to formula (I) and/or to necessary intermediates for the synthesis of compounds of formula (I), suitable methods of preparation known by a person skilled on the art should be used. In general, the synthesis pathways for any individual compound of formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, N.Y., 1994 and, Theodora W. Greene and Peter G. M. Wuts in "*Protective Groups in Organic Synthesis*", Wiley-Interscience, 1991.

Compounds of this invention can be isolated in association with solvent molecules by crystallization from evaporation of an appropriate solvent. The pharmaceutically acceptable acid addition salts of the compounds of formula II, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salts may be formed or interconverted using ion-exchange resin techniques.

A final aspect of the present invention are intermediate compounds of the formula (Va)—wherein G' is a phenyl—as used in the method illustrated in Scheme 1, in particular for preparing compounds of formula (Ia).

Va

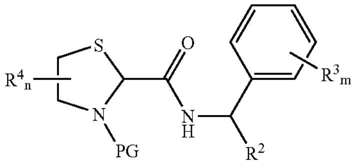

In said formula (Va), PG is H, $R^2$, $R^3$, $R^4$, m and n are as defined above, with the proviso, though, that $R^2$ may not be a hydrogen.

Also intermediate compound of the formula (VIII) are comprised by the present invention,

VIII

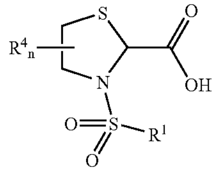

wherein $R^1$ is a 1,1'-biphenyl or a tert-butyl phenyl moiety and $R^4$ and n are as above defined.

When employed as pharmaceuticals, thiazolidine carboxamide derivatives of the present invention are typically administered in the form of a pharmaceutical composition. Hence, pharmaceutical compositions comprising a compound of formula (II) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing thiazolidine carboxamide derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the thiazolidine carboxamide derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the thiazolidine carboxamide derivatives of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences,* 17*th* Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences.*

In the following the present invention shall be illustrated by means of some examples which are not construed to be viewed as limiting the scope of the invention. The following abbreviations are hereinafter used in the accompanying examples: min (minute), hr (hour), g (gram), mmol (millimole), m.p. (melting point), eq (equivalents), ml (milliliter), µl (microliters), ACN (acetonitrile), Boc (butoxycarbonyl), Cbz (carboxybenzyl), $CDCl_3$ (deuterated chloroform), cHex (cyclohexanes), dba (dibenzylidene acetone), DCM (dichloromethane), DEAD (diethylazodicarboxylate, DIC (diisopropyl carbodiimide), DIEA (diisopropyl ethylamine), DMAP (4-dimethylaminopyridine), DMF (dimethylformamide), DMSO (dimethylsulfoxide), DMSO-$d_6$ (deuterated dimethylsulfoxide), EDC (1-(3-dimethylaminopropyl)-3-ethylcarbodiimide hydrochloride), EtOAc (ethyl acetate), $Et_2O$ (diethyl ether), Fmoc (9-fluorenylmethoxycarbonyl), HOBt (1-hydroxybenzotriazole), $K_2CO_3$ (potassium carbonate), $MgSO_4$ (magnesium sulfate), MsCl (methylsulfonyl chloride), MTBE (tert-butyl methyl ether), NaH (sodium hydride), $NaHCO_3$ (sodium bicarbonate), nBuLi (n-butyllithium), PCC (pyridinium chlorochromate), PetEther (petroleum ether), QCl (tetrabutylammonium chloride), rt (room temperature), TBTU (O-benzotriazolyl-N,N,N',N'-tetramethyluronium-tetrafluoroborate), TEA (triethyl amine), TFA (trifluoroacetic acid), THF (tetrahydrofuran), TMOF (triethylorthoformate), TMAD (N,N,N',N'-tetramethylazodicarboxamide), TosCl (toluenesulfonyl chloride).

EXAMPLES

Intermediate 1: Preparation of Amines of General Formula (IV)/(IV*); e.g., (R)-phenyl(2-pyridinyl)methanamine

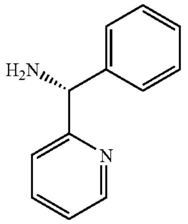

Method A:

a) Protocol for the formation of the imine intermediates (XVIII)/(XVIII*); e.g. (2R)-3-methyl-2-{[(E)-2-pyridinylmethylidene]amino}-1-butanol

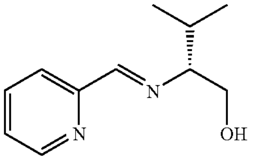

Anhydrous $MgSO_4$ (50 g, 415 mmol, 4.15 eq) and a substituted aryl or heteroaryl carboxaldehyde, e.g. 2-pyridinecarboxaldehyde (9.5 ml, 100 mmol, 1 eq), were added to a solution of (R)-(−)-2-amino-3-methyl-1-butanol (10.32 g, 100 mmol) in dry DCM (150 ml) at 0° C. The reaction was followed by LC/MS. The mixture was stirred at this temperature for 2 h 25. $MgSO_4$ was filtered off and the DCM removed by evaporation to give the desired product (XVIII*), e.g. (2R)-3-methyl-2-{[(E)-2-pyridinylmethylidene]amino}-1-butanol as a yellowish oil (19.23 g, quantitative yield).

$^1H$ NMR (300 MHz, DMSO); Major tautomer: 0.88 (m, 6H, $CH(CH_3)_2$); 1.88 (m, 1H, $CH(CH_3)_2$); 3.03 (m, 2H); 3.66 (m, 1H); 4.51 (t, J=6.0 Hz, 1H); 7.43 (m, 1H); 7.85 (m, 1H); 7.96 (m, 1H); 8.23 (s, 1H); 8.62 (m, 1H). $M^+(ESI^+)$: 193.

b) Protocol for the silylation of intermediates (XVIII)/(XVIII*); e.g. (2R)-3-methyl-N—[(E)-2-pyridinylmethylidene]-1-[(trimethylsilyl)oxy]-2-butanamine

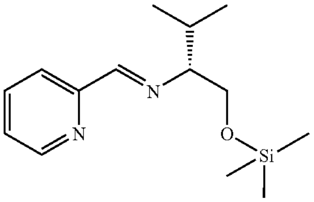 [SMILES: CC(C)[C@H](CO[Si](C)(C)C)/N=C/c1ccccn1]

The imine (XVIII*) resulting from the precedent step, e.g. (2R)-3-methyl-2-{[(E)-2-pyridinylmethylidene]amino}-1-butanol (100 mmol) was dissolved in dry DCM (100 ml). TEA (15.3 ml, 110 mmol, 1.1 eq) and chlorotrimethylsilane (13.9 ml, 110 mmol, 1.1 eq) was added to the stirred solution. The reaction was followed by LC/MS. After 2 h 30, the reaction was complete. The solvent was removed in vacuo and the residue was taken up in 500 ml $Et_2O$-Cyclohexane (1:1) and the solid phase was filtered off. The organic solution was concentrated in vacuo to give the desired product, e.g.

(2R)-3-methyl-N—[(E)-2-pyridinylmethylidene]-1-[(trimethylsilyl)oxy]-2-butanamine as a yellowish oil (25.5 g, 96%).

$^1$H NMR (300 MHz, $CDCl_3$); 0.0 (s, 9H, $Si(CH_3)_3$); 0.89 (s, 6H, $CH(CH_3)_2$); 1.93 (m, 1H, $CH(CH_3)_2$); 3.03 (m, 1H); 3.63 (m, 1H); 3.83 (m, 1H); 7.25 (m, 1H); 7.68 (m, 1H); 8.0 (m, 1H); 8.26 (s, 1H); 8.60 (m, 1H). $M^+(ESI^+)$: 265.

c) Asymmetric addition of Grignard reagents; e.g., (2R)-3-methyl-2-{[(R)-phenyl(2-pyridinyl)methyl]amino}-1-butanol (XX)/(XX*)

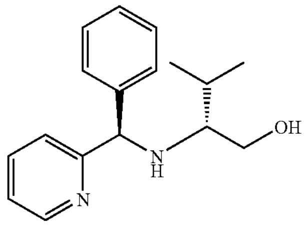 [SMILES: CC(C)[C@H](CO)N[C@H](c1ccccc1)c1ccccn1]

The silylated imine from the previous step, e.g. (2R)-3-methyl-N—[(E)-2-pyridinylmethylidene]-1-[(trimethylsilyl)oxy]-2-butanamine was dissolved in dry THF (500 ml) and the solution was cooled down to −78° C. A 1 M solution of phenylmagnesiumbromide in THF (200 ml, 200 mmol, 2 eq) was added dropwise while the mixture was stirred by a magnetic bar. The mixture was further stirred 2 hours at −78° C. The temperature was then slowly increased up to room temperature overnight. A sample of the reaction mixture was quenched with aqueous $NaHCO_3$ and analysed by LC-MS to detect the O-silylated products. After one night, the mixture was quenched with HCl 1M (250 ml) and the mixture was stirred at room temperature until the desilylation was complete (after 1 h, LC/MS analysis). The aqueous phase was further acidified with the addition of 5M HCl solution (20 ml). The aqueous phase was washed with 300 ml cyclohexane/$Et_2O$ (2:1), then made basic with 60 ml NaOH 5M at 0° C., and the organic products were extracted with $Et_2O$, dried ($MgSO_4$) and concentrated to give the desired product (XX*), e.g. (2R)-3-methyl-2-{[(R)-phenyl(2-pyridinyl)methyl]amino}-1-butanol as a yellowish oil (22.9 g, 85% yield, d.e.=99%, determined by $^1$H NMR).

$^1$H NMR (300 MHz, $CDCl_3$); 0.81 (m, 6H, $CH(CH_3)_2$); 1.76 (m, 1H, $CH(CH_3)_2$); 2.29 (m, 1H); 2.72 (br s, 2H); 3.23-3.60 (m, 2H, $CH_2OH$); 4.87 (d, 1H, $NCHAr_2$); 6.97 (m, 2H, H arom.); 7.17 (m, 5H, H arom.); 7.41 (m, 1H, H arom.); 8.42 (s, 1H, H arom. major diastereomer, 99.5%), 8.70 (s, 1H, H arom. minor diastereomer, 0.5%). $M^+(ESI^+)$: 271.

d) Protocol for the deprotection of the amines (XX)/(XX*); e.g., (R)-phenyl(2-pyridinyl)methanamine

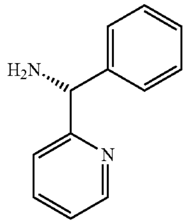

To a solution of the secondary amines (XX)/(XX*) resulting from the preceding step, e.g. (2R)-3-methyl-2-{[(R)-phenyl(2-pyridinyl)methyl]amino}-1-butanol (2.9 g, 10.73 mmol) in 25 ml MeOH/THF (9/1) was added methylamine 40% in water (10.2 ml, 118 nmol, 11 eq). Aqueous periodic acid (8.3 g in 25 ml of water) was added slowly at 0° C. to the stirring solution. This thick solution was allowed to stir at room temperature overnight. The reaction was followed by LC/MS. After one night, water (25 ml) was added, the mixture was filtered and the amine extracted 3 times with $Et_2O$. The organic phase was then dried with $MgSO_4$ and evaporated to give the desired products (IV)/(IV*), e.g. (R)-phenyl(2-pyridinyl)methanamine as a yellowish oil (2.1 g, 95% yield). This crude primary amine was used without further purification.

$^1$H NMR (300 MHz, $CDCl_3$); 2.19 (br s, 2H, $NH_2$); 5.26 (m, 1H, $NCHAr_2$); 7.15-7.44 (m, 7H, H arom.); 7.62 (m, 111, H arom.); 8.58 (s, 1H, H arom.). $M^+(ESI^+)$: 185.

Method B:

a) Protocol for the formation of the aldehyde intermediates (XVI*); e.g., 5-[2-(dimethylamino)ethoxy]pyridine-2-carboxaldehyde (Scheme 8)

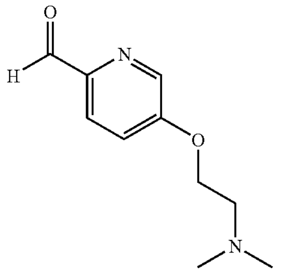

A mixture of 3-hydroxy-6-methylpyridine (57.5 g, 0.529 mol), 4-tosylchloride (110 g, 0.58 mol) and TEA (100 mL) in dry DMF (400 mL) was heated at 110° C. under $N_2$ for 16 h. The reaction mixture was cooled down to RT, diluted with water (3 L). The resulting precipitate was filtered, washed and dried to give crude [3-(4-tosyloxy)]-6-methylpyridine (102 g, 75%) as a white solid. The crude product was used in next reaction without any purification.

To a solution of [3-(4-tosyloxy)]-6-methylpyridine (100 g, 0.38 mol) in dry $CHCl_3$ (2 L) was added MCPBA (50% w/w, 200 g, 0.57 mol) in one portion. The reaction mixture was refluxed for 4 h, cooled to RT and filtered off the solid. The filtrate was washed with 20% $Na_2CO_3$ solution (3×1 L), dried over $Na_2SO_4$ and concentrated to give 6-methyl-3-(4-tosyloxy)pyridine-N-oxide (85 g, 80%) as a solid. The crude product was used in the next step without further purification.

To a solution of acetic anhydride (500 mL) heated at 90° C., was added 6-methyl-3-(4-tosyloxy)pyridine-N-oxide (80 g) in small portions over a period of 2 h. The reaction mixture was refluxed for 16 h under $N_2$. Acetic anhydride was distilled off. The resulting crude product was purified by column chromatography over silica gel (gradient petroleum ether/$CH_2Cl_2$, 7:3 to 3:7) to give 3-tosyloxy-6-acetoxymethylpyridine (55 g, 57%) as a liquid.

A mixture of 3-tosyloxy-6-acetoxymethylpyridine (50 g, 0.148 mol) and NaOH (25 g, 0.62 mol) in 150 mL of water was refluxed for 15 h. The reaction mixture was cooled to RT and neutralized with con. HCl. The solvent was evaporated under vacuum affording a solid residue, which was suspended in ethyl acetate (750 mL) and heated to 60° C. for 30 min. with stirring. The suspended material was filtered off and the filtrate was concentrated to give 5-hydroxy-2-hydroxymethylpyridine (15 g, 80%) as a pale yellow solid. It was used in next step without further purification.

A mixture of 5-hydroxy-2-hydroxymethylpyridine (14 g) and $MnO_2$ (100 g) in isopropylalcohol (600 mL) was stirred under $N_2$ for 20 h. The reaction mixture was filtered and filtrate concentrated under vacuum affording a crude product as a solid (12 g). It was suspended in acetone/acetonitrile (25 mL each) and the solid residue was filtered off. It was washed with cold acetone/acetonitrile 1:1 mixture to give pure 5-hydroxypyridine-2-carboxaldehyde (3 g) as a solid.

A mixture of the above 5-hydroxypyridin-2-carboxaldehyde (4 g, 0.032 mol), $K_2CO_3$ (14 g, 0.097 mol) in THF (100 mL) was heated at 60° C. for 2 h under $N_2$. 2-Dimethylaminoethylchloride was freshly prepared from the corresponding HCl salt (9.4 g, 0.06 mol) to which was added drop-wise 20% NaOH solution (2 equivalent) at 0° C. it was then added drop-wise to the above reaction mixture at 60° C. The reaction mixture was allowed to stir 6 h at the same temperature. Upon completion, the reaction mixture was cooled down to RT, the solid was filtered off and the filtrate was concentrated under vacuum to give expected crude product. It was then purified by column chromatography over silica gel (gradient methanol in chloroform from 0.1% to 2%) to give the desired aldehyde (XVI*), e.g., 5-[2-(dimethylamino)ethoxy]pyridine-2-carboxaldehyde (3.25 g, 51%) as a colorless liquid.

b) Protocol for the preparation of the amines (IV and IV*); e.g., [2-({6-[(R)-amino(phenyl)methyl]pyridin-3-yl}oxy)ethyl]dimethylamine

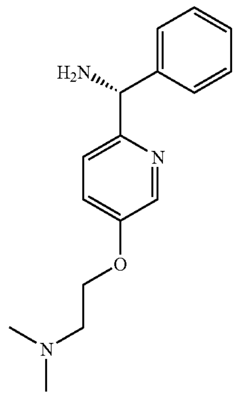 [SMILES: CN(C)CCOc1ccc([C@H](N)c2ccccc2)nc1]

Steps a) to d) described in method A were applied to the aldehyde (XVI*) from the previous step, e.g., 5-[2-(dimethylamino) ethoxy]pyridine-2-carboxaldehyde, affording the desired amine (IV, IV*), e.g., [2-({6-[(R)-amino(phenyl)methyl]pyridin-3-yl}oxy)ethyl]dimethylamine (165 mg, 96% yield). This crude primary amine was used without further purification.

$M^+(ESI^+)$: 271.

Intermediate 2: Preparation of racemic amines of general formula (IV); e.g., [(6-chloropyridin-3-yl)(phenyl)methyl]amine; [(2-chloropyridin-4-yl)(phenyl)methyl]amine; 5-[amino(phenyl)methyl]pyridin-2-ol; 5-[amino(phenyl)-methyl]-N,N-dimethylpyridin-2-amine; [(1-methylpiperidin-4-yl)((phenyl)methyl]amine.

Method A:

a) Protocol for the formation of the ketone intermediates (XIX*); e.g., (6-chloropyridin-3-yl)(phenyl)methanone

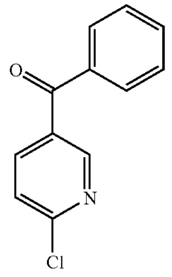 [SMILES: O=C(c1ccccc1)c1ccc(Cl)nc1]

A carboxylic acid, e.g., 6-Chloronicotinic acid (3.151 g, 20 mmol) was dissolved in dry DCM. The mixture was cooled down to 0° C. Oxalyl chloride (2.58 mL, 30 mmol) followed by DMF (77 μL) were added. The mixture was stirred at 0° C. for 1 h 30, then at RT overnight. The solvents were evaporated. The crude product was dissolved in toluene and the solvents were evaporated again to give the corresponding acid chloride (XVIII*), e.g., 6-chloronicotinoyl chloride (2.886 g, 82% yield). It was dissolved in benzene (50 mL) and $AlCl_3$ (5.248 g, 39.4 mmol) was added. The mixture was stirred overnight at 80° C. After cooling down to RT, water was added. The two phases were separated and the aqueous layer was extracted with two portions of ethyl acetate. Combined organic layers were washed with brine and dried over $MgSO_4$, filtrated and concentrated to give the desired product (XIX*), e.g., (6-chloropyridin-3-yl)(phenyl)methanone as a yellowish oil (3.884 g, 67% yield). It was used in the next step without further purification.

$^1H$ NMR (300 MHz, $CDCl_3$); 7.41-7.57 (m, 3H, H arom.); 7.64 (m, 1H, H arom.); 7.73-7.83 (m, 2H, H arom.); 8.08 (dd, J=3.0, 9.0 Hz, 1H, H pyridine.); 8.76 (d, J=3.0 Hz, 1H, H pyridine). $M^+(ESI^+)$: 218.

b) Protocol for the formation of the oxime intermediates (XXXXIII*); e.g., (6-chloropyridin-3-yl)(phenyl)methanone oxime

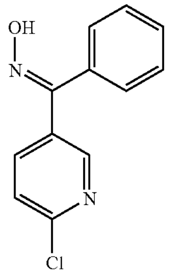 [SMILES: O/N=C(\c1ccccc1)c1ccc(Cl)nc1]

The ketone issued from the precedent step (XIX*), e.g., (6-chloropyridin-3-yl)(phenyl)methanone (435 mg, 2 mmol), was dissolved in EtOH (40 mL). DIEA (1.027 mL, 6 mmol) and hydroxylamine hydrochloride (417 mg; 6 mmol) were added. The mixture was heated under reflux overnight. The solvents were removed. The resulting crude mixture was dissolved in ethyl acetate (40 mL) and was washed with three portions of water. The organic layer was dried over magnesium sulfate, filtrated and evaporated to give the desired product (XXXXIII*), e.g., (6-chloropyridin-3-yl)(phenyl)methanone oxime (413 mg, 89% yield). It was used in the next step without further purification.

$^1H$ NMR (300 MHz, $CDCl_3$); 7.22-7.52 (m, 6H, H arom.); 7.75 (m, 1H, H arom.); 8.45 (d, J=3.0 Hz, 1H, H pyridine). $M^+(ESI^+)$: 233. $M^-(ESI^-)$: 231.

c) Protocol for the reduction of the oxime into the primary amine intermediates (IV); e.g., [(6-chloropyridin-3-yl)(phenyl)methyl]amine

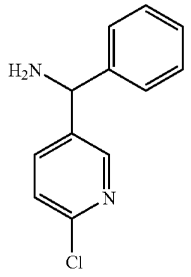 [SMILES: NC(c1ccccc1)c1ccc(Cl)nc1]

The oxime obtained from the precedent step (XIX*), e.g., (6-chloropyridin-3-yl)(phenyl)methanone oxime (368 mg, 1.58 mmol) was dissolved in glacial acetic acid (20 mL). Metallic Zn (1.034 g, 15.8 mmol) was added in portions at RT. The reaction was followed by LC-MS. After a complete reduction of the oxime functionality, the reaction mixture was filtered and the solvents were evaporated. The crude residue was dissolved in DCM and was washed with three portions of $NaHCO_3$ sat. It was then dried over $MgSO_4$, filtrated and evaporated. It was further purified by column chromatography over silica gel (DCM/MeOH 20:1 with 2% of $NH_4OH$) to give the desired product (IV), e.g., [(6-chloropyridin-3-yl)(phenyl)methyl]amine (188 mg, 54% yield).

$^1$H NMR (300 MHz, $CDCl_3$); 5.18 (s, 1H, $CHNH_2$); 7.14-7.32 (m, 6H, H arom.); 7.61 (dd, J=3.0, 6.0 Hz, 1H, H pyridine.); 8.37 (d, J=3.0 Hz, 1H, H pyridine). $M^+(ESI^+)$: 219.

Method B:

a) Protocol for the aromatic substitution of intermediates (XIX*); e.g., (6-chloropyridin-3-yl)(phenyl)methanone with sodium alcolate, affording ketone intermediates (XIX*) e.g., (6-tert-butoxypyridine-3-yl)(phenyl)methanone

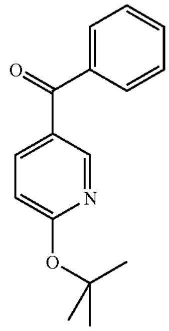 [SMILES: CC(C)(C)Oc1ccc(C(=O)c2ccccc2)cn1]

b) In a 5 mL flask for microwave reaction were added NaH 55-65% in oil (192 mg, 4.4 mmol) and dry THF (2 mL), followed by the alcohol, e.g., t-butanol. The mixture was heated 30 min at 60° C. Intermediates (XIX*); e.g., (6-chloropyridin-3-yl)(phenyl)-methanone (435 mg, 2 mmol) was dissolved in dry THF (2 mL) and added to the alcoholate solution prepared previously. This mixture was heated 40 min under microwave at 100° C. As the reaction was complete, water and ethyl acetate were added. The phases were separated and the aqueous phase was extracted with two portions of ethyl acetate. Combined organic layers were dried over $MgSO_4$, filtrated and evaporated affording the expected product (XIX*), e.g., (6-tert-butoxypyridine-3-yl)(phenyl)methanone (191 mg, 37% yield).

$^1$H NMR (300 MHz, $CDCl_3$); 1.62 (s, 9H, tBu); 6.72 (d, J=6.0 Hz, 1H, H arom.); 7.42-7.53 (m, 2H, H arom.); 7.58 (m, 1H, H arom.); 7.71-7.80 (m, 2H, H arom.); 8.05 (dd, J=3.0, 9.0 Hz, 1H, H pyridine.); 8.37 (d, J=3.0 Hz, 1H, H pyridine). $[M-tBu+H]^+(ESI^+)$: 200. $M^-(ESI^-)$: 255.

c) Protocol for the preparation of the primary amine intermediates (IV); e.g., 5-[amino(phenyl)methyl]pyridin-2-ol

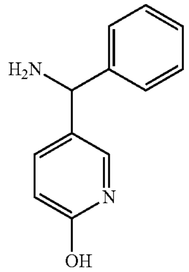 [SMILES: NC(c1ccccc1)c1ccc(O)nc1]

The protocol described in Method A step b) and c) was applied to the intermediate (XIX*); e.g. (6-tert-butoxy-pyridine-3-yl)(phenyl)methanone, affording the desired amine (IV), e.g., 5-[amino(phenyl)methyl]pyridin-2-ol (160 mg, quantitative yield). During the reduction step with Zn in AcOH, the t-butyl group has been cleaved, affording directly the corresponding pyridin-2-ol. This crude primary amine was used without further purification.

$M^+(ESI^+)$: 201.

Method C:

d) Protocol for the aromatic substitution of intermediates (XIX*); e.g., (6-chloropyridin-3-yl)(phenyl)methanone with amine, affording ketone intermediates (XLX*); e.g., (6-N,N-dimethylaminopyridin-3-yl)(phenyl)methanone

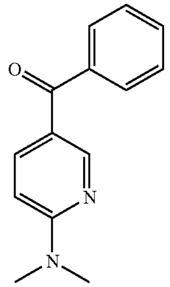 [SMILES: CN(C)c1ccc(C(=O)c2ccccc2)cn1]

In a 5 mL flask for microwave reaction, intermediates (XIX*); e.g., (6-chloropyridin-3-yl)(phenyl)methanone (217 mg, 1 mmol) was added together with dry THF (1.5 mL) and 2M solution of dimethylamine in THF (3 mL, 6 eq). This mixture was heated 120 min under microwave at 180° C. As the reaction was complete, water was added. The aqueous solution was basified with NaOH 5M to pH 8. It was then extracted with three portions of ethyl acetate. Combined organic phases were dried over $MgSO_4$, filtrated and evaporated, affording the expected product (XXXXVI), e.g., (6-N,N-dimethylaminopyridin-3-yl)(phenyl)methanone (88 mg, 39% yield).

$^1$H NMR (300 MHz, $CDCl_3$); 3.19 (s, 6H, $NMe_2$); 6.56 (d, J=9.0 Hz, 1H, H arom.); 7.40-7.49 (m, 2H, H arom.); 7.53 (m, 1H, H arom.); 7.68-7.76 (m, 2H, H arom.); 8.04 (dd, J=3.0, 9.0 Hz, 1H, H pyridine.); 8.60 (d, J=3.0 Hz, 1H, H pyridine). $M^+(ESI^+)$: 227.

e) Protocol for the preparation of the primary amine intermediates (IV); e.g., 5-[amino(phenyl)methyl]-N,N-dimethylpyridin-2-amine

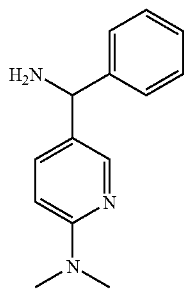 [SMILES: CN(C)c1ccc(C(N)c2ccccc2)cn1]

The protocol described in Method A step b) and c) was applied to the intermediate (XXXXVI); e.g., (6-N,N-dimethylaminopyridin-3-yl)(phenyl)methanone, affording the desired amine (IV), e.g., 5-[amino(phenyl)methyl]-N,N-dimethylpyridin-2-amine (136 mg, 83% yield). This crude primary amine was used without further purification.

$^1$H NMR (300 MHz, $CDCl_3$); 2.13 (br s, 2H, $NH_2$); 2.99 (s, 6H, $NMe_2$); 5.06 (s, 1H, $CHNH_2$), 6.41 (d, J=9.0 Hz, 1H, H arom.); 7.10-7.41 (m, 6H, H arom.); 8.09 (d, J=3.0 Hz, 1H, H pyridine). $M^+$(ESI$^+$): 228.

Method D:

a) Protocol for boc protection of the amino ketone intermediates (XIX*); e.g., phenyl(piperidin-4-yl)methanone

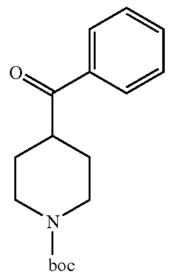

b) The amino ketone intermediate XIX*, e.g. phenyl(piperidin-4-yl)methanone hydrochloride (1.129 g, 5 mmol) was suspended in DCM (25 mL). DIEA (0.94 mL, 5.5 mmol) was added and the resulting inhomogeneous mixture was cooled down to 0° C. Di-tert-butyl dicarbonate (1.20 g, 5.5 mmol) was added as a solid. The mixture was stirred 5 min at 0° C. and 1 h at RT. As the reaction was complete, it was washed with HCl 1N aqueous solution then with $NaHCO_3$ sat, brine and dried over $MgSO_4$. After filtration and evaporation, the expected product (XIX*), e.g., tert-butyl 4-benzylpiperidine-1-carboxylate (1.333 g, 92% yield) was obtained as a white solid.

$^1$H NMR (300 MHz, $CDCl_3$); 1.44 (s, 9H, Boc); 1.59-1.76 (m, 2H); 1.76-1.88 (m, 2H), 2.87 (m, 2H); 3.38 (m, 1H); 4.14 (m, 2H); 7.41-7.49 (m, 2H, H arom.); 7.55 (m, 1H, H arom.); 7.88-7.95 (m, 2H, H arom.). [M-tBu+H]$^+$ (ESI$^+$): 234. $M^-$(ESI$^-$): 288.

c) Protocol for formation of the oxime intermediate (XXXXIII*); e.g., tert-butyl 4-[(Z)-(hydroxyimino)(phenyl)methyl]piperidine-1-carboxylate

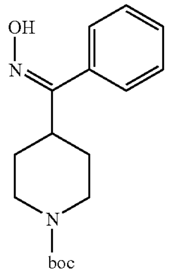

The procedure described in the method A step b) was followed, starting from intermediate XVIII*, e.g., tert-butyl 4-benzylpiperidine-1-carboxylate (1.0 g, 3.46 mmol), affording the desired product XXXXIII*, e.g., tert-butyl 4-[(Z)-(hydroxyimino)(phenyl)methyl]piperidine-1-carboxylate in 94% yield and 97% HPLC purity. It was used in the next step without further purification.

$^1$H NMR (300 MHz, $CDCl_3$); 1.42 (s, 9H, Boc); 1.35-1.58 (m, 2H); 1.58-1.84 (m, 2H), 2.62 (m, 1H, major isomer), 2.63-2.82 (m, 2H); 3.39 (m, 1H, minor isomer); 4.12 (m, 2H); 7.20-7.51 (m, 5H, H arom.). [M-tBu+H]$^+$ (ESI$^+$): 249. $M^-$(ESI$^-$): 303.

d) Protocol for the reduction of the oxime intermediate XXXXIII* into the primary amine (IV); e.g., tert-butyl 4-[amino(phenyl)methyl]piperidine-1-carboxylate.

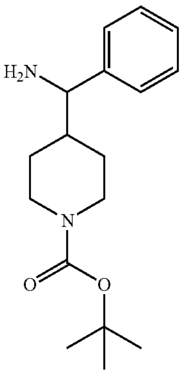 [SMILES: CC(C)(C)OC(=O)N1CCC(C(N)c2ccccc2)CC1]

The oxime intermediate XXXXIII*, e.g., tert-butyl 4-[(Z)-(hydroxyimino)phenyl)methyl]piperidine-1-carboxylate, was dissolved in MeOH. Pd/C (10%) was added and the mixture was placed under 30 bar of $H_2$ overnight. As the reduction was complete, the solution was filtered through celite and the solvents were evaporated, affording the crude the primary amine. It was dissolved in $Et_2O$ and extracted with 3 portions of HCl 1N. Combined acidic fractions were washed with one portion of $Et_2O$. It was then basified with NaOH 5N. The basic aqueous phase was extracted with 3 portions of ether. Combined organic phases were dried over $MgSO_4$, filtrated and evaporated, affording the primary amine IV, e.g., tert-butyl 4-[amino(phenyl)methyl]piperidine-1-carboxylate (729 mg, 68% yield), which was used in the next step without further purification.

$^1$H NMR (300 MHz, $CDCl_3$); 0.93-1.30 (m, 2H); 1.42 (s, 9H, Boc); 1.62 (m, 1H); 1.82-1.98 (m, 2H); 2.59 (m, 2H), 3.61 (d, J=9.0 Hz, 1H); 4.10 (m, 2H); 7.19-7.35 (m, 5H, H arom.). $M^+$($ESI^+$): 291.

e) Protocol for the reduction of boc group into tertiary amine (XXXII); e.g., 1-(1-methylpiperidin-4-yl)-1-phenylmethanamine

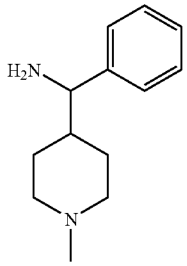

Intermediate XXXI, e.g. tert-butyl 4-[amino(phenyl)methyl]piperidine-1-carboxylate (1.0 g, 3.44 mmol) was dissolved in dry THF (50 mL). $LiAlH_4$ (261 mg, 6.89 mmol) was added in portions. The reaction was heated under reflux overnight. As the reaction was completed, it was quenched with dropwise addition of water (5 mL), followed by NaOH 1N (5 mL) and H2O (5 mL). The suspension thus obtained was extracted with ethyl acetate, dried over $MgSO_4$ and evaporated, affording the crude product. It was further purified by flash chromatography (DCM/MeOH 20:1 with 2% $NH_4OH$) to give the tertiary amine XXXII, e.g., 1-(1-methylpiperidin-4-yl)-1-phenylmethanamine (444.6 mg, 63% yield).

$^1$H NMR (300 MHz, $CDCl_3$); 1.12-1.53 (m, 4H); 1.62 (br s, 2H, $NH_2$); 1.77 (m, 1H); 1.83-2.03 (m, 2H); 2.22 (s, 3H, $CH_3$); 2.75 (m, 1H), 2.91 (m, 1H), 3.60 (d, J=6.0 Hz, 1H); 7.18-7.35 (m, 5H, H arom.). $M^+$($ESI^+$): 204.

f) Enantiomers separation of intermediate (XXXII); e.g., 1-(1-methylpiperidin-4-yl)-1-phenylmethanamine, by chromatography on chiral support Both enantiomer of intermediate XXXII, e.g. 1-(1-methylpiperidin-4-yl) 1-phenylmethanamine (5.00 g), were separated on chiral column (Chiralcell OD-H, 250 mm×20 mm; 5 μm granulometry, Chiral Technologies Europe). Divided in 35 injections, enantiomer (R) (2.344 g, r.t.=5.897 min) and enantiomer (S) (2.552 g, r.t.=7.898 min) were isolated both with e.e. >99.8% (determined on analytical Chiralcell OD-H, 250×4.6 mm, 5 μm granulometry, Chiral Technologies Europe) and 98% yield. Absolute configuration of each enantiomer was established by correlation with biological activity of the final products, knowing that products XXXII bearing (S)-2-substituted benzylamine were more active than the one bearing (R)-2-substituted benzylamine.

1-(2-chloropyridin-4-yl)-1-phenylmethanamine

Following the general Method A, starting from 2-chloroisonicotinic acid, the title compound was obtained in 62% yield.

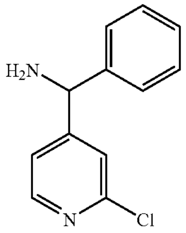 [SMILES: NC(c1ccccc1)c1ccnc(Cl)c1]

$^1$H NMR (300 MHz, $CDCl_3$); 1.69 (s, 2H, $NH_2$); 5.08 (s, 1H, $CHNH_2$); 7.12-7.31 (m, 6H, H arom.); 7.34 (br s, 1H, H pyridine.); 8.20 (d, J=6.0 Hz, 1H, H pyridine). $M^+$($ESI^+$): 219. $M^-$($ESI^-$): 217.

Intermediate 3: Preparation of amino alcohols of general formula (XXVI); e.g., 3-amino-3-(2,4-dimethylphenyl)-1-propanol; 3-amino-3-(2-fluorophenyl)-1-propanol; 3-amino-3-(4-fluorophenyl)-1-propanol; 3-amino-3-(2,6-difluorophenyl)-1-propanol; 3-amino-3-(2-methylphenyl)-1-propanol; 3-amino-3-(2-methoxyphenyl)-1-propanol; 3-amino-3-(4-methylphenyl)-1-propanol; 3-amino-3-(2,3-difluorophenyl)-1-propanol; 3-amino-3-(4-methylphenyl)-1-propanol; 3-amino-3-(4-methoxyphenyl-1-propanol; 3-Amino-3-(2,4-dimethylphenyl)-1-propanol Method A:

To a suspension of sodium borohydride (0.585 g, 15.47 mmol) in dry THF (20 ml) was added the corresponding amino acid (XXV), e.g., 3-(2,4-dimethylphenyl)-β-alanine (1.25 g, 6.45 mmol) in dry THF (20 ml). The reaction mixture was stirred under inert atmosphere and cooled down to zero degree in an ice bath. A solution of iodine (1.64 g, 6.45 mmol) dissolved in dry THF (10 ml) was added dropwise over a period of 30 min resulting in a vigorous evolution of hydrogen. After the addition of iodine was completed and gas evolution ceased, the flask was heated to reflux for 18 hours and then cooled to room temperature, methanol (100 ml) was added cautiously until the mixture became clear. After stirring further 30 min, the solvent were removed, yielding a white paste which was dissolved by addition of 150 ml of 20% aqueous KOH. The solution was stirred for 4 h and extracted with DCM (3×150 ml). The organic layer were dried over sodium sulfate and concentrated in vacuo to give the desired aminoalcohol compounds (XXVI), e.g., 3-amino-3-(2,4-dimethylphenyl)-1-propanol as a yellowish oil (0.85 g, 74%).

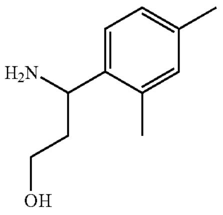

$^1$H NMR (300 MHz, $CDCl_3$): 1.82 (m, 1H), 2.00 (m, 1H), 2.27 (s, 3H), 2.30 (s, 3H), 3.50 (brs, 2H), 3.78 (m, 2H), 4.48 (m, 1H), 6.95 (s, 1H), 7.02 (d, J=7.9 Hz, 1H), 7.34 (d, J=7.9 Hz, 1H)

Method B:

A solution of lithium aluminium hydride (2.5 ml of a 1 M solution in THF) was slowly added to the amino acid (XXV), e.g., 3-(2-fluorophenyl)-β-alanine (272 mg, 1.65 mmol) in THF (4 ml) at 0° C. The mixture was stirred at r.t. for 8 h and quenched with 0.6 ml water, 0.6 ml 1N NaOH and 0.6 ml water. The suspension thus obtained was filtered, dried with a $Na_2SO_4$ cartridge and concentrated under reduced pressure. This crude product (XXVI), e.g., 3-amino-3-(2-fluorophenyl)-1-propanol (131 mg, 69%) was directly engaged in the following step.

Method C:

Preparation of amines of general formula (IV*)/IV'* by enzymatic resolution; e.g. (S)-3-amino-3-(2,4-difluorophenyl)-1-propanol and (R)-3-amino-3-(2,4-difluorophenyl)-1-propanol a) Enzymatic Resolution:

Ethyl-3-amino-3-(2,4-difluorophenyl)-1-propanoate (5.3 g, 23 mmol) was suspended in a phosphate buffer (15 ml, pH=8.2) and gently stirred before the addition of lipase Amano PS (313 mg). The mixture was then stirred at room temperature and the pH maintained at 8.2 by addition of NaOH 1N when necessary. The saponification was monitored by chiral HPLC (column CHIRALPAK AD; hexane/ISOH/TEA 95:5:0.1) and the reaction was stopped just before the complete consumption of the S enantiomer. The mixture was filtered and NaOH 1N was added to the filtrate. Which was then extracted twice with DCM. Combined organic layer were washed with brine, dried over magnesium sulfate, filtrated and concentrated to give 2.72 g of the pure R-ethyl-3-amino-3-(2,4-difluorophenyl)-1-propanoate (chiral HPLC: R=9.8 nm; ee=99%); $^1$H-RMN ($CDCl_3$): 7.40 (m, 1H); 6.80 (m, 2H); 4.60 (m, 1H); 4.10 (m, 2H); 1.93 (m, 2H); 1.25 (m, 3H)). The aqueous phase was lyophilized and redissolved in HCl 1N. It was filtered through a SCX cartridge, suspended in MeOH/ACN 3:1, filtered and concentrated to give the pure S-3-amino-3-(2,4-difluorophenyl)-1-propanoic acid as a nice white powder ($^1$H-RMN ($D_2O$): 7.43 (q, 1H); 7.00 (m, 2H); 4.93 (s, 1H); 3.25 (s, 2H); 3.00 (m, 2H). The enantiomeric purity of the acid was controlled by preparation of the methyl ester derivative with TMS-diazomethane and chiral HPLC analysis using a CHIRALCEL OD-H column with hexane/ISOH/TEA 95:5:0.1 as eluant. Rt (S enantiomer)=10.0 min; Rt (R enantiomer)=9.4 min. ee of the above described S-enantiomer=95.5%.

b) Reduction to the Alcohol

(S)-3-amino-3-(2,4-difluorophenyl)-1-propanol

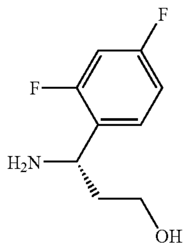 [SMILES: N[C@@H](CCO)c1ccc(F)cc1F]

(S)-3-amino-3-(2,4-difluorophenyl)-1-propanol was obtained following the general method C as described for intermediate 2 from (S)-3-amino-3-(2,4-difluorophenyl)-1-propanoic acid.

$^1$H NMR ($CDCl_3$): 7.30 (m, 1H); 6.83 (m, 2H); 4.37 (m, 1H); 3.82 (m, 2H); 1.90 (m, 4H).

(R)-3-amino-3-(2,4-difluorophényl)-1-propanol

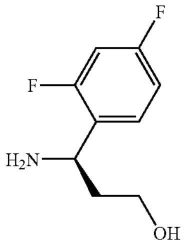 [SMILES: N[C@H](CCO)c1ccc(F)cc1F]

(R)-3-amino-3-(2,4-difluorophenyl)-1-propanol was obtained following the general method B as described for intermediate 2 from Ethyl (R)-3-amino-3-(2,4-difluorophenyl)-1-propanoate Method D:

The amino acid (XXV), e.g., 3-(4-fluorophenyl)-β-alanine (1 eq.) was dissolved in dry THF (30 vol.) and $BH_3$.DMS (2.5 eq) was added. The mixtures were then refluxed between 2 h 00 and 24 h 00 until total disappearance of the starting material by LC-MS analysis. The reaction was then quenched by adding MeOH slowly and the mixture was stirred for 1 h at room temperature. The solvents were then removed by evaporation and 15 ml of aq.KOH solution (20%) was added. The compounds were then extracted with DCM and dried with $Na_2SO_4$, filtered and the DCM removed. The yields of desired compounds (XXVI), e.g., 3-(4-fluorophenyl)-β-alanine, varied between 70 and 90%.

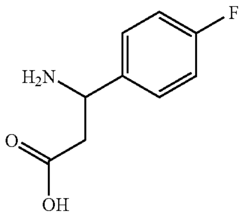 [SMILES: NC(CC(=O)O)c1ccc(F)cc1]

$^1$H NMR (360 MHz, DMSO); 1.53 (s, 9H), 3.62-3.63 (d, 2H), 5.33-5.44 (s, 2H) 7.10 (t, 1H), 8.94 (s, 1H).

Similarly, using one of these three methods, and starting from the appropriate commercial amino acids (XXV), the following, related amino alcohol intermediates (XXVI) were obtained:

3-amino-3-(2,6-difluorophenyl)-1-propanol

Following the general Method B, starting from 3-(2,6-difluorophenyl)-β-alanine, the title compound was obtained in 60% yield.

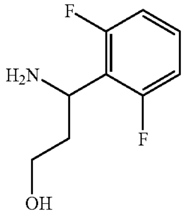 [SMILES: NC(CCO)c1c(F)cccc1F]

$^1$H NMR (300 MHz, $CDCl_3$): 1.71 (d, J=13.9 Hz, 1H), 2.20 (m, 1H), 3.12 (m, 2H), 3.80 (m, 2H), 4.44 (d, J=10.5 Hz, 1H), 6.81 (m, 2H), 7.19 (m, 1H).

3-amino-3-(2-methylphenyl)-1-propanol

Following the general Method B, starting from 3-(2-methylphenyl)-β-alanine, the title compound was obtained in 80% yield.

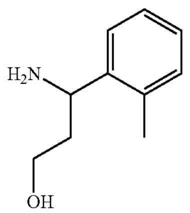

$^1$NMR (300 MHz, $CDCl_3$): 1.84 (m, 2H), 2.28 (s, 3H), 3.07 (brs, 2H), 3.77 (m, 2H), 4.35 (dd, J=9.0 and 3.8 Hz, 1H), 7.08-7.38 (m, 4H).

3-amino-3-(2-methoxyphenyl)-1-propanol:

Following the general Method B, starting from 3-(2-methoxyphenyl)-β-alanine, the title compound was obtained in 70% yield.

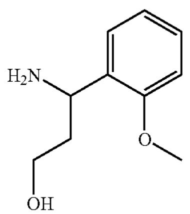

$^1$H NMR (300 MHz, $CDCl_3$): 1.77 (m, 1H), 2.10 (m, 1H), 3.50 (brs, 2H), 3.78 (m, 5H), 4.39 (dd, J=9.8 and 3.8 Hz, 1H), 6.86 (m, 2H), 7.20 (m, 2H).

3-Amino-3-(2,4-dimethylphenyl)-1-propanol:

Following the general Method B, starting from 3-(2,4-dimethylphenyl)-β-alanine, the title compound was obtained in 88% yield.

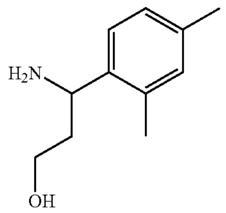

$^1$H NMR (300 MHz, $CDCl_3$): 1.82 (m, 1H), 2.00 (m, 1H), 2.27 (s, 3H), 2.30 (s, 3H), 3.50 (brs, 2H), 3.78 (m, 2H), 4.48 (m, 1H), 6.95 (s, 1H), 7.02 (d, J=7.9 Hz, 1H), 7.34 (d, J=7.9 Hz, 1H)

Intermediate 4: preparation of non-commercial secondary amines; e.g., 2-[(2-furylmethyl)amino]ethanol; methyl 3-(methylamino)propanoate Method A:

An aldehyde, e.g., 2-furfuraldehyde (2 g, 20.82 mmol), and an amine, e.g., 2-aminoethanol, (1.65 g, 27.06 mmol) were poured together in a mixture 1:1 TMOF:DCE (50 ml) and the reaction mixture was cooled down to zero degree. The reducing agent $NaBH(OAc)_3$ (6.18 g, 29.14 mmol) was added in 4 subsequent portions over a 5 min period, the reaction mixture was allowed to gradually warm to room temperature and stirred for 16 hours. The solvents was removed from the reaction in vacuo and the residue was partitioned between dichloromethane (150 ml) and saturated bicarbonate solution (50 ml). After separation, the organic layer was washed with saturated bicarbonate solution (50 ml) and brine (50 ml). The combined organic layers were then dried over sodium sulphate, filtered and the solvent removed in vacuo. The desired secondary amines, e.g., 2-[(2-furylmethyl)amino]ethanol, were obtained as a yellowish oil (1.82 g, 62%).

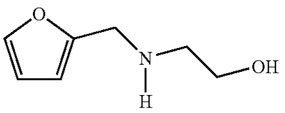

$^1$H NMR (300 MHz, $CDCl_3$); 2.71 (m, $CH_2N$, 2H), 3.25 (s, $CH_2N$, 2H), 3.65 (m, $CH_2O$, 2H), 4.98 (s, NH, 1H), 6.16 (s broad, CH═, 1H), 6.25 (s broad, CH═, 1H), 7.3 (s broad, CH═, 1H); $M^+(ESI^+)$: 142.5; $M^-(ESI^-)$: 140.1.

Method B:

Methyl acrylate (3.1 g, 1 eq, 36 mmol) was dissolved in $CHCl_3$ (50 ml) and methyl amine (1.68 g, 1.5 eq, 56 mmol) was added in one portion. The reaction mixture was stirred and heated to 40° C. for 12 h. The solvents evaporated at the pump to give a yellowish oil, methyl 3-(methylamino)propanoate (3.6 g, 85.3% yield).

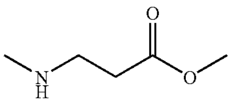

$^1$H NMR (300 MHz, $CDCl_3$); 2.50 (s, $CH_3N$, 3H), 2.51 (m, $CH_2N$, 2H), 2.85 (m, $CH_2C(O)$, 2H), 3.69 (s, $CH_3O$, 3H).

Intermediate 5: Preparation of non-commercial sulfonyl chlorides (VI) and/or sulfonic acids (X); e.g., 4'-methoxy[1,1'-biphenyl]-4-sulfonyl chloride; 4'-chloro[1,1'-biphenyl]-4-sulfonyl chloride; 3'-chloro[1,1'-biphenyl]-4-sulfonyl chloride; 3'-methyl[1,1'-biphenyl]-4-sulfonyl chloride; 2'-chloro[1,1'-biphenyl]-4-sulfonyl chloride; 2'-methyl[1,1'-biphenyl]-4-sulfonyl chloride; 4'-methyl[1,1'-biphenyl]-4-sulfonyl chloride; 4'-methoxy[1,1'-biphenyl]-4-sulfonyl chloride; 4'-methoxy[1,1'-biphenyl]-4-sulfonyl chloride; sodium 4-(3-pyridinyl)benzenesulfonate.

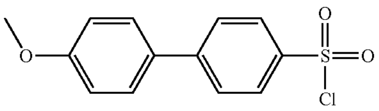 [SMILES: COc1ccc(-c2ccc(S(=O)(=O)Cl)cc2)cc1]

Method A:

a) 4-methoxyphenylboronic acid:

To a solution of 4-bromoanisole (100 g, 0.53 mol) in dry THF (1 L), BuLi (494 ml-, 0.64 mol) was added slowly at −78° C. and stirred for 2 h. To this was added n-butylborate (147 g, 0.64 mol) slowly over 30 min and stirred at RT for 12 h. After completion, the reaction mixture was quenched with water (400 ml), acidified with 1.5N HCl and filtered off the solid precipitate. The solid was washed with water and dried to give 4-methoxyphenylboronic acid (75 g, 92%).

b) 4'-methoxy[1,1'-biphenyl]-4-sulfonic acid:

A mixture of 4-methoxyphenylboronic acid (35 g, 0.23 mol), sodium-4-bromobenzene-sulfonate (50 g, 0.19 mol) and $Na_2CO_3$ (200 g) were taken in toluene (1000 ml) and water (500 ml). To this was added $Pd(PPh_3)_4$ (11 g, 0.011 mol) and the reaction mixture was refluxed for 12 h under $N_2$ atmosphere. The reaction mixture was cooled, filtered off the solid residue, washed with toluene and acidified with 6N HCl. The solid precipitate was filtered and dried to give 4'-methoxy [1,1'-biphenyl]-4-sulfonic acid (45 g, 88%).

c) 4'-methoxy[1,1'-biphenyl]-4-sulfonyl chloride:

To a mixture of 4'-methoxy[1,1'-biphenyl]-4-sulfonic acid (30 g, 0.11 mol) and thionylchloride (90 ml), DMF (1 ml) was added and the reaction mixture was refluxed for 6 h. Excess thionylchloride was distilled off and the crude was purified by column chromatography over silica gel (pet. ether/$CHCl_3$, 1:1) to give 4'-methoxy[1,1'-biphenyl]-4-sulfonyl chloride (30 g, 95%).

$^1$H NMR (300 MHz, $CDCl_3$); 3.9 ($CH_3O$, s, 3H), 7.31 (AB system, J=6 Hz, 2×$H^7$, 2×$H^6$), 7.95 (AB system, J=6 Hz, 2×$H^2$, 2×$H^3$); $M^+(ESI^+)$: 283.2; $M^-(ESI^-)$: 281.6.

Similarly, using the appropriate commercial boronic acids and arylbromides, other related sulfonyl chlorides as mentioned above were obtained.

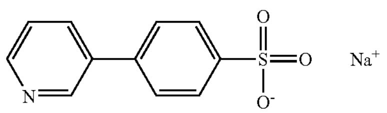

Method B:

a) isobutyl 4-bromobenzenesulfonate 4-bromobenzenesulfonyl chloride 850 g, 0.19 mol) was suspended in 2-propanol (45 ml, 3 eq) and the slurry was cooled to less then 10° C. Pyridine (32 ml, 2 eq) was added in portions while maintaining the reaction temperature below 10° C. After reaction completion (ca. 3 hours), 11 ml of glacial acetic acid followed by 250 ml of methyl tert-butyl ether (MTBE) were added. The layers were separated and the rich organic layer was successively washed with 125 ml of 1N aqueous hydrochloric acid and 150 ml of saturated sodium bicarbonate solutions. The rich MTBE solution was solvent exchanged into hexane (i.e., the addition of hexane with concurrent distillation of MTBE) to induce crystallisation. The crystal slurry was filtered, washed and dried in vacuo at no more than 25° C., to give 48 g (87% yield) of isobutyl 4-bromobenzenesulfonate.

b) 4-(isobutoxysulfonyl)phenylboronic acid

To a solution of isobutyl 4-bromobenzenesulfonate (56 g, 200 mmol) in 280 ml of THF was added triisopropylborate (84 ml, 1.82 eq) and the reaction mixture was cooled to less than −65° C. To the cooled solution, n-butyllithium (144 ml, 0.9 eq, 1.07 M in hexanes) was slowly added while maintaining the temperature below −65° C. The reaction mixture was stirred for at least 0.5 hours and then was quenched with 1M sulfuric acid (200 ml). The reaction mixture was allowed to warm to ca. 20° C. The layers were separated and the rich organic layer containing 35 g (92% yield) of 4-(isobutoxysulfonyl)phenylboronic acid was used without further purification in the next step.

c) sodium 4-(3-pyridinyl)benzenesulfonate

The THF-Hexane-MTBE solution containing 23 g (93.3 mmol) of 4-(isobutoxysulfonyl)phenylboronic acid was concentrated to a concentration of ca. 7 ml/g. A portion of this solution containing ca. 4.7 g (19 mmol, 0.26 eq) was added to a solution of 15.4 g (75 mmol) of 3-iodopyridine dissolved in 100 ml of degassed tetrahydrofuran. To this solution, tris (dibenzylidene acetone) dipalladium (0) (0.5 g, 0.6 mol %) and degassed aqueous sodium carbonate solution (300 ml, 3 eq) were added. The reaction mixture was heated to ca. 50° C. to initiate the coupling reaction. During the reaction, $Pd_2(dba)_3$ (0.5 g per addition) and rich organic concentrate containing 4-(isobutoxysulfonyl)phenylboronic acid (4.7 g, 0.26 eq per addition) were added in several portions until all the 3-iodopyridine was consumed. The reaction mixture was further heated at ca. 55° C. for an additional 4 hours. The reaction mixture was filtered and washed with methyl-tert-butyl ether. The pH of the product-rich aqueous solution was adjusted to ca. 4, treated with trithiacyanuric acid (Ig) and filtered to remove Pd containing by-products. The pH of the product-rich aqueous solution was adjusted to ca. 7 and was saturated with solid NaCl (118 g) to initiate the crystallisation of the product. The salted-out product was dried in vacuo at less than 70° C. For recrystallization, the dried product was dissolved in 350 ml of 190 proof ethanol at ca. 75° C. The solution was filtered and concentrated to ca. 100 ml and cooled to ca. 30° C. to initiate crystallization. About 200 ml of MTBE was added to maximize the yield. The crystal slurry was filtered, washed and dried in vacuo less than 70° C., to give 13.4 g (70% yield) of sodium 4-(3-pyridinyl)benzenesulfonate.

$^1$H NMR (300 MHz, DMSO); 7.45 (AB system, J=6 Hz, 2×$H^3$, 2×$H^4$), 7.8 (dd, J=4 Hz, J=6 Hz, $H^{10}$), 8.71 (dd, J=7 Hz, J=1 Hz, $H^{11}$), 8.81 (dd, J=6 Hz, J=1 Hz, $H^9$), 9.19 (d, J=1 Hz, $H^7$); $M^+(ESI^+)$: 236.2; $M^-(ESI^-)$: 234.2.

Other related sulfonyl chlorides or sulfonyl acids as mentioned above were obtained such as benzeneacetic acid, 4-(chlorosulfonyl)-alpha,alpha-dimethyl-, methyl ester

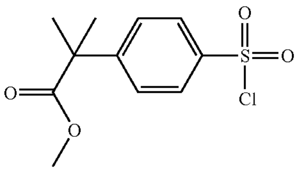 [SMILES: COC(=O)C(C)(C)c1ccc(S(=O)(=O)Cl)cc1]

Method C:

a) 2-methyl-2-phenyl propanoic methyl ester

The 2-methyl-2-phenyl propanoic acid (1.045 g, 6.36 mmol) was dissolved in 10 mL od Toluene/MeOH (1:1). Trimethylsilyl)diazomethane (9.54 mL in a solution 2M in hexane, 19.08 mmol, 3 eq) was added. The reaction mixture was stirred overnight at room temperature, then the solution was evaporated under vacuum et the residue dissolved in EtOAc. The organic layer was washed with $NaHCO_3$ sat., NaCl sat., and dried over $MgSO_4$. The solvent was evaporated to give a colorless (1.1 g, quantitative yield). $^1$H-RMN($CDCl_3$) δ 7.22-7.34 (m, 5H); 3.66 (s, 3H); 1.59 (s, 6H).

b) benzeneacetic acid, 4-(chlorosulfonyl)-alpha,alpha-dimethyl-, methyl ester 2-methyl-2-phenyl propanoic methyl ester (1.1 g, 6.17 mmol) was dissolved in 20 mL of anhydrous DCM and the reaction mixture was cooled down to −78° C. The chlorosulfonic acid (2.05 mL, 30.86 mmol, 5 eq) dissolved in 10 mL of anhydrous DCM was added dropwise during a period of 2 h. The reaction mixture was stirred overnight at room temperature. The reaction was quenched by addition of ice and the product extracted with DCM (3×50 mL) The organic layer was washed with NaCl sat, dried over $MgSO_4$, evaporated to give an oil (1 g, yield: 59%, HPLC purity: 84%)

$^1$H-RMN ($CH_2Cl_2$) δ 7.99 (d, J=9.1, 2H); 7.58 (d, J=8.7, 2H); 3.69 (s, 3H); 1.56 (s, 6H). MS (ESI−): 275.15

Intermediate 6: Thiazolidine intermediates of general formula (V); e.g. tert-butyl 2-({[(1S3-hydroxy-1-phenylpropyl]amino}carbonyl)-1,3-thiazolidine-3-carboxylate

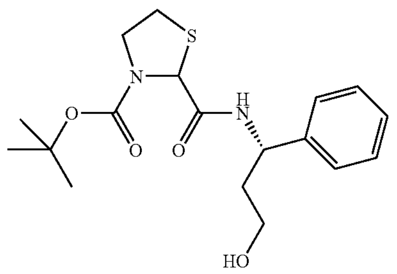

Commercial 3-(tert-butoxycarbonyl)-1,3-thiazolidine-2-carboxylic acid (III) (1 g, 4.29 mmol) was dissolved in dry THF (50 ml). A mechanical stirrer was placed in the flask and the solution stirred vigorously. The solution was cooled down to −25° C. and N-methyl morpholine (1.084 g, 10.72 mmol) was added in dry THF (5 ml). A solution of isobutyl-chloroformate (0.615 g, 4.5 mmol) in dry THF (10 ml) was then added dropwise over a period of 10 minutes with continued vigorous stirring, the reaction's exotherm being maintained at the optimal temperature of −25° C. by the use of a dry-acetone bath. After the complete addition of the chloroformate, the reaction mixture was stirred at −25° C. for 30 min after which time an amine (IV)/(IV*), e.g., (3S)-3-amino-3-phenyl-1-propanol (0.778 g, 5.14 mmol) was added drop-wise over a period of 10 min. The reaction mixture was allowed to gradually warm to room temperature and stirred overnight. The solvent was removed and the residue re-dissolved in ethyl acetate (150 ml). The organic layer was washed subsequently with a saturated solution of ammonium chloride (100 ml), saturated bicarbonate (100 ml) and brine (100 ml). Organics then dried with magnesium sulfate and concentrated in vacuo. The product (V), e.g., tert-butyl 2-({[(1S)-3-hydroxy-1-phenyl-propyl]amino}carbonyl)-1,3-thiazolidine-3-carboxylate, was finally obtained as a white foam (1.5 g, 95%). The antipodal intermediate, tert-butyl 2-({[(1S)-3-hydroxy-1-phenyl-propyl]amino}carbonyl)-1,3-thiazolidine-3-carboxylate, as well as the racemic inter-mediate, tert-butyl 2-({[3-hydroxy-1-phenylpropyl]amino}carbonyl)-1,3-thiazolidine-3-carboxylate were made according to the same protocol, starting from commercial (3R)-3-amino-3-phenylpropan-1-ol or 3-amino-3-phenylpropan-1-ol, respectively.

$^1$H NMR (300 MHz, $CDCl_3$); 1.72 (s, 9H), 2.1-2.55 (m, $CH_2$, 2H), 3.2-3.6 (m, $CH_2S$, 21H), 3.9-4.25 (m, $CH_2O$, $CH_2N$, 4H), 5.49 (m, CH, 1H), 5.51 (s, CH, 1H), 6.85 (s broad, NH, 1H), 7.5-7.7 (m, CH(Ar), 5H); $M^+$($ESI^+$): 367.1.

According to the general method outlined above for the synthesis of Intermediates 6, starting from commercial 3-(tert-butoxycarbonyl)-1,3-thiazolidine-2-carboxylic acid (III) and the appropriate commercial amines (IV), the following, related intermediates (V) were obtained:

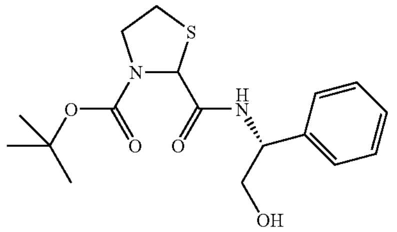 [SMILES: CC(C)(C)OC(=O)N1CCSC1C(=O)N[C@@H](CO)c1ccccc1]

tert-butyl 2-({[(1R)-2-hydroxy-1-phenylethyl]amino}carbonyl)-1,3-thiazolidine-3-carboxylate: $^1$H NMR (300 MHz, $CDCl_3$); 1.7 (s, 9H), 3.2-3.6 (m, $CH_2S$, 2H), 3.7-4.0 (m, $CH_2O$, $CH_2N$, 4H), 5.1 (m, CH, 1H), 5.5 (s, CH, 1H), 6.8 (s broad, NH, 1H), 7.5-7.7 (m, CH(Ar), 5H); $M^+$($ESI^+$): 353.4.

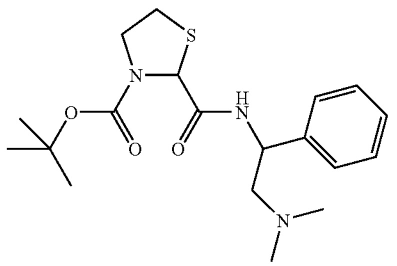 [SMILES: CN(C)CC(NC(=O)C1SCCN1C(=O)OC(C)(C)C)c1ccccc1]

tert-butyl 2-({[2-(dimethylamino)-1-phenylethyl]amino}carbonyl)-1,3-thiazolidine-3-carboxylate: $^1$H NMR (300 MHz, $CDCl_3$); 1.4 (s, 9H), 2.28 (s, $CH_3N$, 6H), 2.4-2.7 (m, $CH_2N$, 2H), 2.9-3.3 (m, $CH_2S$, 2H), 3.7-4.0 (m, $CH_2N$, 2H), 4.85 (m, CH, 1H), 5.3 (s broad, CH, 1H), 7.2-7.4 (m, CH(Ar), 5H); $M^+$($ESI^+$): 380.5.

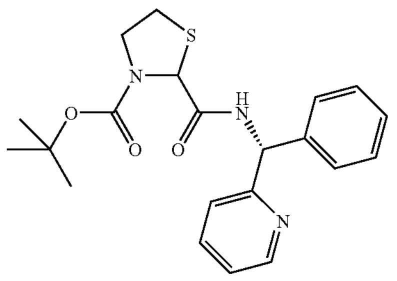 [SMILES: CC(C)(C)OC(=O)N1CCSC1C(=O)N[C@H](c1ccccc1)c1ccccn1]

tert-butyl 2-({[(R)-phenyl(2-pyridinyl)methyl]amino}carbonyl)-1,3-thiazolidine-3-carboxylate: $^1$H NMR (300 MHz, $CDCl_3$); 1.5 (m, 9H), 3.2-3.4 (m, $CH_2S$, 2H), 3.7-4.0 (m, $CH_2N$, 2H), 5.3 (m, CH, 1H), 6.1 (s, CH, 1H), 6.8 (s broad, NH, 1H), 7.0-7.3 (m, CH(Ar), 7H), 7.6 (m, CH(Pyr), 1H), 8.1 (m, CH(Pyr), 1H); $M^+(ESI^+)$: 400.2.

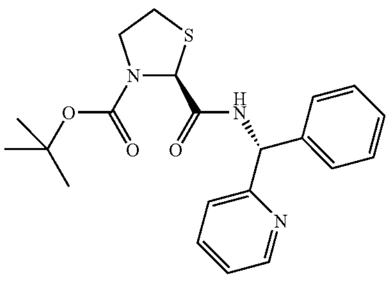 [SMILES: CC(C)(C)OC(=O)N1CCS[C@H]1C(=O)N[C@H](c1ccccc1)c1ccccn1]

tert-butyl (2S)-2-({[(1S)-3-hydroxy-1-phenylpropyl] amino}carbonyl)-1,3-thiazolidine-3-carboxylate: $^1H$ NMR (300 MHz, $CDCl_3$); 1.5 (m, 9H), 3.2-3.45 (m, $CH_2S$, 2H), 3.7-3.9 (m, $CH_2N$, 2H), 5.3 (m, CH, 1H), 6.1 (s, CH, 1H), 6.8 (s broad, NH, 1H), 7.0-7.3 (m, CH(Ar), 7H), 7.6 (m, CH(Pyr), 1H), 8.1 (m, CH(Pyr), 1H); $M^+(ESI^+)$: 400.2.CH(Pyr), 1H); $M^+(ESI^+)$: 400.5.

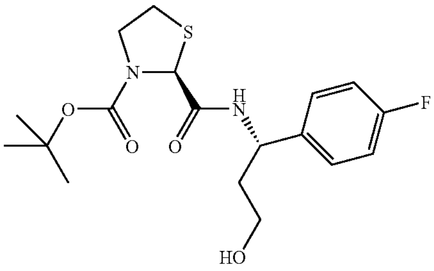 [SMILES: CC(C)(C)OC(=O)N1CCS[C@H]1C(=O)N[C@@H](CCO)c1ccc(F)cc1]

tert-butyl (2S)-2-({[(1S)-1-(4-fluorophenyl)-3-hydroxypropyl]amino}carbonyl)-1,3-thiazolidine-3-carboxylate: $^1H$ NMR (300 MHz, $CDCl_3$); 1.5 (s, 9H), 2.1-2.52 (m, $CH_2$, 2H), 3.25-3.6 (m, $CH_2S$, 2H), 3.9-4.15 (m, $CH_2O$, $CH_2N$, 4H), 5.45 (m, CH, 1H), 5.50 (s, CH, 1H), 6.75 (s broad, NH, 1H), 7.5-7.6 (m, CH(Ar), 4H); $M^+(ESI^+)$: 385.5.

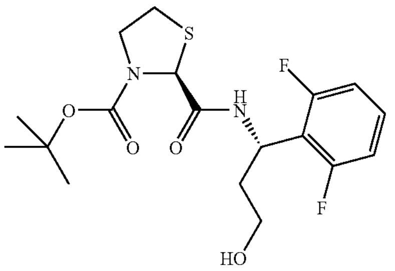 [SMILES: CC(C)(C)OC(=O)N1CCS[C@H]1C(=O)N[C@@H](CCO)c1c(F)cccc1F]

tert-butyl (2S)-2-({[(1S)-1-(2,6-difluorophenyl)-3-hydroxypropyl]amino}carbonyl)-1,3-thiazolidine-3-carboxylate: $^1H$ NMR (300 MHz, $CDCl_3$); 1.7 (s, 9H), 2.1-2.5 (m, $CH_2$, 2H), 3.2-3.5 (m, $CH_2S$, 2H), 3.9-4.15 (m, $CH_2O$, $CH_2N$, 4H), 5.40 (m, CH, 1H), 5.45 (s, CH, 1H), 6.8 (s broad, NH, 1H), 7.5-7.5 (m, CH(Ar), 3H); $M^+(ESI^+)$: 403.2.

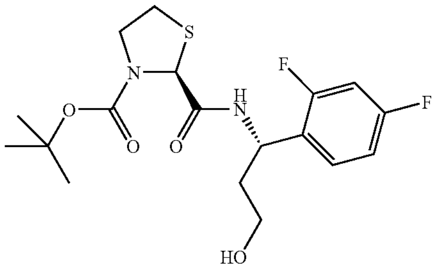 [SMILES: CC(C)(C)OC(=O)N1CCS[C@H]1C(=O)N[C@@H](CCO)c1ccc(F)cc1F]

tert-butyl (2S)-2-({[(1S)-1-(2,4-difluorophenyl)-3-hydroxypropyl]amino}carbonyl)-1,3-thiazolidine-3-carboxylate: $^1H$ NMR (300 MHz, $CDCl_3$); 1.65 (s, 9H), 2.1-2.55 (m, $CH_2$, 2H), 3.2-3.56 (m, $CH_2S$, 2H), 3.9-4.27 (m, $CH_2O$, $CH_2N$, 4H), 5.46 (m, CH, 1H), 5.6 (s, CH, 1H), 6.8 (s broad, NH, 1H), 7.5-7.7 (m, CH(Ar), 4H); $M^+(ESI^+)$: 403.8.

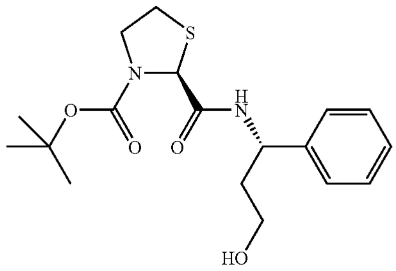 [SMILES: CC(C)(C)OC(=O)N1CCS[C@H]1C(=O)N[C@@H](CCO)c1ccccc1]

tert-butyl (2S)-2-({[(1S)-3-hydroxy-1-phenylpropyl] amino}carbonyl)-1,3-thiazolidine-3-carboxylate: $^1H$ NMR (300 MHz, $CDCl_3$); 1.7 (s, 9H), 2.1-2.5 (m, $CH_2$, 2H), 3.2-3.6 (m, $CH_2S$, 2H), 3.9-4.25 (m, $CH_2O$, $CH_2N$, 4H), 5.47 (m, CH, 1H), 5.49 (s, CH, 1H), 6.85 (s broad, NH, 1H), 7.5-7.7 (m, CH(Ar), 5H); $M^+(ESI^+)$: 367.2.

Intermediate 7: e.g. methyl 3-([1,1'-biphenyl]-4-ylsulfonyl)-1,3-thiazolidine-2-carboxylate

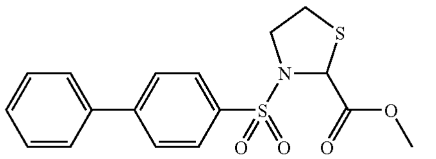 [SMILES: COC(=O)C1SCCN1S(=O)(=O)c1ccc(-c2ccccc2)cc1]

Commercial 1,3-thiazolidine-2-carboxylic acid methyl ester hydrochloride (IX) (3 g, 16.33 mmol) was dissolved in DCM dry (50 ml) and the solution was cooled down to zero degree. Triethylamine (4.96 g, 49 mmol) was added in DCM (10 ml) followed by the sulfonyl chloride (4.13 g, 16.33 mmol) in DCM (50 ml). The reaction mixture was stirred for 24 h at room temperature. Aminomethyl polystyrene resin (1 g, 3.3 mmol/g) was added to the reaction mixture and stirred for two hours before filtering at the pump. The organic solution was washed with saturated solution of ammonium chloride (100 ml) and brine (100 ml). The organic layer was then dried with magnesium sulfate and concentrated in vacuo (crude yield 70%). Silica gel chromatography, eluting with 15% ethyl acetate in hexanes gave the desired compound as a white solid, methyl 3-([1,1'-biphenyl]-4-ylsulfonyl)-1,3-thiazolidine-2-carboxylate (2.98 g, 50% yield).

$^1$H NMR (300 MHz, $CDCl_3$); 2.7-3.1 (m, $CH_2S$, 2H), 3.7 (s, $CH_3O$, 3H), 3.8-4.0 (m, $CH_2N$, 2H), 5.2 (m, CH, 1H), 5.5 (s, CH, 1H), 7.4-8.0 (m, CH(Ar), 9H); $M^-$($ESI^-$): 362.5.

Intermediate 8: Thiazolidine intermediates of general formula (VIII); e.g. 3-([1,1'-biphenyl]-4-ylsulfonyl)-1,3-thiazolidine-2-carboxylic acid and

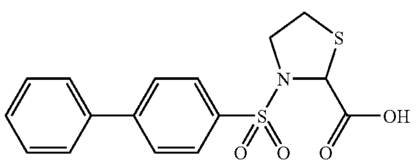

Method A:

A stirred solution of 1,3-thiazolidine-2-carboxylic acid (VII) (6.0 g, 45.1 mmol, 1 eq) in dioxane (60 ml, 10 vol), 1M aqueous sodium carbonate solution (90 ml, 15 vol) and water (50 ml, 8.3 vol) was treated at RT over 50 minutes with a solution of a sulfonyl chloride (VI), e.g., [1,1'-biphenyl]-4-sulfonyl chloride (12.0 g, 47.5 mmol, 1.05 eq) in dioxane (50 ml, 8.3 vol w.r.t. thiazolidine input). The thick white suspension which resulted was stirred (poorly) for 2.5 hrs, when TLC (silica, 1:1 EtOAc/hexane, 1% AcOH) showed a negligible amount of sulphonyl chloride remaining. The reaction mixture was cooled to 10° C. and filtered, solids washed with water (50 ml), and the filter cake sucked "dry" overnight. The wet filter cake (32 mg) was stirred in water (165 ml) and dioxane (160 ml), and warmed to ca. 60° C., giving a clear colorless solution, (pH ca.7), which was stirred at about this temperature while adding 2M HCl (13 ml) to give a pH of 2. The resulting suspension was stirred while cooling to 10° C., aged for a few minutes then filtered and solids washed with water (3×20 ml). The product of general structure (VIII), e.g., 3-([1,1'-biphenyl]-4-ylsulfonyl)-1,3-thiazolidine-2-carboxylic acid, was dried in vacuo at 45° C. giving 11.01 g (70%).

$^1$H NMR (300 MHz, DMSO-d6); 2.6-3.1 (m, $CH_2S$, 2H), 3.6-3.9 (m, $CH_2N$, 2H) 5.45 (s, CH, 1H), 7.4-8.0 (m, CH(Ar), 9H); $M^-$($ESI^-$): 348.0.

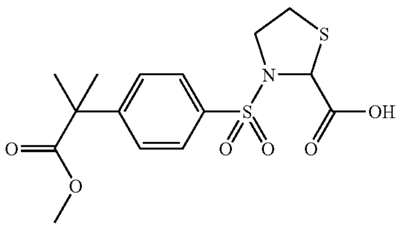 [SMILES: COC(=O)C(C)(C)c1ccc(S(=O)(=O)N2CCSC2C(=O)O)cc1]

Following the same method A, starting from benzeneacetic acid, 4-(chlorosulfonyl)-alpha,alpha-dimethyl-, methyl ester, the compound 2-thiazolidinecarboxylic acid, 3-[[4-(2-methoxy-1,1-dimethyl-2-oxoethyl)phenyl]sulfonyl]—was obtained in 63% yield and 93% HPLC purity.

$^1$H-RMN ($CDCl_3$) δ 7.83 (d, Jd=8.67, 2H); 7.50 (d, Jd=8.67, 2H); 5.47 (s, 1H); 3.78-3.90 (m, 2H); 3.68 (s, 3H); 3.19 (td, Jt=6.03, Jd=10.55, 1H); 2.80 (td, Jt=6.41, Jd=10.55, 1H); 1.61 (s, 6H)

Method B:

A solution was made containing Intermediate 6, e.g., methyl 3-([1,1'-biphenyl]-4-ylsulfonyl)-1,3-thiazolidine-2-carboxylate (2.0 g, 5.5 mmol, 1 eq), in dry DCM (50 ml). The flask was cooled down to −20° C. in a dry-acetone bath. A solution of boron tribromide (5.55 g, 22.0 mmol) in dry DCM (30 ml) was added drop wise over a period of 10 minutes. The reaction mixture was stirred for 1 h at 0° C. The reaction mixture was diluted with DCM (50 ml) and washed with a 1M HCl solution (2×50 ml) and with brine (50 ml) before drying over magnesium sulfate, filtering and removal of solvent in vacuo. The desired product of general structure (VIII), e.g., 3-([1,1'-biphenyl]-4-ylsulfonyl)-1,3-thiazolidine-2-carboxylic acid, was isolated as a white powder (1.8 g, 94%).

Intermediate 9: Thiazolidine intermediates of general formula (XXVIII); e.g., (3S)-3-({[(2S)-3-([1,1'-biphenyl]-4-ylsulfonyl)-1,3-thiazolidin-2-yl]carbonyl}amino-3-phenylpropyl methanesulfonate; 3-({[3-([1,1'-biphenyl]-4-ylsulfonyl-1,3-thiazolidin-2-yl]carbonyl}amino)-3-phenylpropyl methanesulfonate

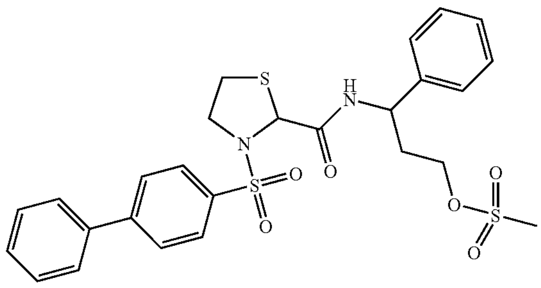

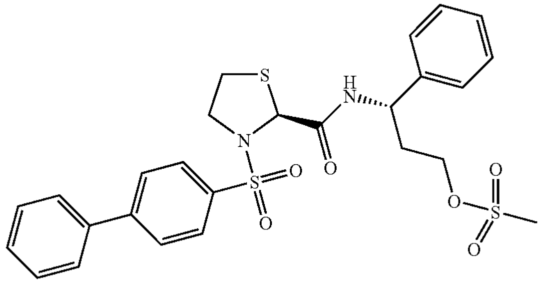

Intermediates of general structure (XXVI), e.g., (2S)-3-([1,1'-biphenyl]-4-ylsulfonyl)-N-[(1S)-3-hydroxy-1-phenylpropyl]-1,3-thiazolidine-2-carboxamide or 3-([1,1'-biphenyl]-4-ylsulfonyl)-N-(3-hydroxy-1-phenylpropyl)-1,3-thiazolidine-2-carboxamide (3.5 g, 7.25 mmol), were dissolved in dry DCM (20 ml) at 0° C. and TEA (2.2 g, 21.76 mmol) was added followed by MsCl (1 g, 8.7 mmol) in 10 ml of DCM. The reaction mixture was stirred for 4 h at r.t., then washed with saturated $NH_4Cl$ and brine. The organic layer was dried over $Na_2SO_4$, and the solvents evaporated. The crude products of general structure (XXVIII), e.g., (3S)-3-({[(2S)-3-([1,1'-biphenyl]-4-ylsulfonyl)-1,3-thiazolidin-2-yl]carbonyl}amino)-3-phenylpropyl methanesulfonate and 3-({[3-([1,1'-biphenyl]-4-ylsulfonyl)-1,3-thiazolidin-2-yl]carbonyl}amino)-3-phenylpropyl methanesulfonate were directly utilized for the next reaction.

$^1$H NMR (300 MHz, $CDCl_3$); 2.0-2.25 (m, 2H), 2.25-2.8 (m, $CH_2S$, 2H), 2.87 (s broad, $CH_3$, 3H), 3.5-4.2 (m, $CH_2N$, $CH_2O$, 4H), 5.03 (m, CH, 1H), 5.15 (s broad, CH, 1H), 7.2-8.0 (m, CH(Ar), 14H).

Intermediate 10: Thiazolidine intermediates of general formula (XXXI); e.g., (2S)—N-[(1S)-3-amino-1-phenylpropyl]-3-([1,1'-biphenyl]-4-ylsulfonyl)-1,3-thiazolidine-2-carboxamide and N-[3-amino-1-phenylpropyl]-3-([1,1'-biphenyl]-4-ylsulfonyl)-1,3-thiazolidine-2-carboxamide

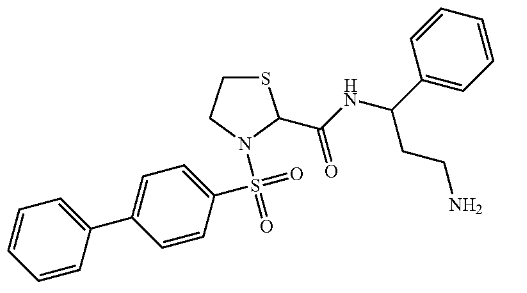

a) Mitsunobu-reaction using phthalimide, e.g., 3-([1,1'-biphenyl]-4-ylsuyfonyl)-N-[3-(1,3-dioxo-1,3-dihydro-2H-isoindol-2-yl)-1-phenylpropyl]-1,3-thiazolidine-2-carboxamide Intermediates of general structure (XXVI), e.g., 3-([1,1'-biphenyl]-4-ylsulfonyl)-N-(3-hydroxy-1-phenylpropyl)-1,3-thiazolidine-2-carboxamide (1.0 g, 1.0 eq, 2.07 mmol) were dissolved in 20 ml dry THF under nitrogen. Phthalamide (395 mg, 1.5 eq, 2.69 mmol), diethylazodicarboxylate (470 mg, 1.5 eq, 2.69 mmol) and polymer bound triphenyl phosphine (1.0 g, 1.5 eq, 2.70 mmol) were then added and the reaction mixture was shaken for 12 hours at RT. The triphenyl phosphine resin was filtered off and the THF solution evaporated in vacuo. The residue was taken up in DCM and washed twice with a saturated sodium carbonate solution and then water. The organic layer was dried with magnesium sulfate and concentrated in vacuo to give a crude product which was purified on silica gel using cyclohexane/ethyl acetate(7/3) as eluent, to obtain the desired products, e.g., 3-([1,1'-biphenyl]-4-ylsulfonyl)-N-[3-(1,3-dioxo-1,3-dihydro-2H-isoindol-2-yl)-1-phenylpropyl]-1,3-thiazolidine-2-carboxamide in 57% yield as a white oil in 96% purity by HPLC.

$^1$H NMR (400 MHz, $CDCl_3$); 2.10-2.40 (m, 2H, $CH_2$), 2.509-2.61 (m, 1H, $CH_2S$), 2.90-3.30 (m, 1H, $CH_2S$), 3.69-3.93 (m, 4H, $CH_2N$), 5.06 (m, 1H, CH), 5.32 (s, 1H, CH), 6.39 (m, 1H, NH), 7.05-7.67 (m, 16H, CH(Ar)), 7.71-7.81 (m, 2H, CH(Ar)); $M^+(ESI^+)$: 612.6; $M^-(ESI^-)$: 610.71.

b) Hydrazinolysis, e.g., N-[3-amino-1-phenylpropyl]-3-([1,1'-biphenyl]-4-ylsulfonyl)-1,3-thiazolidine-2-carboxamide The intermediates from the previous step, e.g., 3-([1,1'-biphenyl]-4-ylsulfonyl)-N-[3-(1,3-dioxo-1,3-dihydro-2H-isoindol-2-yl)-1-phenylpropyl]-1,3-thiazolidine-2-carboxamide (400 mgs, 1.0 eq, 0.65 mmol) were dissolved in a mixture of EtOH/THF (15/1) at room temperature. 1.5 ml of hydrazine was introduced and reaction mixture heated up to 70 C for 12 hours. The corresponding phthalhydrazide precipitate was filtered off, rinsed with DCM and the organic solvents concentrated in vacuo. The residue was taken up in ethylacetate (20 ml), washed several times with a sodium hydrogeno carbonate solution (10%), dried with magnesium sulfate. The organic solvents were then concentrated in vacuo to give a crude compound, which was purified by flash chromatography using DCM/MeOH (98/2) as eluent, affording the desired compounds, e.g., N-[3-amino-1-phenylpropyl]-3-([1,1'-biphenyl]-4-ylsulfonyl)-1,3-thiazolidine-2-carboxamide was obtained in 70% yield as a white oil in 98% purity by HPLC.

$^1$H NMR (400 MHz, $CDCl_3$); 1.88 (m, 2H, $CH_2$), 2.40 (m, 2H, $NH_2$), 2.48-2.50 (m, 1H, $CH_2S$), 2.89-2.90 (m, 1H, $CH_2S$), 3.20-3.53 (m, 2H, $CH_2$), 3.70-3.90 (m, 2H, $CH_2N$), 5.10 (m, 1H, CH), 5.27 (s, 1H, CH), 6.45 (m, 1H, NH), 7.19-7.88 (m, 14H, CH(Ar)); $M^+(ESI^+)$: 482.47; $M^-(ESI^-)$: 480.88.

Intermediate 11: Substituted aryl and heteroaryl aldehyde derivatives of general formula (XVI); e.g., 6-[2-(dimethylamino)ethoxy]-2-pyridinecarbaldehyde

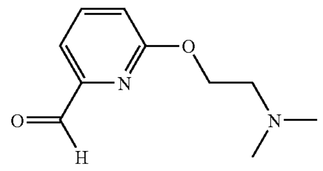

a) N-(2-[(6-bromo-2-pyridinyl)oxy]ethyl)-N,N-dimethylamine (XXIII)

2-dimethylaminoethanol (2 mL, 20 mmol) was added at rt to a suspension of NaH (oil was not removed) in dry DMF (3 mL). The mixture was stirred at rt for 2 hours and 1 h at 60° C. Then commercial 2,6-dibromopyridine (6.16 g, 26 mmol, 1.3 eq) was added at rt and the whole was stirred at rt overnight. The crude mixture was dissolved in some $Et_2O$ and was extracted with 2 portions of citric acid 30%. Combined aqueous phases were washed with 2 portions of $Et_2O$. The aqueous phase was basified with NaOH 5N at 0° C. and was extracted with 3 portions of $Et_2O$. Combined organic phases was dried over $MgSO_4$, filtrated and evaporated. As some DMF remained, HCl in Et2O was added. The solvents were evaporated and the resulting solid was put at the pump for 4 hours. It was dissolved in $H_2O$ and basified with NaOH 5 M. The desired product (the base) was extracted with 3 portions of $Et_2O$. Combined organic layers were dried over MgSO4, filtrated and evaporated to give the desired product (XXIII), N-{2-[(6-bromo-2-pyridinyl)oxy]ethyl}-N,N-dimethylamine (4.4309 g, 18.076 mmol, 90.4%).

$^1$H NMR (360 MHz, $CDCl_3$); 2.16 (s, 6H); 2.53 (m, 2H); 4.23 (m, 2H); 6.58 (m, 1H); 6.88 (m, 1H); 7.24 (m, 1H); $M^+(ESI^+)$: 245.2/247.2 b) 6-[2-(dimethylamino)ethoxy]-2-pyridinecarbaldehyde n-BuLi 2.5 M in hexane (1.2 mL, 3 mmol, 3 eq) was added at −70° C. to a solution of the product from the previous step, N-{2-[(6-bromo-2-pyridinyl)oxy]ethyl}-N,N-dimethylamine (245 mg, 1 mmol) in dry THF (10 mL). The reaction mixture was stirred at −70° C. for 1 h 30 min. Ethyl formate (freshly distilled over $P_2O_5$) was added at −70° C., and the reaction mixture was stirred at −70° C. for 2 hours. The reaction was quenched with addition of water. The reaction mixture was extracted with 3 portions of DCM. Combined organic phase were dried with MgSO4, filtrated and evaporated to give the desired product, 6-[2-(dimethylamino) ethoxy]-2-pyridinecarbaldehyde (192 mg, 0.988 mmol, 99%).

$^1$H NMR (360 MHz, $CDCl_3$); 2.24 (s, 6H); 3.62 (m, 2H); 4.41 (m, 2H); 6.91 (d, 1H, J=6 Hz); 7.44 (m, 1H); 7.60 (t, 1H, J=6 Hz); 9.81 (s, 1H).

Example 1

General protocols for the solution-phase synthesis of 1,3-thiazolidine-2-carboxamide derivatives of general formula (1); e.g., 3-([1,1'-biphenyl]-4-ylsulfonyl)-N-[(1S)-3-hydroxy-1-phenylpropyl]-1,3-thiazolidine-2-carboxamide; (2S)-3-([1'-biphenyl]-4-ylsulfonyl)-N-[(1S)-3-hydroxy-1-phenylpropyl]-1,3-thiazolidine-2-carboxamide; (2R)-3-([1,1'-biphenyl]-4-ylsulfonyl)-N-[1S)-3-hydroxy-1-phenylpropyl]-1,3-thiazolidine-2-carboxamide, (2S)-3-(1,1'-biphenyl-4-ylsulfonyl)-N—[(R)-phenyl(pyridin-2-yl)methyl]-1,3-thiazolidine-2-carboxamide Strategy 1:

N-methyl morpholine (NMM) (3.24 g, 2.5 eq, 32.15 mmol) was added to a solution of a compound of general formula (VIII) (Intermediate 8, 4.50 g, 1 eq, 12.86 mmol), e.g., 3-([1,1'-biphenyl]-4-ylsulfonyl)-1,3-thiazolidine-2-carboxylic acid, in dry THF (100 ml) and the reaction mixture was cooled down to −25° C. To the reaction mixture was then added drop wise, over a period of 5 minutes, isobutyl chloroformate (1.84 g, 1.05 eq, 13.50 mmol) in solution in dry THF (20 ml). The resulting mixture was stirred at −25° C. for 30 minutes, after which time an amine of general formula (IV) or (IV*) (commercial or Intermediate 2, 2.14 g, 1.1 eq, 14.15 mmol), e.g., (3S)-3-amino-3-phenyl-1-propanol, was added in dry THF (20 ml) over a period of 5 minutes. The mixture was allowed to gradually warm to room temperature and stirred overnight at room temperature. The solvent was removed and the residue re-dissolved in ethyl acetate (200 ml). The organic layer was washed subsequently with a saturated solution of ammonium chloride (100 ml), saturated bicarbonate (100 ml) and brine (100 ml). The combined organic phases were dried with magnesium sulfate and concentrated in vacuo, yielding the crude product of general formula ([), e.g., 3-(1,1'-biphenyl]-4-ylsulfonyl)-N-[(1S)-3-hydroxy-1-phenylpropyl]-1,3-thiazolidine-2-carboxamide, as a white solid (6.21 g, 96%). Silica gel chromatography, eluting in isocratic conditions (50% ethyl acetate in hexanes), which gave the separation of the desired two pure diastereoisomers of general formula (I), e.g., (2S)-3-([1,1'-biphenyl]-4-ylsulfonyl)-N-[(1S)-3-hydroxy-1-phenylpropyl]-1,3-thiazolidine-2-carboxamide (more polar compound, 3.1 g), and (2R)-3-([1,1'-biphenyl]-4-ylsulfonyl)-N-[(1S)-3-hydroxy-1-phenylpropyl]-1,3-thiazolidine-2-carboxamide (less polar compound, 3.0 g).

Strategy 2:

a) Protocol for the N-Deprotection Step

Method A:

A solution was made containing a compound of general structure (V) (Intermediate 6, 0.788 g, 2.15 mmol), e.g., tert-butyl 2-({[(1S)-3-hydroxy-1-phenylpropyl]amino}carbonyl)-1,3-thiazolidine-3-carboxylate, in anhydrous DCM (50 ml). At 0° C., 4M HCl solution in dioxane (50 ml) was added, or alternatively, HCl gas, previously dried with a $H_2SO_4$ cc trap, was bubbled slowly through the reaction and deprotection was monitored by TLC using cyclohexane/ethyl acetate (1/1) and stained with a pancaldi solution. After approximately 45 minutes, TLC showed no remaining starting materiel and DCM was then evaporated in vacuo without heating to avoid salt decomposition. More DCM (20 ml) was then added and evaporated again in vacuo to remove remaining potential HCl (2-3 times). The desired product, e.g., N-[(1S)-3-hydroxy-1-phenylpropyl]-1,3-thiazolidine-2-carboxamide hydrochloride, was isolated as a white solid and used for the next step without further purification and characterization.

Method B:

In a 6 L 4-neck flask, was added a solution containing a compound of general structure (V) (Intermediate 6, 60 g g, 150.18 mmol), e.g., tert-butyl (2S)-2-({[(R)-phenyl(pyridin-2-yl)methyl]amino}carbonyl)-1,3-thiazolidine-3-carboxylate, in DCM under argon atmosphere (1250 ml). At −30° C., a solution of HCl conc. (627 mL, 7509 mmol) was added slowly during a period of 40 minutes. The reaction mixture was stirred at −30° C. for 3 h 30. The reaction was kept at −30° C. and a solution of 1 L of NAOH 1M was added followed by 1250 mL of NaOH 5M so that to obtain pH=5. The last 50 mL of 5M NaOH solution were added at −10° C. due to formation if ice in the flask. The slurry was extracted with DCM (5×500 mL) and dried over MgSO4 and evaporated to almost dryness. The desired product, e.g., (2S)—N—[(R)-phenyl(pyridin-2-yl)methyl]-1,3-thiazolidine-2-carboxamide hydrochloride, was isolated and used for the next step without further purification and shows no trace of racemisation.

b) Protocols for the N-Capping Step

Method A: To a solution of the product from the previous step, e.g., N-[(1S)-3-hydroxy-1-phenylpropyl]-1,3-thiazolidine-2-carboxamide hydrochloride (636 mg, 1 eq, 2.1 mmol) in DCM (50 ml) was added a compound of general structure (VI) (commercial or Intermediate 4, 543 mg, 1 eq, 2.15 mmol), e.g., [1,1'-biphenyl]-4-sulfonyl chloride, followed by TEA (1.74 g, 8 eq, 17.2 mmol) in dry DCM (50 ml) and the reaction mixture was stirred overnight at room temperature. Aminomethyl polystyrene resin (250 mg) was added to the reaction mixture and stirred for one hour before filtering at the pump. The solution was washed with citric acid (aq) (2×50 ml), then dried over $MgSO_4$, and evaporated in vacuo. The product of general structure (1), e.g., 3-([1,1'-biphenyl]-4-ylsulfonyl)-N-[(1S)-3-hydroxy-1-phenylpropyl]-1,3-thiazolidine-2-carboxamide, was purified by Silica gel chromatography, eluting in isocratic conditions (50% ethyl acetate in hexanes), which gave the separation of the desired two pure diastereoisomers of general formula (I), e.g., (2S)-3-([1,1'-biphenyl]-4-ylsulfonyl)-N-[(1S)-3-hydroxy-1-phenylpropyl]-1,3-thiazolidine-2-carboxamide (more polar compound, 300 mg) and (2R)-3-([1,1'-biphenyl]-4-ylsulfonyl)-N-[(1S)-3-hydroxy-1-phenylpropyl]-1,3-thiazolidine-2-carboxamide (less polar compound, 310 mg), corresponding to an overall yield of 60%.

Method B: To a solution of a compound of general structure (X) (commercial or Intermediate 4, 504 mg, 1 eq, 2.1 mmol), e.g., [1,1'-biphenyl]-4-sulfonic acid, in dry THF (20 ml), at 0° C., was drop wise added thionyl chloride (580 mg, 2 eq, 4.3 mmol) in dry THF solution (10 ml). The reaction mixture was stirred at room temperature over a 2 h period. The excess of thionyl chloride was then evaporated in vacuo and the crude product of general formula (VI), e.g., [1,1'-biphenyl]-4-sulfonyl chloride, was then directly added to a solution of N-[(1S)-3-hydroxy-1-phenylpropyl]-1,3-thiazolidine-2-carboxamide hydrochloride (636 mg, 1 eq, 2.1 mmol) in DCM (50 ml). To the reaction mixture, TEA (1.74 g, 17.2 mmol) was added in dry DCM (50 ml) and the reaction mixture was stirred overnight at room temperature. Aminomethyl polystyrene resin (250 mg) was added to the reaction mixture and stirred for one hour before filtering at the pump. The solution was washed with citric acid (aq) (2×50 ml) and then dried over $MgSO_4$, and evaporated in vacuo. The product of general structure (I), e.g., 3-([1,1'-biphenyl]-4-ylsulfonyl)-N-[(1S)-3-hydroxy-1-phenylpropyl]-1,3-thiazolidine-2-carboxamide, was purified by Silica gel chromatography, eluting in isocratic conditions (50% ethyl acetate in hexanes), which gave the separation of the desired two pure diastereoisomers of general formula (I), e.g., (2S)-3-([1,1'-biphenyl]-4-ylsulfonyl)-N—[(S)-3-hydroxy-1-phenylpropyl]-1,3-thiazolidine-2-carboxamide (more polar compound, 280 mg) and (2R)-3-([1,1'-biphenyl]-4-ylsulfonyl)-N-[(1S)-3-hydroxy-1-phenylpropyl]-1,3-thiazolidine-2-carboxamide (less polar compound, 300 mg), corresponding to an overall yield of 58%.

Method C: In a 3 L 4 necks flask was dissolved (2S)—N—[(R)-phenyl(pyridin-2-yl)methyl]-1,3-thiazolidine-2-carboxamide hydrochloride (50.4 g, 150 mmol) in 1800 mL of dry THF under argon at −30° C. When the temperature was reached, NMM (198 mL, 182 mmol) was added slowly, followed by (1.8 g, 15 mmol) of DMAP. The sulfonyl chloride, e.g., [1,1'-biphenyl]-4-sulfonyl chloride dissolved in 445 mL of anhydrous THF, was then added over a period of 30 min at −30° C. The reaction was stirred overnight and allow to warm to room temperature. The solvents were evaporated under vacuum (temperature of the bath=35° C.) and the resulting oily-solid slightly pink mixture was dissolved in 2 L of AcOEt and this mixture was extracted with 2×500 mL of $NH_4Cl$ sat, $NaHCO_3$ sat. and NaCl sat. The organic layer was dried over $MgSO_4$ and evaporated to give 100 g of crude product. No racemisation was detected by chiral HPLC (WhelkO1 (S,S) hexane/EtOH 5/5 0.1% TEA). The crude product was purified by flash chromatography to give 41.45 g of the desired product (2S)-3-(1,1'-biphenyl-4-ylsulfonyl)-N—[(R)-phenyl(pyridin-2-yl)methyl]-1,3-thiazolidine-2-carboxamide as a white solid. Yield: 53.5%.

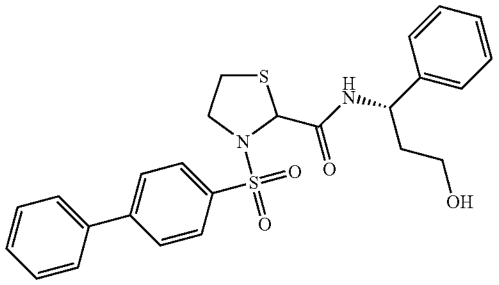 [SMILES: O=C(N[C@@H](CCO)c1ccccc1)C1SCCN1S(=O)(=O)c1ccc(-c2ccccc2)cc1]

(2S)-3-([1,1'-biphenyl]-4-ylsulfonyl)-N-[(1S)-3-hydroxy-1-phenylpropyl]-1,3-thiazolidine-2-carboxamide. $^1H$ NMR (300 MHz, $CDCl_3$); 1.8-2.3 (m, 2H), 2.55-3.15 (m, $CH_2S$, 2H), 3.6-3.60-4.0 (m, $CH_2N$, $CH_2O$, 4H), 5.2-5.3 (m, CH, 0.5H), 5.35 (s, CH, 0.5H), 5.37 (s, CH, 0.5H), 7.2-8.0 (m, CH(Ar), 14H); $M^+(ESI^+)$: 483.1; $M^-(ESI^-)$ 481.1.

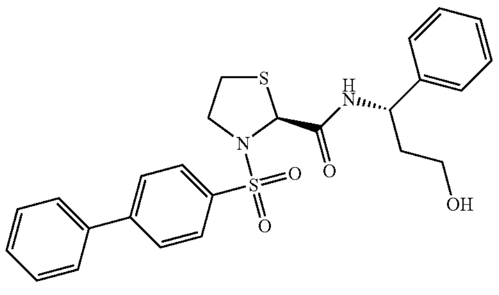 [SMILES: O=C(N[C@@H](CCO)c1ccccc1)[C@@H]1SCCN1S(=O)(=O)c1ccc(-c2ccccc2)cc1]

(2R)-3-([1,1'-biphenyl]-4-ylsulfonyl)-N-[(1S)-3-hydroxy-1-phenylpropyl]-1,3-thiazolidine-2-carboxamide. $^1H$ NMR (300 MHz, $CDCl_3$); 1.8-2.25 (m, 2H), 2.55-3.15 (m, $CH_2S$, 2H), 3.65-3.8 (m, $CH_2N$, 2H), 3.65-4.0 (m, $CH_2O$, 2H), 5.2 (m, CH, 1H), 5.36 (s, CH, 1H), 7.2-8.0 (m, CH(Ar), 14H); $M^+(ESI^+)$: 483.1; $M^-(ESI^-)$ 481.2.

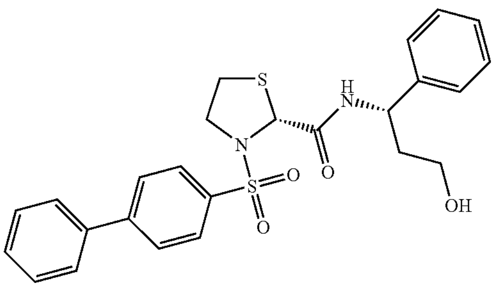

(2R)-3-([1,1'-biphenyl]-4-ylsulfonyl)-N-[(1S)-3-hydroxy-1-phenylpropyl]-1,3-thiazolidine-2-carboxamide. $^1H$ NMR (300 MHz, $CDCl_3$); 1.85-2.3 (m, 2H), 2.55-3.15 (m, $CH_2S$, 2H), 3.65-3.9 (m, $CH_2N$, $CH_2O$, 4H), 5.2-5.3 (m, CH, 1H), 5.37 (s, CH, 1H), 7.25-8.0 (m, CH(Ar), 14H); $M^+(ESI^+)$: 483.0; $M^-(ESI^-)$ 481.0.

Example 2

3-([1,1'-biphenyl]-4-ylsulfonyl)-N-[(1R)-2-hydroxy-1-phenylethyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and commercial (2R)-2-amino-2-phenylethanol, the title compound was obtained in 98% purity by HPLC.

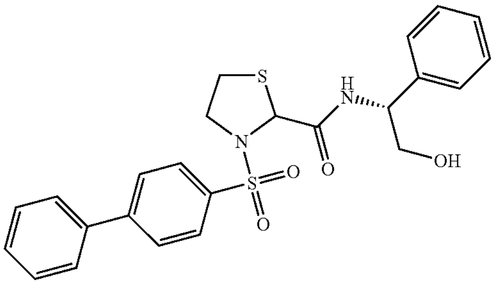 [SMILES: O=C(N[C@@H](CO)c1ccccc1)C1SCCN1S(=O)(=O)c1ccc(-c2ccccc2)cc1]

$^1H$ NMR (300 MHz, $CDCl_3$); 2.4-2.9 (m, $CH_2S$, 2H), 3.5-3.7 (m, $CH_2N$, 2H), 3.7-3.9 (m, $CH_2O$, 2H), 4.9 (m, CH, 1H), 5.2 (s, CH, 1H), 7.1-7.9 (m, CH(Ar), 14H); $M^+(ESI^+)$: 469.2; $M^-(ESI^-)$ 467.1.

Example 3

3-([1,1'-biphenyl]-4-ylsulfonyl)-N—[(R-phenyl(2-pyridinyl)methyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and (R)-phenyl(2-pyridinyl)methanamine (Intermediate 1), the title compound was obtained in 96% purity by HPLC.

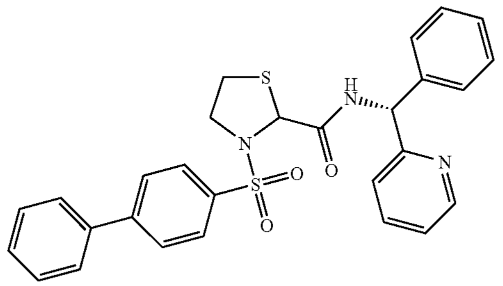 [SMILES: O=C(N[C@H](c1ccccc1)c1ccccn1)C1SCCN1S(=O)(=O)c1ccc(-c2ccccc2)cc1]

$^1$H NMR (300 MHz, $CDCl_3$); 2.5-3.0 (m, $CH_2S$, 2H), 3.6-4.0 (m, $CH_2N$, 2H), 5.41 (s, CH, 0.5H), 5.42 (s, CH, 0.5H), 6.07 (m, CH, 1H), 5.2 (s, CH, 1H), 7.1-7.8 (m, CH(Ar), 16H), 7.8-7.9 (m, CH, 1H), 8.5-8.6 (m, CH, 1H); $M^+(ESI^+)$: 516.3; $M^-(ESI^-)$ 514.1.

Example 4

3-([1,1'-biphenyl]-4-ylsulfonyl)-N-[1-(4-fluorophenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(4-fluorophenyl)-1-propanol (Intermediate 2), the title compound was obtained in 92% purity by HPLC.

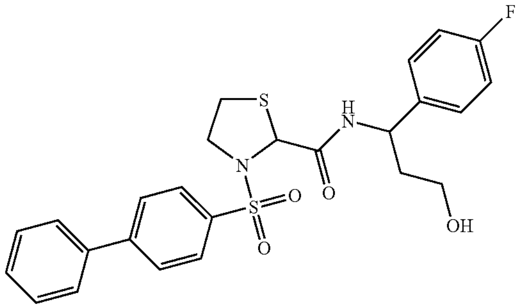 [SMILES: O=C(NC(CCO)c1ccc(F)cc1)C1SCCN1S(=O)(=O)c1ccc(-c2ccccc2)cc1]

$^1$H NMR (400 MHz, $CDCl_3$); 1.8-2.15 (m, $CH_2$, 2H), 2.5-2.9 (m, $CH_2S$, 2H), 3.5-3.8 (m, $CH_2N$, $CH_2O$, 4H), 5.15 (m, CH, 1H), 5.25 (s, CH, 1H), 7.1-7.9 (m, CH(Ar), 13H); $M^+(ESI^+)$: 501.3.

Example 5

3-([1,1'-biphenyl]-4-ylsulfonyl)-N-[1-(3-furyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(3-furyl)-1-propanol (Intermediate 2), the title compound was obtained in 98% purity by HPLC.

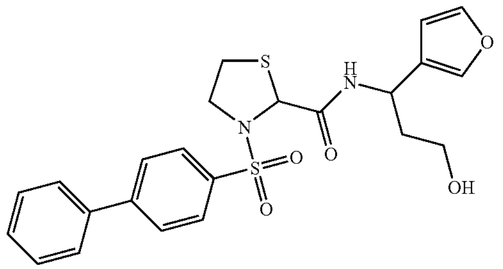 [SMILES: O=C(NC(CCO)c1ccoc1)C1SCCN1S(=O)(=O)c1ccc(-c2ccccc2)cc1]

$^1$H NMR (400 MHz, $CDCl_3$); 1.7-2.2 (m, $CH_2$, 2H), 2.5-2.9 (m, $CH_2S$, 2H), 3.6-3.8 (m, $CH_2N$, $CH_2O$, 4H), 5.12 (m, CH, 1H), 5.21 (s, CH, 1H), 6.25-6.35 (d, CH(furyl), 1H), 6.9-7.1 (m, CH(furyl), 1H), 7.3-7.9 (m, CH(Ar), 10H); $M^+(ESI^+)$: 473.1; $M^-(ESI^-)$: 471.1.

Example 6

3-([1,1'-biphenyl]-4-ylsulfonyl)-N-[1-(2-chlorophenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2-chlorophenyl)-1-propanol (Intermediate 2), the title compound was obtained in 94% purity by HPLC.

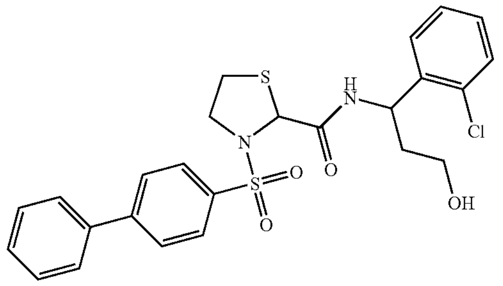 [SMILES: O=C(NC(CCO)c1ccccc1Cl)C1SCCN1S(=O)(=O)c1ccc(-c2ccccc2)cc1]

$^1$H NMR (400 MHz, $CDCl_3$); 1.95-2.15 (m, $CH_2$, 2H), 2.5-2.9 (m, $CH_2S$, 2H), 3.6-3.8 (m, $CH_2N$, $CH_2O$, 4H), 5.28 (s, CH, 0.5H), 5.29 (s, CH, 0.5H), 5.4-5.5 (m, CH, 1H), 7.1-7.9 (m, CH(Ar), 13H); $M^+(ESI^+)$: 517.3.

Example 7

3-([1,1'-biphenyl]-4-ylsulfonyl)-N-[1-(3-chlorophenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2-chlorophenyl)-1-propanol (Intermediate 2), the title compound was obtained in 99% purity by HPLC.

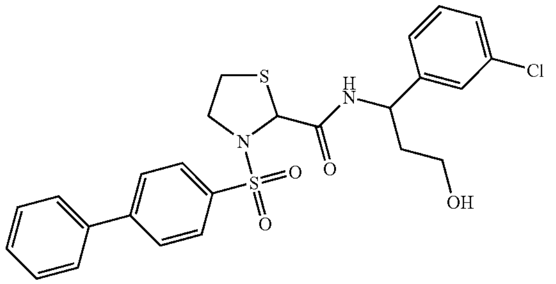 [SMILES: O=C(NC(CCO)c1cccc(Cl)c1)C1SCCN1S(=O)(=O)c1ccc(-c2ccccc2)cc1]

$^1$H NMR (400 MHz, $CDCl_3$); 1.8-2.2 (m, $CH_2$, 2H), 2.55-3.0 (m, $CH_2S$, 2H), 3.6-3.8 (m, $CH_2N$, $CH_2O$, 4H), 5.1-5.2 (m, CH, 1H), 5.24 (s, CH, 0.5H), 5.28 (s, CH, 0.5H), 7.2-7.9 (m, CH(Ar), 13H); $M^+$($ESI^+$): 517.1; $M^-$($ESI^-$): 514.8.

Example 8

N-[1-(1,3-benzodioxol-5-yl)-3-hydroxypropyl]-3-([1,1'-biphenyl]-4-ylsulfonyl)-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(1,3-benzodioxol-5-yl)-1-propanol (Intermediate 2), the title compound was obtained in 92% purity by HPLC.

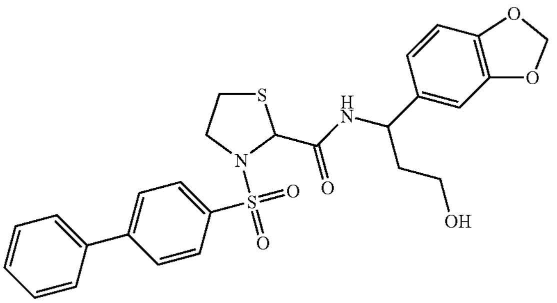 [SMILES: O=C(NC(CCO)c1ccc2c(c1)OCO2)C1SCCN1S(=O)(=O)c1ccc(-c2ccccc2)cc1]

$^1$H NMR (400 MHz, $CDCl_3$); 1.7-2.2 (m, $CH_2$, 2H), 2.45-3.0 (m, $CH_2S$, 2H), 3.6-3.95 (m, $CH_2N$, $CH_2O$, 4H), 5.0-5.1 (m, CH, 1H), 5.26 (s, CH, 0.5H), 5.28 (s, CH, 0.5H), 5.87 (s, CH, 1H), 5.89 (s, CH, 1H), 6.8-7.9 (m, CH(Ar), 12H); $M^+$($ESI^+$): 527.1; $M^-$($ESI^-$): 525.0.

Example 9

(2S)-3-[(4-tert-butylphenyl)sulfonyl]-N-[(1S-3-hydroxy-1-phenylpropyl]-1,3-thiazolidine-2-carboxamide Following the general strategies and protocols outlined in Example 1, starting from 3-[(4-tert-butylphenyl)sulfonyl]-1,3-thiazolidine-2-carboxylic acid (Intermediate 8) and commercial (3S)-3-amino-3-phenyl-1-propanol, the title compound was obtained in 98% purity by HPLC.

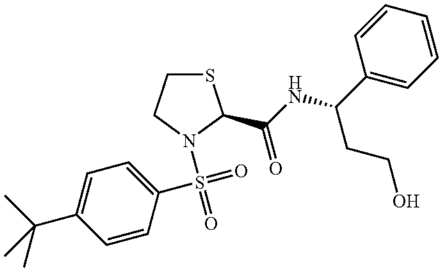 [SMILES: CC(C)(C)c1ccc(S(=O)(=O)N2CCS[C@H]2C(=O)N[C@@H](CCO)c2ccccc2)cc1]

$^1$H NMR (400 MHz, $CDCl_3$); 1.27 (s, $CH_3$, 9H), 1.65-2.15 (m, $CH_2$, 2H), 2.45-2.95 (m, $CH_2S$, 2H), 3.6-3.95 (m, $CH_2N$, $CH_2O$, 4H), 5.1-5.2 (m, CH, 1H), 5.26 (s, CH, 1H), 7.3-7.7 (m, CH(Ar), 9H); $M^+$($ESI^+$): 463.1; $M^-$($ESI^-$): 461.6.

Example 10

(2S)—N-[(1S)-3-hydroxy-1-phenylpropyl]-3-[(4-tert-pentylphenyl)sulfonyl]-1,3-thiazolidine-2-carboxamide Following the general strategies and protocols outlined in Example 1, starting from 3-[(4-tert-pentylphenyl)sulfonyl]-1,3-thiazolidine-2-carboxylic acid (Intermediate 8) and commercial (3S)-3-amino-3-phenyl-1-propanol, the title compound was obtained in 99% purity by HPLC.

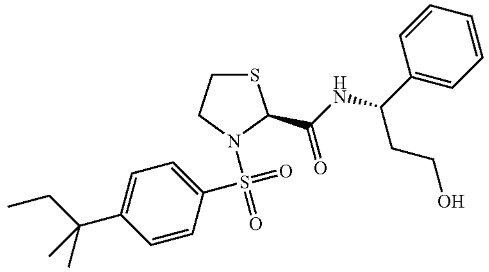 [SMILES: CCC(C)(C)c1ccc(S(=O)(=O)N2CCS[C@H]2C(=O)N[C@@H](CCO)c2ccccc2)cc1]

$^1$H NMR (400 MHz, $CDCl_3$); 0.63 (t, J=7.3 Hz, 3H), 1.29 (s, $CH_3$, 6H), 1.65 (q, J=7.4 Hz, 2H), 1.88 (m, $CH_2$, 1H), 2.19 (m, $CH_2$, 1H), 2.5 (m, $CH_2S$, 1H), 2.94 (dt, J=12 Hz and 5.6 Hz, $CH_2S$, 1H), 3.65-3.87 (m, $CH_2N$, $CH_2O$, 4H), 5.2 (td, J=6.6 Hz and 3.8 Hz, CH, 1H), 5.32 (s, CH, 1H), 7.25-7.8 (m, CH(Ar), 9H); $M^+$($ESI^-$): 477.2; $M^-$($ESI^-$): 475.0.

Example 11

3-([1,1'-biphenyl]-4-ylsulfonyl)-N-[1-(2-fluorophenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2-fluorophenyl)-1-propanol (Intermediate 2), the title compound was obtained in 96% purity by HPLC.

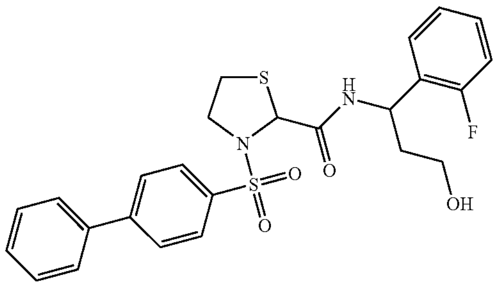 [SMILES: O=C(NC(CCO)c1ccccc1F)C1SCCN1S(=O)(=O)c1ccc(-c2ccccc2)cc1]

$^{1}H$ NMR (400 MHz, $CDCl_3$); 2.24 (m, 3H), 2.25 (m, 1H), 2.95 (m, 1H), 3.63-3.90 (m, 4H), 5.31 (m, 2H), 6.99-7.86 (m, 13H).; $M^+(ESI^+)$: 501; $M^-(ESI^-)$: 499.

Example 12

3-([1,1'-biphenyl]-4-ylsulfonyl)-N-[1-(2-methylphenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2-methylphenyl)-1-propanol (Intermediate 2), the title compound was obtained in 98% purity by HPLC.

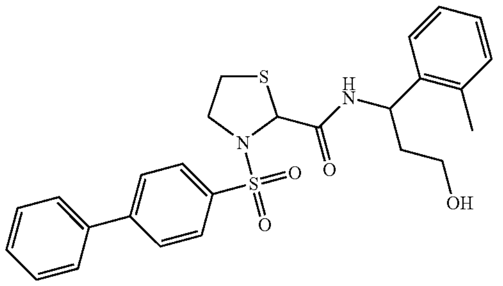 [SMILES: Cc1ccccc1C(CCO)NC(=O)C1SCCN1S(=O)(=O)c1ccc(-c2ccccc2)cc1]

$^{1}H$ NMR (300 MHz, $CDCl_3$); 1.86 (m, 1H), 2.09 (m, 1H), 2.36 (s, 3H), 2.57 (m, 1H), 2.99 (m, 1H), 3.72-3.92 (m, 4H), 5.31-5.40 (m, 2H), 7.19-7.88 (m, 13H); $M^+(ESI^+)$: 497; $M^-(ESI^-)$: 495.

Example 13

3-([1,1'-biphenyl]-4-ylsulfonyl)-N-[1-(2-methoxyphenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2-methoxyphenyl)-1-propanol (Intermediate 2), the title compound was obtained in 87% purity by HPLC.

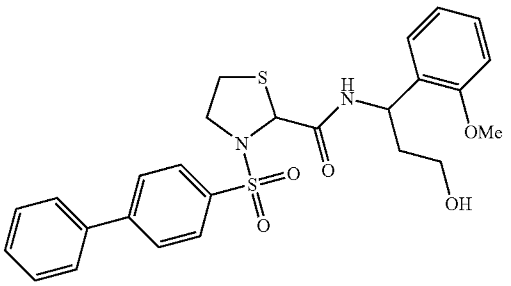 [SMILES: COc1ccccc1C(CCO)NC(=O)C1SCCN1S(=O)(=O)c1ccc(-c2ccccc2)cc1]

$^{1}H$ NMR (300 MHz, $CDCl_3$); 2.00 (m, 2H), 2.57 (m, 1H), 2.87-2.98 (m, 2H), 3.62-3.70 (m, 3H), 3.92 (m, 0.4H), 3.92 (s, 1.8H), 3.98 (s, 1.2H), 4.04 (m, 0.6H), 5.23 (m, 1H), 5.43 (m, 1H), 6.92 (m, 2H), 7.22-7.45 (m, 2H), 7.46 (m, 3H), 7.60 (m, 2H), 7.77 (m, 2H), 7.90 (m, 2H), 8.26 (d, J=11.7 Hz, 0.6H), 8.47 (d, J=9.8 Hz, 0.4H); $M^+(ESI^+)$: 513; $M^-(ESI^-)$: 511.

Example 14

3-([1,1'-biphenyl]-4-ylsulfonyl)-N-[1-(2,6-difluorophenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2,6-difluorophenyl)-1-propanol (Intermediate 2), the title compound was obtained in 80% purity by HPLC.

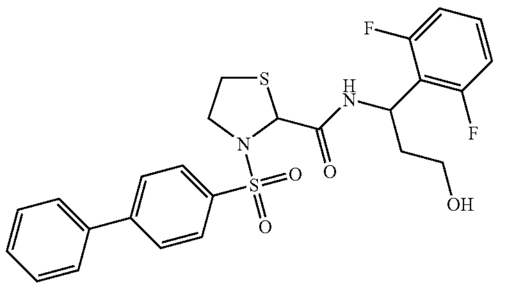 [SMILES: O=C(NC(CCO)c1c(F)cccc1F)C1SCCN1S(=O)(=O)c1ccc(-c2ccccc2)cc1]

$^{1}H$ NMR (300 MHz, $CDCl_3$); 2.01 (m, 2H), 2.69 (m, 1H), 3.00 (m, 1H), 3.69-3.96 (m, 4H), 4.32 (m, 0.5H), 5.36 (m, 1H), 5.62 (m, 1H), 6.91-7.91 (m, 13H).; $M^+(ESI^+)$: 519; $M^-(ESI^-)$: 517.

Example 15

3-([1,1'-biphenyl]-4-ylsulfonyl)-N-[1-(2,4-dimethylphenyl)-3-hydroxypropyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 3-amino-3-(2,4-dimethylphenyl)-1-propanol (Intermediate 2), the title compound was obtained in 94.9% purity by HPLC.

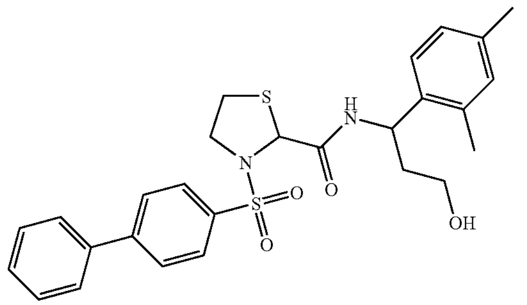 [SMILES: Cc1ccc(C(CCO)NC(=O)C2SCCN2S(=O)(=O)c2ccc(-c3ccccc3)cc2)c(C)c1]

$^1H$ NMR (300 MHz, $CDCl_3$); 1.94 (m, 1H), 2.09 (m, 1H), 2.30 (m, 6H), 2.56 (m, 1H), 2.87 (m, 0.5H), 2.99 (m, 0.5H), 3.70 (m, 3H), 391 (m, 1H), 5.31-5.37 (m, 2H), 6.76 (m, 2H), 6.99 (m, 2H), 7.45-7.93 (m, 9H).; $M^-(ESI^-)$: 511. $M^-(ESI^-)$: 509.

Example 16

General protocols for the solution-phase synthesis of 1,3-thiazolidine-2-carboxamide derivatives of general formula (I) from intermediates of general formula (XXVIII) (Intermediates 8)

Methods for the nucleophile substitution of the mesylate group in compounds of general structure (XXVIII) (Intermediate 9) by primary or secondary amines include:

Method A (Displacement by Secondary Amines):

The mesylate derivative of general formula (XXVIII) (Intermediate 8, 1 eq.) and LiBr (1.5 eq) were dissolved in a mixture of acetonitrile/2-butanone (1:1) (e.g., dilution 500 mg in 10 ml of solvents) and agitated for 20 min at room temperature. To this solution was added TEA (1 eq) and the amine of general structure $HNR^5R^6$ (3-4 eq) in 10 ml acetonitrile/2-butanone (1:1). The reaction mixture was heated at reflux (80° C.) for 16 h. The reaction mixture was cooled down to room temperature and evaporated in vacuo, redissolved in EtOAc (50 ml) and washed with an aqueous solution of $NaHCO_3$ sat. The organic phase was dried over $Na_2SO_4$. The crude product of general formula (I) was purified on FC with an appropriated gradient EtOAc: CycloHexane: MeOH.

Method B (Displacement by Primary Amines):

The mesylate derivative of general formula (XXVIII) (Intermediate 8, 1 eq.) was dissolved in dry THF (e.g., dilution 760 mg in 76 ml of THF). Sodium iodide (10 eq.), anhydrous potassium carbonate (2 eq.) and the amine of general structure $HNR^5R^6$ (3.5 eq.) were added and the reaction mixtures were shaken at room temperature for 6 days. Potassium carbonate and sodium iodide were filtered and the THF evaporated. The residue was dissolved in DCM and Ameba (aminomethylbenzylaldehyde) resin (2 eq.) was added to the flask. The reaction was shaken at room temperature over night. The resin was filtered and the solvent removed. The compounds were analyzed by LC-MS. When the purity was <60%, the compound was further purified using amberlyst 15 resin in MeOH. The reaction mixture was shaken at room temperature for 2 days. The resin was filtered and washed with methanol. The final product of general structure (1) was then released using concentrated HCl/MeOH (1/1) over night.

Example 17

(2S)-3-([1,1'-biphenyl]-4-ylsulfonyl)-N-{(1S)-3-[(2-furylmethyl)(methyl)-amino]-1-phenylpropyl}-1,3-thiazolidine-2-carboxamide Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and 2-furyl-N-methyl-methanamine, the title compound was obtained in 98.2% purity by HPLC.

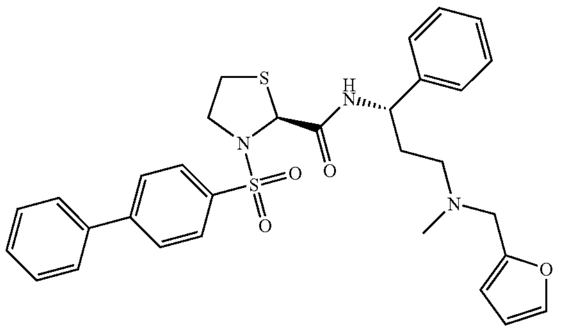 [SMILES: CN(CC[C@H](NC(=O)[C@@H]1SCCN1S(=O)(=O)c1ccc(-c2ccccc2)cc1)c1ccccc1)Cc1ccco1]

$^1H$ NMR (300 MHz, $CDCl_3$); $^1H$ NMR (300 MHz, $CDCl_3$); 1.85-2.2 (m, 2H), 2.5 (s, $CH_3N$, 3H), 2.45-3.00 (m, $CH_2S$, 2H), 2.7-3.0 (m, $CH_2N$, 2H), 3.6 (m, $CH_2N$, 2H), 4.2 (m, $CH_2N$, 2H), 4.7 (m, CH, 1H), 5.3 (s, CH, 1H), 6.37 (m, CH(furyl), 1H), 6.56 (m, CH(furyl), 1H), 7.05-8.0 (m, CH(Ar), 15H), 8.7 (m, NH, 1H); $M^+(ESI^+)$: 576.1; $M^-(ESI^-)$: 573.8.

Example 18

(2S)-3-([1,1'-biphenyl]-4-ylsulfonyl)-N-[(1S)-3-(diethylamino)-1-phenyl-propyl]-3-thiazolidine-2-carboxamide Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and N,N-diethylamine, the title compound was obtained in 98.6% purity by HPLC.

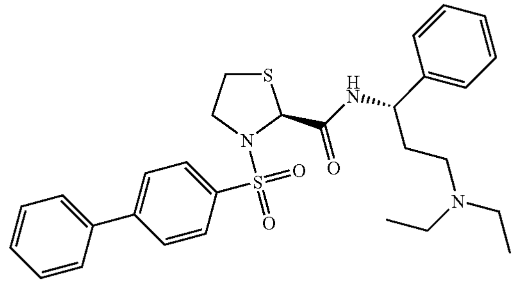 [SMILES: CCN(CC)CC[C@H](NC(=O)[C@@H]1SCCN1S(=O)(=O)c1ccc(-c2ccccc2)cc1)c1ccccc1]

$^1H$ NMR (400 MHz, DMSO); 1.05 (t, J=7.3 Hz, 6H), 1.88 (m, $CH_2$, 2H), 2.79-2.81 (m, $CH_2N$, 6H), 3.05 (m, $CH_2S$, 1H), 3.05-3.50 (broad, $H_2O$), 3.81 (m, $CH_2N$, 2H), 4.86 (td, J=6.6 Hz and 3.8 Hz, CH, 1H), 5.44 (s, CH, 1H), 6.58 (s, $CH_2$, 2H), 7.24-7.33 (m, CH(Ar), 5H); 7.53 (m, CH(Ar), 3H), 7.76 (m, CH(Ar), 2H), 7.95 (m, CH(Ar), 4H), 8.68 (m, 1H, NH); $M^+(ESI^+)$: 538.0; $M^-(ESI^-)$; 536.0.

Example 19

(2S)—N-{(1S3-[benzyl(methyl)amino]-1-phenylpropyl}-3-([1,1'-biphenyl]-4-ylsulfonyl)-1,3-thiazolidine-2-carboxamide Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and N-methyl(phenyl) methanamine, the title compound was obtained in 98% purity by HPLC.

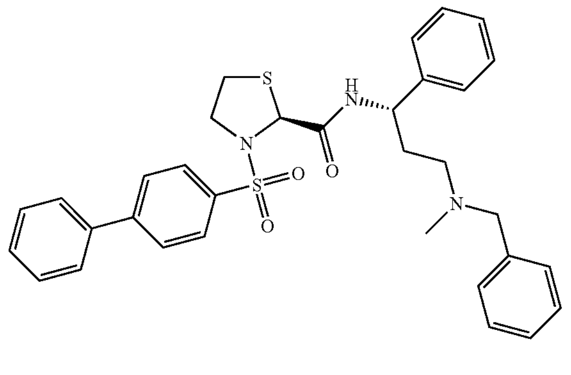 [SMILES: CN(CC[C@H](NC(=O)[C@@H]1SCCN1S(=O)(=O)c1ccc(-c2ccccc2)cc1)c1ccccc1)Cc1ccccc1]

$^1$H NMR (300 MHz, $CDCl_3$); 1.75-2.1 (m, 2H), 2.2 (s, $CH_3N$, 3H), 2.3-2.9 (m, $CH_2S$, 2H), 3.3-3.5 (m, $CH_2N$, 2H), 3.6 (s, $CH_2N$, 2H), 3.9 (m, $CH_2N$, 2H), 5.0 (m, CH, 1H), 5.3 (s, CH, 1H), 7.0-8.0 (m, CH(Ar), 19H), 8.6 (m, NH, 1H); $M^+(ESI^+)$: 586.2; $M^-(ESI^-)$: 583.8.

Example 20

(2S)-3-([1,1'-biphenyl]-4-ylsulfonyl)-N-((15)-3-{methyl[2-(2-pyridinyl)ethyl]-amino}-1-phenylpropyl)-1,3-thiazolidine-2-carboxamide Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and N-methyl-2-(2-pyridinyl)ethanamine, the title compound was obtained in 100% purity by HPLC.

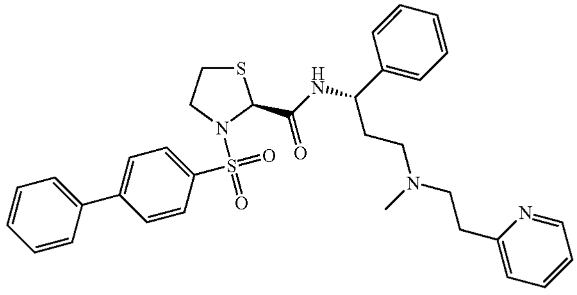 [SMILES: CN(CCc1ccccn1)CC[C@H](NC(=O)[C@@H]1SCCN1S(=O)(=O)c1ccc(-c2ccccc2)cc1)c1ccccc1]

$^1$H NMR (400 MHz, DMSO); 1.75 (m, $CH_2$, 6H), 2.18 (s, $CH_3$, 3H), 2.36 (m, CH, 1H), 2.50 (m, CHS, 1H), 2.55-2.85 (m, CH, 3H), 2.95 (m, CHS, 1H), 2.37 (m, $CH_2$, 2H), 3.67-3.74 (m, 2H, $CH_2N$), 4.70 (s, CH, 1H), 5.34 (s, CH, 1H), 6.47 (s, 2H, H vinyl), 7.14-7.25 (m, CH(Ar), 7H); 7.40-7.49 (m, CH(Ar), 3H), 7.50-7.70 (m, CH(Ar), 3H), 7.83 (m, CH(Ar), 4H), 8.33 (m, CH(Ar), 1H), 8.58 (m, 1H, NH); $M^+(ESI^+)$: 601; $M^-(ESI^-)$: 599

Example 21

(2S)-3-([1,1'-biphenyl]-4-ylsulfonyl)-N-{(1S)-3-[(2-hydroxyethyl)(methyl)-amino]-1-phenylpropyl}-1,3-thiazolidine-2-carboxamide Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and 2-(methylamino) ethanol, the title compound was obtained in 94.3% purity by HPLC.

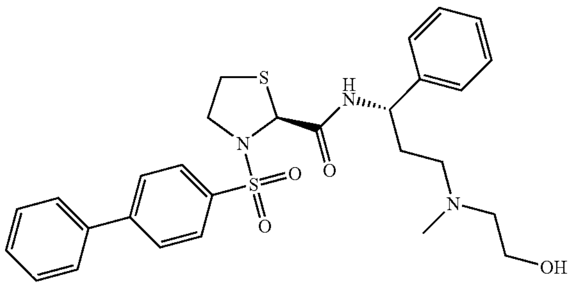 [SMILES: CN(CCO)CC[C@H](NC(=O)[C@@H]1SCCN1S(=O)(=O)c1ccc(-c2ccccc2)cc1)c1ccccc1]

$^1$NMR (300 MHz, $CDCl_3$); 1.8-2.2 (m, 2H), 2.36 (s, $CH_3N$, 3H), 2.45-3.05 (m, $CH_2S$, 2H), 2.6-2.7 (m, $CH_2N$, 4H), 3.7 (m, $CH_2O$, 2H), 3.7-4.1 (m, $CH_2N$, 2H), 5.1-5.25 (m, CH, 1H), 5.48 (s, CH, 1H), 7.25-8.0 (m, CH(Ar), 14H), 8.55 (m, NH, 1H); $M^+(ESI^+)$: 540.2; $M^-$ $(ESI^-)$: 537.99.

Example 22 methyl[[(3S)-3-({[(2S)-3-([1,1'-biphenyl]-4-ylsulfonyl)-1,3-thiazolidin-2-yl]carbonyl}amino)-3-phenylpropyl](methyl)amino]acetate Following the general method A as outlined in Example 16, starting from (3S)-3-({[(2S)-3-([1,1'-biphenyl]-4-ylsulfonyl)-1,3-thiazolidin-2-yl]carbonyl}amino)-3-phenylpropyl methanesulfonate (Intermediate 9) and methyl(methylamino)acetate, the title compound was obtained in 98.9% purity by HPLC.

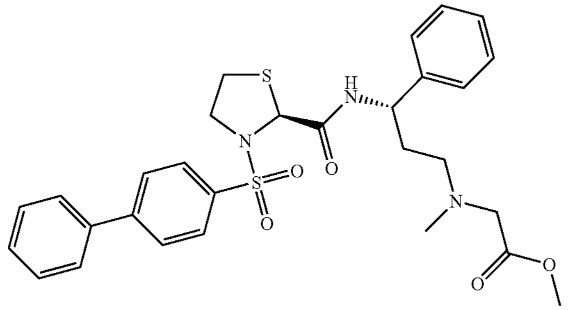 [SMILES: COC(=O)CN(C)CC[C@H](NC(=O)[C@@H]1SCCN1S(=O)(=O)c1ccc(-c2ccccc2)cc1)c1ccccc1]

$^1$H NMR (300 MHz, $CDCl_3$); 1.8-2.2 (m, 21H), 2.4 (s, $CH_3N$, 3H), 2.5-3.0 (m, $CH_2S$, 2H), 2.6-2.7 (m, $C_{1-2}N$, 21H), 3.4 (s, $CH_2N$, 2H), 3.69 (s, $CH_3O$, 3H), 3.7-4.0 (m, $CH_2N$, 2H), 5.1 (m, CH, 1H), 5.49 (s, CH, 1H), 7.2-8.0 (m, CH(Ar), 141H), 8.6 (m, NH, 1H); $M^+(ESI^+)$: 568.2; $M^-(ESI^-)$: 565.8.

Example 23

3-([1,1'-biphenyl]-4-ylsulfonyl)-N-[1-phenyl-3-(1-pyrrolidinyl)propyl]-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and pyrrolidine, the title compound was obtained in 99.2% purity by HPLC.

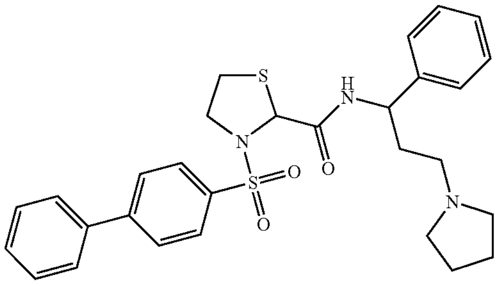 [SMILES: O=C(NC(CCN1CCCC1)c1ccccc1)C1SCCN1S(=O)(=O)c1ccc(-c2ccccc2)cc1]

$^1$H NMR (300 MHz, $CDCl_3$); 2.15-2.4 (m, $CH_2$, 6H), 2.45-3.05 (m, $CH_2S$, 2H), 2.5-3.5 (m, $CH_2N$, 6H), 3.9-4.25 (m, $CH_2N$, 2H), 5.2 (m, CH, 1H), 5.5 (s, CH, 1H), 7.2-8.0 (m, CH(Ar), 14H), 8.5 (m, NH, 1H); $M^+(ESI^+)$: 536.3; $M^-(ESI^-)$: 534.2.

Example 24

3-([1,1'-biphenyl]-4-ylsulfonyl)-N-[3-(dimethylamino)-1-phenylpropyl]-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and N,N-dimethylamine, the title compound was obtained in 99.6% purity by HPLC.

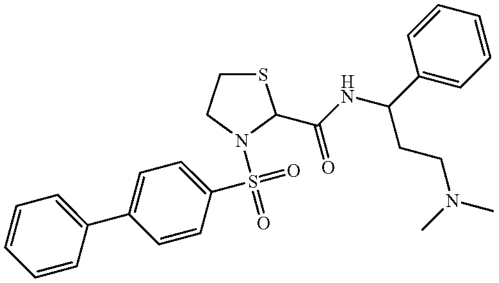 [SMILES: CN(C)CCC(NC(=O)C1SCCN1S(=O)(=O)c1ccc(-c2ccccc2)cc1)c1ccccc1]

$^1$H NMR (300 MHz, $CDCl_3$); 2.2-2.7 (m, $CH_2$, 2H), 2.45-3.00 (m, $CH_2S$, 2H), 2.7 (s, $CH_3N$, 3H), 2.9 (s, $CH_3N$, 3H), 3.5-3.9 (m, $CH_2N$, 2H), 4.0-4.25 (m, $CH_2N$, 2H), 5.0 (m, CH, 1H), 5.3 (s, CH, 1H), 7.2-8.0 (m, CH (Ar), 14H), 8.5 (m, NH, 1H); $M^+(ESI^+)$: 510.2; $M^-(ESI^-)$: 508.1.

Example 25

N-[3-(1-azepanyl)-1-phenylpropyl]-3-([1,1'-biphenyl]-4-ylsulfonyl)-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and azepane, the title compound was obtained in 99.1% purity by HPLC.

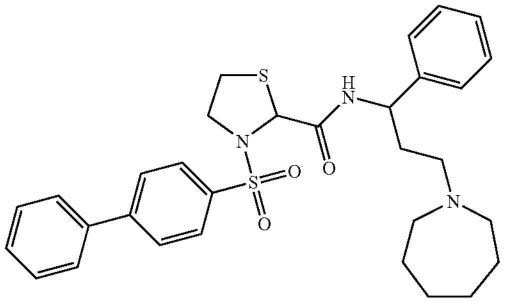 [SMILES: O=C(NC(CCN1CCCCCC1)c1ccccc1)C1SCCN1S(=O)(=O)c1ccc(-c2ccccc2)cc1]

$M^+(ESI^+)$: 564.3; $M^-(ESI^-)$: 562.3.

Example 26

3-([1,1'-biphenyl]-4-ylsulfonyl)-N-[1-phenyl-3-(1-piperidinyl)propyl]-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and piperidine, the title compound was obtained in 99.5% purity by HPLC.

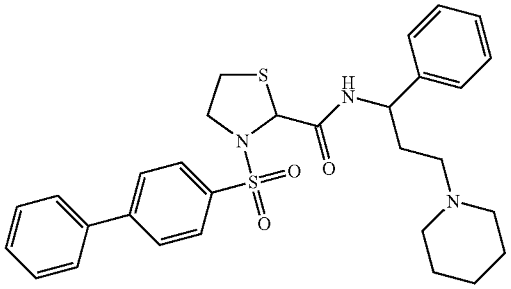 [SMILES: O=C(NC(CCN1CCCCC1)c1ccccc1)C1SCCN1S(=O)(=O)c1ccc(-c2ccccc2)cc1]

$M^+(ESI^+)$: 550.3; $M^-(ESI^-)$: 548.2.

Example 27

3-([1,1'-biphenyl]-4-ylsulfonyl)-N-[3-(4-morpholinyl)-1-phenylpropyl]-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and morpholine, the title compound was obtained in 99.3% purity by HPLC.

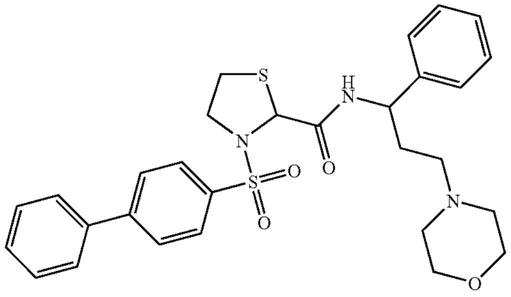 [SMILES: O=C(NC(CCN1CCOCC1)c1ccccc1)C1SCCN1S(=O)(=O)c1ccc(-c2ccccc2)cc1]

$M^+(ESI^+)$: 552.3; $M^-(ESI^-)$: 550.2.

Example 28

3-([1,1'-biphenyl]-4-ylsulfonyl)-N-{3-[(2-hydroxy-2-phenylethyl)(methyl)-amino]-1-phenylpropyl}-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and 2-(methylamino)-1-phenylethanol, the title compound was obtained in 82% purity by HPLC.

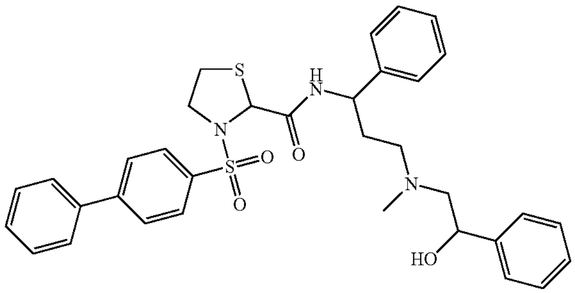 [SMILES: CN(CCC(NC(=O)C1SCCN1S(=O)(=O)c1ccc(-c2ccccc2)cc1)c1ccccc1)CC(O)c1ccccc1]

$M^+(ESI^+)$: 616.3; $M^-(ESI^-)$: 614.9.

Example 29

3-([1,1'-biphenyl]-4-ylsulfonyl)-N-{3-[(3-hydroxy-3-phenylpropyl)(methyl)-amino]-1-phenylpropyl}-1,3-thiazolidine-2-carboxamide Following the general method A as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and 3-(methylamino)-1-phenyl-1-propanol, the title compound was obtained in 85% purity by HPLC.

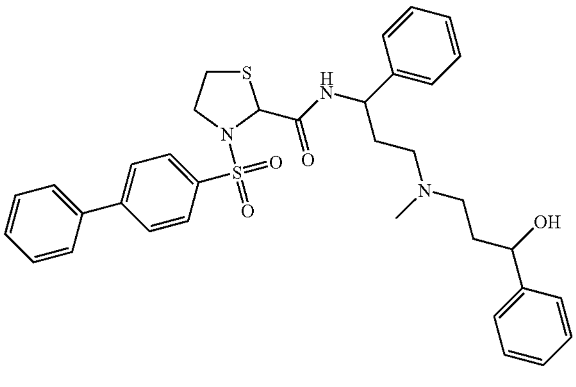 [SMILES: CN(CCC(O)c1ccccc1)CCC(NC(=O)C1SCCN1S(=O)(=O)c1ccc(-c2ccccc2)cc1)c1ccccc1]

$M^+(ESI^+)$: 630.4; $M^-(ESI^-)$: 628.2.

Example 30

3-([1,1'-biphenyl]-4-ylsulfonyl)-N-{3-[(2-hydroxycyclohexyl)amino]-1-phenylpropyl}-1,3-thiazolidine-2-carboxamide Following the general method B as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and 2-aminocyclohexanol, the title compound was obtained in 99% purity by HPLC.

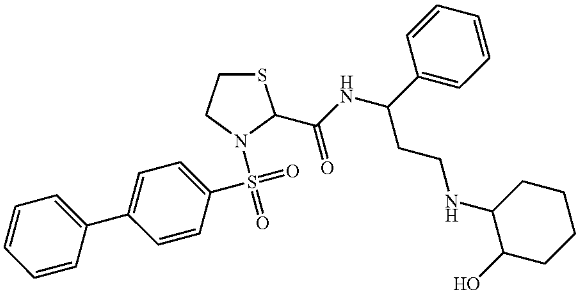 [SMILES: O=C(NC(CCNC1CCCCC1O)c1ccccc1)C1SCCN1S(=O)(=O)c1ccc(-c2ccccc2)cc1]

$M^+(ESI^+)$: 580.6; $M^-(ESI^-)$: 578.8.

Example 31

N-[3-(benzylamino)-1-phenylpropyl]-3-([1,1'-biphenyl]-4-ylsulfonyl)-1,3-thiazolidine-2-carboxamide Following the general method B as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and benzylamine, the title compound was obtained in 99% purity by HPLC.

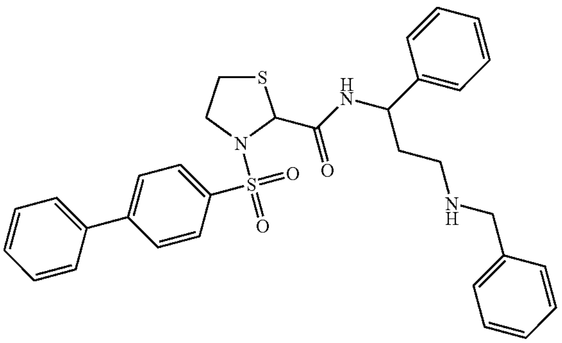 [SMILES: O=C(NC(CCNCc1ccccc1)c1ccccc1)C1SCCN1S(=O)(=O)c1ccc(-c2ccccc2)cc1]

$M^+(ESI^+)$: 571.8; $M^-(ESI^-)$: 569.99.

Example 32

3-([1,1'-biphenyl]-4-ylsulfonyl)-N-(1-phenyl-3-{[2-(2-pyridinyl)ethyl]-amino}propyl)-1,3-thiazolidine-2-carboxamide Following the general method B as outlined in Example 16, starting from 3-({[3-([1,1'-biphenyl]-4-ylsulfonyl)-1,3-thiazolidin-2-yl]carbonyl}amino)-3-phenylpropyl methanesulfonate (Intermediate 9) and 2-(2-pyridinyl)ethanamine, the title compound was obtained in 97.4% purity by HPLC.

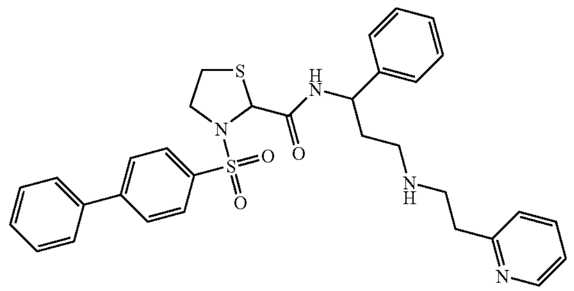 [SMILES: O=C(NC(CCNCCc1ccccn1)c1ccccc1)C1SCCN1S(=O)(=O)c1ccc(-c2ccccc2)cc1]

$M^+(ESI^+)$: 586.9; $M^-(ESI^-)$: 585.3.

Example 33

General protocols for the solid-phase synthesis of 1,3-thiazolidine-2-carboxamide derivatives of general formula (I)

a) Loading step

A solution of an suitably protected intermediate of general formula (III), e.g., 3-(tert-butoxycarbonyl)-1,3-thiazolidine-2-carboxylic acid (8.6 g, 35.7 mmol) in dry DCM (100 ml) was added to Kaiser oxime resin (10 g, 11.9 mmol) suspended in dry DCM (100 ml). Diisopropylcarbodiimide (4.5 g, 35.7 mmol) was then added to the suspension and shaken overnight at ambient temperature. The resin was then filtered at the pump and washed sequentially with NMP, DCM, MeOH and finally diethyl ether before being dried at 40° C. in vacuo.

b) N-deprotection step

The resin obtained in the previous loading step was shaken with a 20% solution of trifluoroacetic acid in dichloromethane (100 ml) for 30 minutes prior to filtering at the pump and washing sequentially with aliquots of NMP, DCM, MeOH and finally diethyl ether before being dried at room temperature in vacuo.

c) N-capping step

The resin from the previous deprotection step was transferred into a 96-well filter-plate (approx. 50 mg of dry resin/well; Loading 0.93 mmol/g; 0.047 mmol) and each well treated with a sulfonyl chloride (VI) (0.140 mmol, 3 eq) and diisopropylethylamine (0.140 mmol, 3 eq) in NMP (1 ml), overnight. The plate was then sealed and shaken overnight at ambient temperature. After this time, the resin aliquots were filtered, washed sequentially with aliquots of NMP, DCM and finally diethyl ether before being dried at room temperature in vacuo.

d) Cleavage Step

Amines (IV) (e.g., from commercial sources, or Intermediates 1 or Intermediates 2, 0.042 mmol) were added to suspensions of the functionalised oxime resin batches from the previous step (50 mg, 0.047 mmol) in DCM (0.5-1 ml), and the plates sealed and shaken over the weekend period (~66 hours) at ambient temperatures. After filtration, the resultant solvent was evaporated in vacuo to give the products of general formula (I), which were analyzed by HPLC and mass spectroscopy. In cases where an N-Boc-protecting group was present on the final product, a solution of 25% TFA in DCM (3 ml) was added to the crude compound and stirred at ambient temperatures for 40 min. The solvent was then removed in vacuo to give the corresponding final, N-deprotected products, again of general formula (I).

Example 34

N-benzyl-3-([1,1'-biphenyl]-4-ylsulfonyl)-1,3-thiazolidine-2-carboxamide

Following the general solid phase method as outlined Example 33, starting from 3-(tert-butoxycarbonyl)-1,3-thiazolidine-2-carboxylic acid, Kaiser oxime resin, [1,1'-biphenyl]-4-sulfonyl chloride and benzylamine, the title compound was obtained in 97% purity by HPLC.

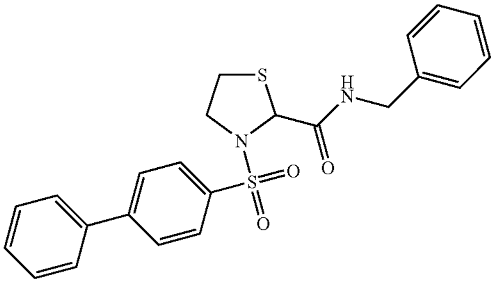 [SMILES: O=C(NCc1ccccc1)C1SCCN1S(=O)(=O)c1ccc(-c2ccccc2)cc1]

$^1H$ NMR (400 MHz, $CDCl_3$); 2.6-3.1 (m, $CH_2S$, 2H), 3.7-4.1 (m, $CH_2N$, 2H), 4.6-4.7 (m, $NCH_2Ar$, 2H), 5.6 (s, CH, 1H), 7.3-8.15 (m, CH(Ar), 14H); $M^+(ESI^+)$: 439.1; $M^-(ESI^-)$: 437.0.

Example 35

N-benzyl-3-[(4-tert-butylphenyl)sulfonyl]-1,3-thiazolidine-2-carboxamide

Following the general solid phase method as outlined Example 33, starting from 3-(tert-butoxycarbonyl)-1,3-thiazolidine-2-carboxylic acid, Kaiser oxime resin, 4-tert-butylbenzenesulfonyl chloride and benzylamine, the title compound was obtained in 97.1% purity by HPLC.

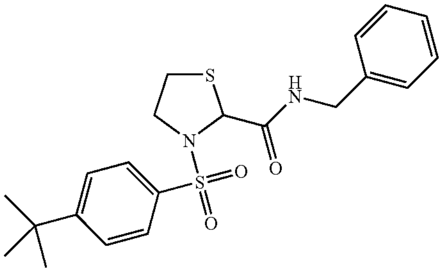 [SMILES: CC(C)(C)c1ccc(S(=O)(=O)N2CCSC2C(=O)NCc2ccccc2)cc1]

$^1H$ NMR (300 MHz, $CDCl_3$); 1.1 (s, $CH_3$, 3H), 2.3-2.8 (m, $CH_2S$, 2H), 3.5-3.8 (m, $CH_2N$, 2H), 4.2-4.4 (m, $NCH_2Ar$, 2H), 5.2 (s, CH, 1H), 7.0-7.65 (m, CH(Ar), 9H); $M^+(ESI^+)$: 419.8; $M^-(ESI^-)$: 417.4.

Example 36

3-([1,1'-biphenyl]-4-ylsulfonyl)-N-(4-methoxybenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 4-methoxyphenyl)methanamine, the title compound was obtained in 98% purity by HPLC.

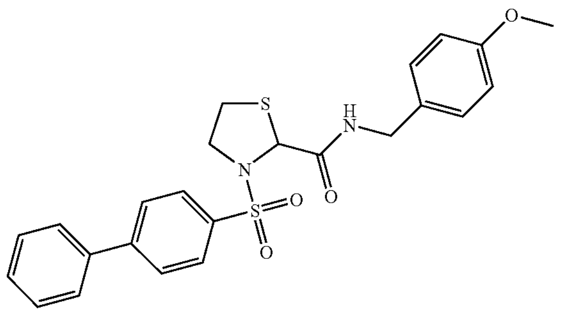 [SMILES: COc1ccc(CNC(=O)C2SCCN2S(=O)(=O)c2ccc(-c3ccccc3)cc2)cc1]

$^1$H NMR (400 MHz, $CDCl_3$); 2.6-3.1 (m, $CH_2S$, 2H), 3.7-4.1 (m, $CH_2N$, 2H), 3.8 (s, $CH_3O$, 3H), 4.6-4.7 (m, $NCH_2Ar$, 2H), 5.6 (s, CH, 1H), 7.3-8.1 (m, CH(Ar), 13H); $M^+(ESI^+)$: 469.1; $M^-(ESI^-)$: 467.4.

Example 37

3-([1,1'-biphenyl]-4-ylsulfonyl)-N-(2-thienylmethyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 2-thienylmethanamine, the title compound was obtained in 94% purity by HPLC.

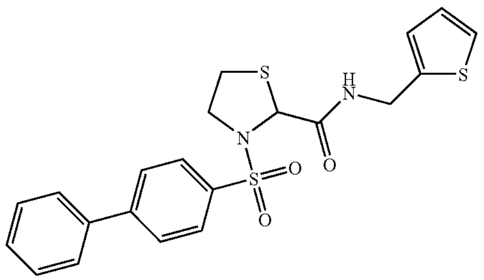

$^1$H NMR (400 MHz, $CDCl_3$); 2.55-3.1 (m, $CH_2S$, 2H), 3.65-4.05 (m, $CH_2N$, 2H), 4.6-4.85 (m, $NCH_2Ar$, 2H), 5.5 (s, CH, 2H), 6.95-8.05 (m, CH(Ar), 12H); $M^+(ESI^+)$: 445.1; $M^-(ESI^-)$: 443.1.

Example 38

3-([1,1'-biphenyl]-4-ylsulfonyl)-N-(2-furylmethyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 2-furylmethanamine, the title compound was obtained in 92.2% purity by HPLC.

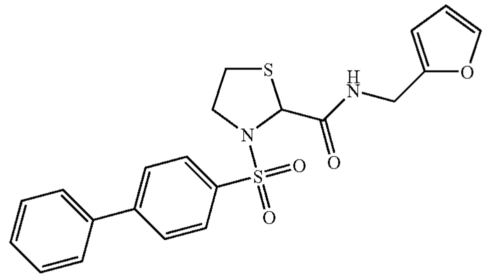 [SMILES: O=C(NCc1cccs1)C1SCCN1S(=O)(=O)c1ccc(-c2ccccc2)cc1]

$^1$H NMR (300 MHz, $CDCl_3$); 2.6-3.1 (m, $CH_2S$, 2H), 3.8-4.3 (m, $CH_2N$, 2H), 4.6-4.75 (m, $NCH_2Ar$, 2H), 5.7 (s, CH, 2H), 6.6 (m, CH(furyl), 2H), 7.45-8.3 (m, CH(Ar), 10H); $M^+(ESI^+)$: 429.5; $M^-(ESI^-)$: 427.5.

Example 39

3-([1,1'-biphenyl]-4-ylsulfonyl)-N-(4-fluorobenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and (4-fluorophenyl)methanamine, the title compound was obtained in 92% purity by HPLC.

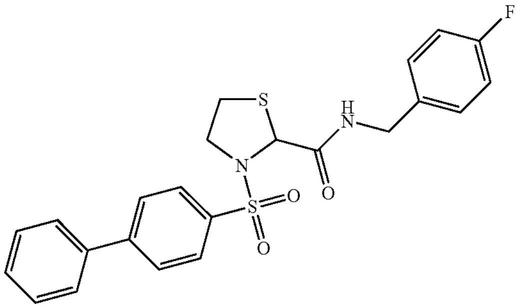 [SMILES: O=C(NCc1ccc(F)cc1)C1SCCN1S(=O)(=O)c1ccc(-c2ccccc2)cc1]

$^1$H NMR (400 MHz, $CDCl_3$); 2.65-3.1 (m, $CH_2S$, 2H), 3.7-4.1 (m, $CH_2N$, 2H), 4.6-4.7 (m, $NCH_2Ar$, 2H), 5.6 (s, CH, 1H), 6.9-7.9 (m, CH(Ar), 13H); $M^+(ESI^+)$: 457.4; $M^-(ESI^-)$: 455.2.

Example 40

N-benzhydryl-3-([1,1'-biphenyl]-4-ylsulfonyl)-1,3-thiazolidine-2-carboxamide

Following the general solid phase method as outlined Example 33, starting from 3-(tert-butoxy-carbonyl)-1,3-thiazolidine-2-carboxylic acid, Kaiser oxime resin, 1,1'-biphenyl-4-sulfonyl chloride and benzhydrylamine, the title compound was obtained in 98.5% purity by HPLC.

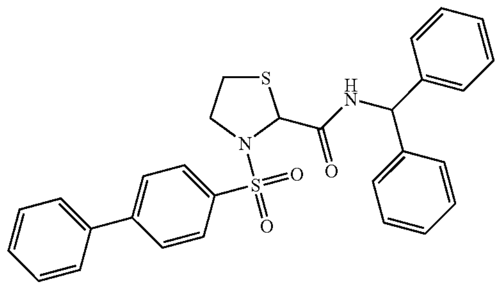 [SMILES: O=C(NC(c1ccccc1)c1ccccc1)C1SCCN1S(=O)(=O)c1ccc(-c2ccccc2)cc1]

$^1H$ NMR (400 MHz, $CDCl_3$); 2.3-2.9 (m, $CH_2S$, 2H), 3.5-3.9 (m, $CH_2N$, 2H), 5.3 (s, CH, 1H), 6.2 (s x2, NCHAr, 1H), 7.3-8.15 (m, CH(Ar), 19H); $M^+(ESI^+)$: 515.3; $M^-(ESI^-)$: 513.7.

Example 41

3-([1,1'-biphenyl]-4-ylsulfonyl-N-[1-(4-fluorophenyl)ethyl]-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 1-(4-fluorophenyl)ethanamine, the title compound was obtained in 85% purity by HPLC.

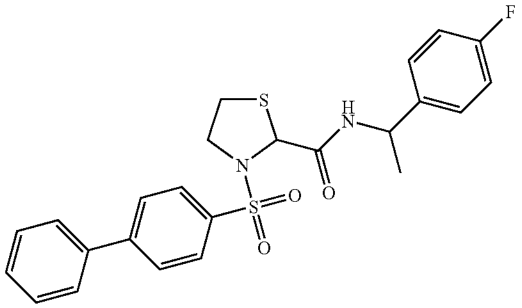 [SMILES: CC(NC(=O)C1SCCN1S(=O)(=O)c1ccc(-c2ccccc2)cc1)c1ccc(F)cc1]

$M^+(ESI^+)$: 471.2; $M^-(ESI^-)$: 469.0.

Example 42

3-([1,1'-biphenyl]-4-ylsulfonyl)-N-(2-methylbenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and (2-methylphenyl)methanamine, the title compound was obtained in 99% purity by HPLC.

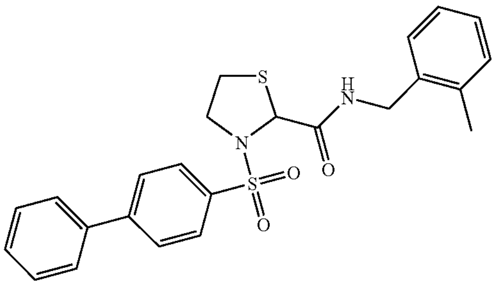 [SMILES: Cc1ccccc1CNC(=O)C1SCCN1S(=O)(=O)c1ccc(-c2ccccc2)cc1]

$M^+(ESI^+)$: 453.2; $M^-(ESI^-)$: 451.0.

Example 43

3-([1,1'-biphenyl]-4-ylsulfonyl)-N-(2,6-difluorobenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 2,6-difluorophenyl)methanamine, the title compound was obtained in 85% purity by HPLC.

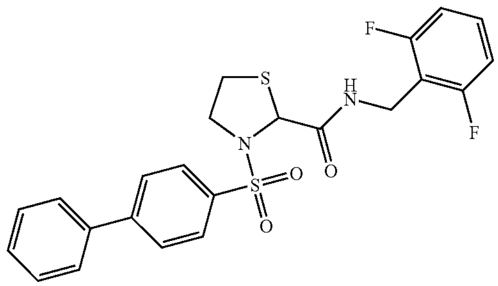 [SMILES: O=C(NCc1c(F)cccc1F)C1SCCN1S(=O)(=O)c1ccc(-c2ccccc2)cc1]

$M^+(ESI^+)$: 475.2; $M^-(ESI^-)$: 473.0.

Example 44

3-([1,1'-biphenyl]-4-ylsulfonyl)-N-(2,3-difluorobenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and 2,3-difluorophenyl)methanamine, the title compound was obtained in 93.4% purity by HPLC.

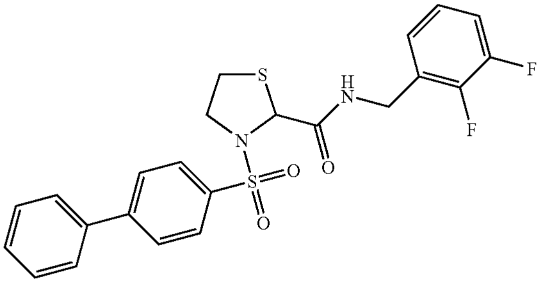 [SMILES: O=C(NCc1cccc(F)c1F)C1SCCN1S(=O)(=O)c1ccc(-c2ccccc2)cc1]

$M^+(ESI^+)$: 475.4; $M^-(ESI^-)$: 472.6.

Example 45

3-([1,1'-biphenyl]-4-ylsulfonyl)-N-(2-methoxybenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and (2-methoxyphenyl)methanamine, the title compound was obtained in 98.5% purity by HPLC.

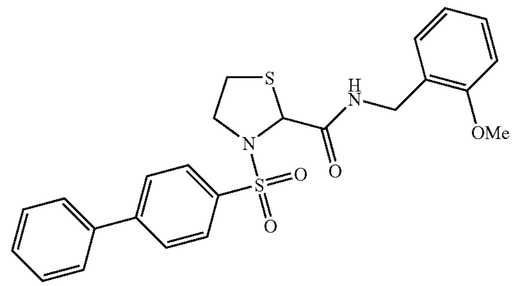 [SMILES: COc1ccccc1CNC(=O)C1SCCN1S(=O)(=O)c1ccc(-c2ccccc2)cc1]

$^1H$ NMR (400 MHz, $CDCl_3$); 2.6-3.1 (m, $CH_2S$, 2H), 3.7-4.1 (m, $CH_2N$, 2H), 3.8 (s, $CH_3O$, 3H), 4.6-4.7 (m, $NCH_2Ar$, 2H), 5.6 (s, CH, 1H), 7.3-8.1 (m, CH(Ar), 13H); $M^+(ESI^+)$: 469.2; $M^-(ESI^-)$: 467.6.

Example 46

3-([1,1'-biphenyl]-4-ylsulfonyl)-N-(2-chlorobenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and (2-chlorophenyl)methanamine, the title compound was obtained in 85% purity by HPLC.

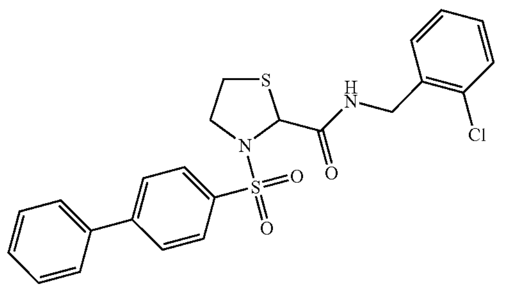 [SMILES: O=C(NCc1ccccc1Cl)C1SCCN1S(=O)(=O)c1ccc(-c2ccccc2)cc1]

$M^+(ESI^+)$: 473.3; $M^-(ESI^-)$: 470.2.

Example 47

3-([1,1'-biphenyl]-4-ylsulfonyl-N-(2-fluorobenzyl)-1,3-thiazolidine-2-carboxamide Following the general solid phase method as outlined Example 33, starting from 3-(tert-butoxycarbonyl)-1,3-thiazolidine-2-carboxylic acid, Kaiser oxime resin, 1,1'-biphenyl-4-sulfonyl chloride and (2-fluorophenyl)methanamine, the title compound was obtained in 88.6% purity by HPLC.

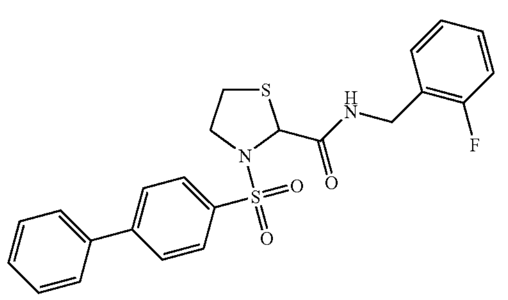 [SMILES: O=C(NCc1ccccc1F)C1SCCN1S(=O)(=O)c1ccc(-c2ccccc2)cc1]

$M^+(ESI^+)$: 457.03; $M^-(ESI^-)$: 455.4.

Example 48

General protocols for the solution-phase synthesis of 1,3-thiazolidine-2-carboxamide derivatives of general formula (XXXIII); e.g., N-[3-(acetylamino)-1-phenylpropyl]-3-([1,1'-biphenyl-4-ylsulfonyl]-1,3-thiazolidine-2-carboxamide; 3-([1,1'-biphenyl]-4-ylsulfonyl)-N-{3-[(methylsulfonyl)amino]-1-phenylpropyl}-1,3-thiazolidine-2-carboxamide.

Thiazolidine intermediates of general formula (XXXI) (Intermediate 10) or (XXXII), e.g., N-[3-amino-1-phenylpropyl]-3-([1,1'-biphenyl]-4-ylsulfonyl)-1,3-thiazolidine-2-carboxamide, were reacted with

- an acid chloride, $R^6COCl$, with an appropriate base or an acid, $R^6COOH$, with a peptide coupling agent and optionally a base
- a sulfonyl chloride, $R^6SO_2Cl$, with an appropriate base
- an isocyanate, $R^6NCO$, or triphosgene, followed by an amine, $R^6R^7NH$
- a chloroformate, $R^6OCOCl$, with an appropriate base Thus, e.g., N-[3-amino-1-phenylpropyl]-3-([1,1'-biphenyl]-4-ylsulfonyl)-1,3-thiazolidine-2-carboxamide (Intermediate 9, 50 mgs, 1.0 eq, 0.10 mmol) was dissolved in 5 ml DCM in presence of 30 µl triethylamine. Acetyl chloride (10 µl, 1.1 eq, 0.11 mol) was introduced slowly at 0° C. and the reaction mixture stirred for 30 minutes. It was then hydrolyzed by addition of aqueous sodium carbonate (10%) (5 ml), and the compound extracted with DCM. The organic phase was dried with magnesium sulfate and concentrated in vacuo to give a crude compound, which was readily purified by flash chromatography using DCM/MeOH (99/1) as eluent, to obtain the desired compound of general formula (XXXIII), e.g., N-[3-(acetylamino)-1-phenylpropyl]-3-([1,1'-biphenyl]-4-ylsulfonyl)-1,3-thiazolidine-2-carboxamide in 80% yield as a white gum in 99.5% purity by HPLC.

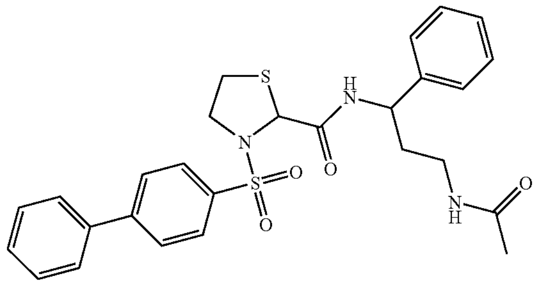

$^1H$ NMR (400 MHz, $CDCl_3$); 1.80-2.10 (m, 6H, $CH_3$, $CH_2S$, $CH_2$), 2.54 (m, 1H, $CH_2S$), 2.97-3.10 (m, 2H, $CH_2$), 3.50-3.90 (m, 3H, NH, $CH_2N$), 5.0-5.10 (m, 1H, CH), 5.24 (s, 1H, CH), 5.98-6.11 (m, 1H, NH), 7.25-7.89 (m, 14H, CH(Ar)); $M^+(ESI^+)$: 523.71; $M^-(ESI^-)$: 522.05.

Alternatively, thiazolidine intermediates of general structure (XXXI) or (XXXII), e.g., N-[3-amino-1-phenylpropyl]-3-([1,1'-biphenyl]-4-ylsulfonyl)-,3-thiazolidine-2-carboxamide (Intermediate 9, 50 mgs, 1.0 eq, 0.0 mmol), were dissolved in 10 ml DCM in presence of 30 µl of triethylamine at 0° C. Methane sulfonylchloride (10 µl, 1.1 eq, 0.11 mol) was introduced slowly and reaction mixture was stirred at 0° C. for 30 minutes. It was then hydrolyzed with aqueous sodium carbonate (10%) and the compound extracted with DCM. The organic phase was dried with magnesium sulfate, and concentrated in vacuo to give a crude compound, which was purified by flash chromatography using cyclohexane/ethyl-acetate (1/1) as eluent, to obtain the desired compounds of general structure (XXXIII), e.g., 3-([1,1'-biphenyl]-4-ylsulfonyl)-N-{3-[(methylsulfonyl)amino]-1-phenylpropyl}-1,3-thiazolidine-2-carboxamide, was obtained as a white gum in 95% yield and 99.6% purity by HPLC.

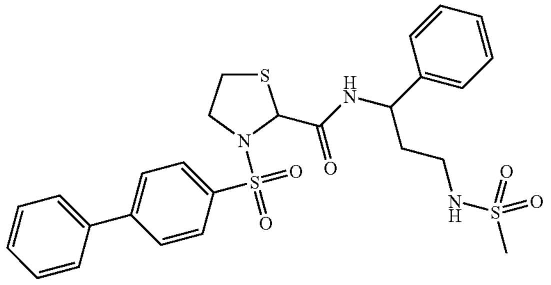 [SMILES: CS(=O)(=O)NCCC(NC(=O)C1SCCN1S(=O)(=O)c1ccc(-c2ccccc2)cc1)c1ccccc1]

$^1$H NMR (400 MHz, $CDCl_3$); 1.80-2.10 (m, 3H, $CH_2S$, $CH_2$), 2.88 (s, 3H, $CH_3$), 3.0-3.50 (m, 3H, $CH_2S$, $CH_2$), 3.70-3.85 (m, 2H, $CH_2N$), 4.45 (m, 1H, NH), 5.13-5.21 (m, 1H, CH), 5.35 (s, 1H, CH), 6.86-6.94 (m, 1H, NH), 7.35-8.10 (m, 14H, CH(Ar)); $M^+$($ESI^+$): 560.21;

$M^-$($ESI^-$): 558.47.

Example 49

General protocols for the solution-phase synthesis of 1,3-thiazolidine-2-carboxamide derivatives of general formula (XXVII): e.g. 3-([1,1'-biphenyl]-4-ylsulfonyl)-N-[3-phenoxy-1-phenylpropyl]-1,3-thiazolidine-2-carboxamide Thiazolidine intermediates of general structure (XXVI), e.g., 3-([1,1'-biphenyl]-4-ylsulfonyl)-N-(3-hydroxy-1-phenylpropyl)-1,3-thiazolidine-2-carboxamide (1.0 g, 1.0 eq, 2.07 mmol) was dissolved in 20 ml dry THF under nitrogen. Phenol (252 mg, 1.5 eq, 2.69 mmol), diethylazodicarboxylate (470 mg, 1.5 eq, 2.69 mmol) and triphenyl phosphine polymer bound (1.0 g, 1.5 eq, 2.70 mmol) were then added and the reaction mixture was shaken for 12 hours at RT. Triphenyl phosphine resin was filtered off and the THF solution evaporated in vacuo. The residue was taken up in DCM and washed twice with saturated sodium carbonate solution and then water. The organic layer was dried with magnesium sulfate and concentrated in vacuo to give a crude product which was purified on silica gel using cyclohexane/ethyl acetate(8/2) as eluent, affording the desired products of general structure (XXVII), e.g., 3-([1,1'-biphenyl]-4-ylsulfonyl)-N-[3-phenoxy-1-phenylpropyl]-1,3-thiazolidine-2-carboxamide as a white oil in 40% yield and 95.5% purity by HPLC.

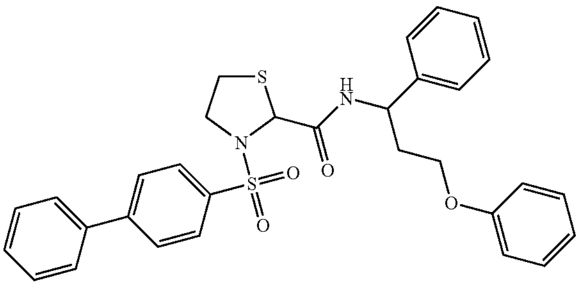 [SMILES: O=C(NC(CCOc1ccccc1)c1ccccc1)C1SCCN1S(=O)(=O)c1ccc(-c2ccccc2)cc1]

$^1$H NMR (400 MHz, $CDCl_3$); 2.22-2.40 (m, 2H, $CH_2$), 2.41-2.50 (m, 1H, $CH_2S$), 2.78-2.81 (m, 1H, $CH_2S$), 3.56-3.93 (m, 4H, $CH_2N$, $CH_2O$), 5.21 (m, 1H, CH), 5.31 (s, 1H, CH), 6.79-6.92 (m, 4H, CH(Ar) and NH), 7.20-7.85 (m, 16H, CH(Ar)); $M^+$($ESI^+$): 559.39; $M^-$($ESI^-$): 557.61.

Example 50

3-(biphenyl-4-ylsulfonyl)-N-[(2-chloropyridin-4-yl)(phenyl)methyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 1-(2-chloropyridin-4-yl)-1-phenylmethanamine (Intermediate 2), the title compound was obtained in 98% purity by HPLC.

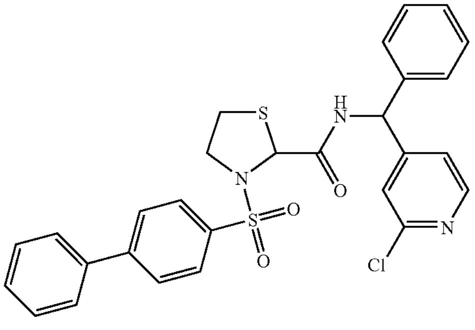 [SMILES: O=C(NC(c1ccccc1)c1ccnc(Cl)c1)C1SCCN1S(=O)(=O)c1ccc(-c2ccccc2)cc1]

$^1$H NMR (300 MHz, $CDCl_3$); 2.58 (m, 1H), 2.93 (m, 1H), 3.77 (m, 2H), 5.28 (s, 0.5H), 5.31 (s, 0.5H), 6.07 (m, 1H), 7.13 (m, 4H), 7.37 (m, 7H), 7.55 (m, 2H), 7.71 (m, 2H), 7.87 (m, 2H), 8.30 (m, 1H). $M^+$($ESI^+$): 550; $M^-$($ESI^-$): 548.

Example 51

3-(biphenyl-4-ylsulfonyl)-N-[(6-chloropyridin-3-yl)(phenyl)methyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and [(6-chloropyridin-3-yl)(phenyl)methyl]amine (Intermediate 2), the title compound was obtained in 99% purity by HPLC.

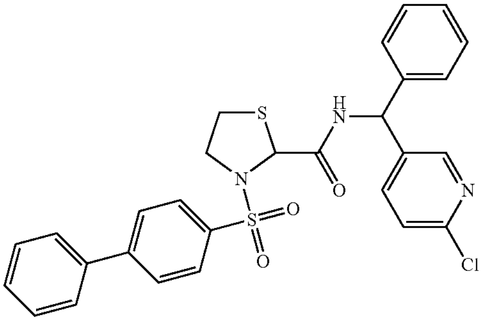 [SMILES: O=C(NC(c1ccccc1)c1ccc(Cl)nc1)C1SCCN1S(=O)(=O)c1ccc(-c2ccccc2)cc1]

$^1$H NMR (300 MHz, $CDCl_3$); 2.60 (m, 1H), 2.94 (m, 1H), 3.72 (m, 1H), 3.86 (m, 1H), 5.31 (s, 0.5H), 5.36 (s, 0.5H), 6.21 (m, 1H), 7.36 (m, 1H), 7.60 (m, 2H), 7.76 (m, 2H), 7.90 (m, 2H), 8.34 (m, 1H). $M^+$($ESI^+$): 550; $M^-$($ESI^-$): 548.

Example 52

3-(biphenyl-4-ylsulfonyl)-N-[(6-hydroxypyridin-3-yl)(phenyl)methyl]-1,3-thiazolidine-2-carboxamide Following the general strategies and protocols outlined in Example 1, starting from 3-([1,1'-biphenyl]-4-ylsulfonyl)-1, 3-thiazolidine-2-carboxylic acid (Intermediate 8) and 5-[amino(phenyl)methyl]pyridin-2-ol (Intermediate 2), the title compound was obtained in 99% purity by HPLC.

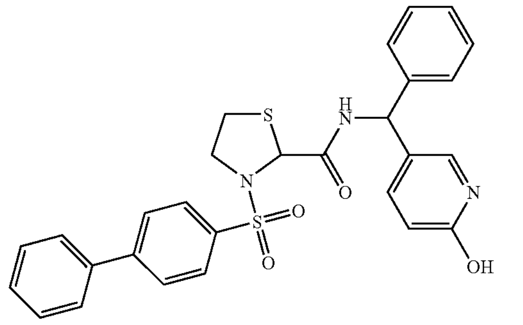 [SMILES: O=C(NC(c1ccccc1)c1ccc(O)nc1)C1SCCN1S(=O)(=O)c1ccc(-c2ccccc2)cc1]

$^1$H NMR (300 MHz, DMSO-d6); 2.58 (m, 1H), 2.97 (m, 1H), 3.69 (m, 2H), 5.41 (m, 1H), 5.65 (m, 1H), 6.18 (m, 1H), 7.20 (m, 10H), 7.60 (m, 2H), 7.77 (m, 4H), 8.73 (m, 1H), 11.37 (br s, 1H). $M^+(ESI^+)$: 532; $M^-(ESI^-)$: 530.

Example 53

3-(biphenyl-4-ylsulfonyl)-N-[[6-(dimethylamino) pyridin-3-yl](phenyl)methyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and 5-[amino(phenyl)methyl]-N,N-dimethylpyridin-2-amine (Intermediate 2), the title compound was obtained in 98% purity by HPLC.

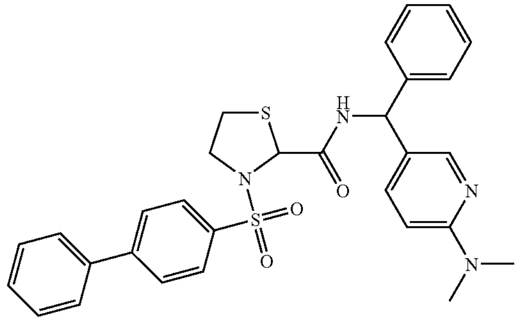 [SMILES: CN(C)c1ccc(C(NC(=O)C2SCCN2S(=O)(=O)c2ccc(-c3ccccc3)cc2)c2ccccc2)cn1]

$^1$H NMR (300 MHz, $CDCl_3$); 2.61 (m, 1H), 2.99 (m, 1H), 3.15 (s, 6H), 3.72 (m, 1H), 3.90 (s, 1H), 5.36 (s, 0.5H), 5.39 (s, 0.5H), 6.10 (m, 1H), 6.56 (m, 1H), 7.13 (m, 1H), 7.28 (m, 6H), 7.46 (m, 3H), 7.60 (m, 2H), 7.73 (m, 2H), 7.91 (m, 2H), 8.02 (m, 0.5H), 8.09 (m, 0.5H). $M^+(ESI^+)$: 559; $M^-(ESI^-)$: 558.

Example 54

3-(biphenyl-4-ylsulfonyl)-N—[(R)-{5-[2-(dimethylamino)ethoxy]pyridin-2-yl}(phenyl)methyl]-1,3-thiazolidine-2-carboxamide Following the general strategies and protocols outlined in Example 1, starting from 3-([1,1'-biphenyl]-4-ylsulfonyl)-1,3-thiazolidine-2-carboxylic acid (Intermediate 8) and [2-({6-[(R)-amino(phenyl)methyl]pyridin-3-yl}oxy)ethyl]dimethylamine (Intermediate 2), the title compound was obtained in 99% purity by HPLC.

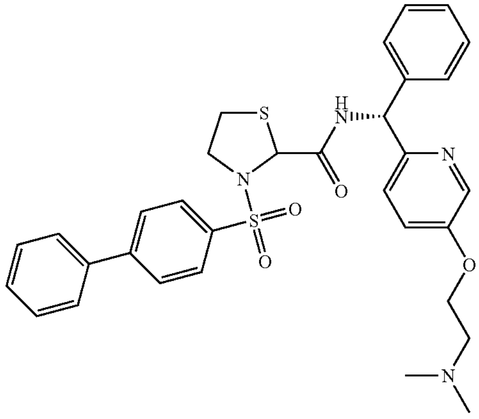 [SMILES: CN(C)CCOc1ccc([C@H](NC(=O)C2SCCN2S(=O)(=O)c2ccc(-c3ccccc3)cc2)c2ccccc2)nc1]

$^1$H NMR (300 MHz, $CDCl_3$); 2.63 (m, 7H), 2.99 (m, 3H), 3.71 (m, 1H), 4.02 (m, 1H), 4.26 (br s, 2H), 5.48 (s, 0.5H), 5.49 (s, 0.5H), 6.02 (s, 0.5H), 6.05 (s, 0.5H), 7.25 (m, 6H), 7.44 (m, 4H), 7.58 (m, 2H), 7.70 (m, 2H), 7.93 (m, 2H), 8.33 (m, 2H). $M^+(ESI^+)$: 603; $M^-(ESI^-)$: 601.

Example 55

4-[(S)-[({(2S)-3-[(2'-fluorobiphenyl-4-yl)sulfonyl]-1,3-thiazolidin-2-yl}carbonyl)amino](phenyl)methyl]-1-methylpiperidinium methanesulfonate Following the strategies and protocols outlined in Example 1, the title compound was obtained in 99% purity by HPLC.

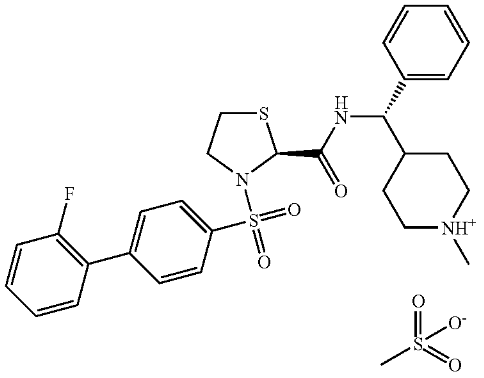

$^1$H NMR (300 MHz, DMSO-d6); 1.40 (m, 2H), 1.92 (m, 2H), 2.29 (s, 3H), 2.70 (m, 3H), 3.06 (m, 1H), 3.31 (m, 4H), 3.82 (m, 2H), 4.58 (m, 1H), 5.50 (s, 1H), 7.34 (m, 7H), 7.56 (m, 2H), 7.90 (m, 4H), 8.57 (m, 1H), 9.10 (m, 1H). $M^+(ESI^+)$: 554; $M^-(ESI^-)$: 552.

Example 56 benzeneacetic acid, alpha,alpha-dimethyl-4-[[2-[[[(R)-phenyl-2-pyridinylmethyl]amino]carbonyl]-3-thiazolidinyl]sulfonyl]-, methyl ester Following the general strategies and protocols outlined in Example 1, starting from 2-thiazolidinecarboxylic acid, 3-[[4-(2-methoxy-1,1-dimethyl-2-oxoethyl)phenyl]sulfonyl]-(Intermediate 8) and (R)-phenyl(2-pyridinyl)methanamine (intermediate 1), the title compound was obtained in 91% purity by HPLC.

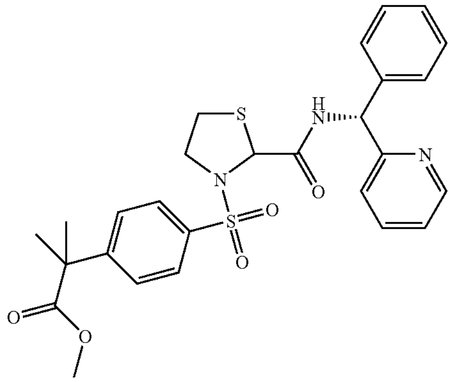 [SMILES: COC(=O)C(C)(C)c1ccc(S(=O)(=O)N2CCSC2C(=O)N[C@H](c2ccccc2)c2ccccn2)cc1]

$^1$H NMR (300 MHz, $CDCl_3$); δ 8.63 (s, 1H); 7.82-7.91 (m, 3H); 7.33-7.51 (m, 9H); 6.2 (s, 1H); 5.65 (s, 1H); 3.88 (m, 2H); 3.66 (s, 3H); 3.10 (m, 1H); 2.65 (m, 11H) 1.6 (s, 6H). $M^+(ESI^+)$: 540.1; $M^-(ESI^-)$: 538.0.

Example 57

Preparation of product Ia, e.g. ({[3-(biphenyl-4-yl-sulfonyl)-1,3-thiazolidin-2-yl]carbonyl}amino)(phenyl)acetic acid

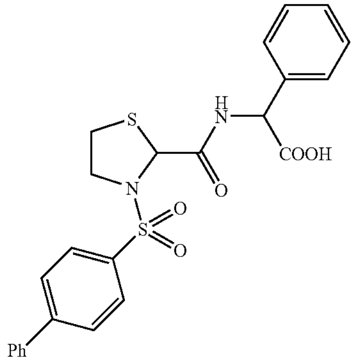 [SMILES: O=C(O)C(NC(=O)C1SCCN1S(=O)(=O)c1ccc(-c2ccccc2)cc1)c1ccccc1]

Intermediate VIII (Scheme 3), e.g., 3-(biphenyl-4-ylsulfonyl)-1,3-thiazolidine-2-carboxylic acid (1.747 g, 5 mmol) was dissolved in DCM (20 mL). The resulting solution was cooled down to −10° C. and oxalyl chloride (0.645 mL, 7.5 mmol) was added slowly. DMF (0.1 mL) was added carefully. The reaction mixture was allowed to warm to RT over 1 h and stirred an additional hour at RT. As the reaction was complete, the solvents were evaporated. Toluene was added and evaporated to remove residual oxalyl chloride. This process was repeated twice, affording intermediate XXX, e.g., 3-(biphenyl-4-ylsulfonyl)-1,3-thiazolidine-2-carbonyl chloride as a yellow solid (1.839 g, quantitative yield). α-Aminophenylacetic acid (831 mg, 5.5 mmol) was dissolved in water (20 mL). TEA (2.77 mL, 20 mmol) was added carefully. THF (25 mL) was added to reaction mixture. The reaction mixture was cooled to 0° C. Acid chloride previously prepared XXX, e.g. 3-(biphenyl-4-ylsulfonyl)-1,3-thiazolidine-2-carbonyl chloride dissolved in THF (25 mL) was added dropwise. The reaction mixture was stirred 15 min at 0° C. and overnight at RT. Solvents were concentrated and the resulting aqueous fraction was acidified with HCl 5N and extracted with 3 portions of EtOAc. Combined organic phases were dried over $MgSO_4$, filtrated and evaporated. The crude product was recrystallized in acetone/Et2O mixture, affording carboxylic acid Ia, e.g., ({[3-(biphenyl-4-ylsulfonyl)-1,3-thiazolidin-2-yl]carbonyl}amino)(phenyl)acetic acid in 97% purity by HPLC (943 mg, 39% yield).

$^1$HNMR (300 MHz, DMSO-d6); 2.68 (m, 1H), 3.08 (m, 1H), 3.84 (m, 2H), 5.30 (m, 1H), 5.76 (s, 0.5H), 5.82 (s, 0.5H), 7.44 (m, 8H), 7.78 (m, 2H), 7.93 (m, 4H), 8.91 (m, 1H), 13.10 (br s, 1H). $M^+(ESI^+)$: 483; $M^-(ESI^-)$: 481.

Example 58

Preparation of product Ib, e.g. N-(2-amino-2-oxo-1-phenylethyl)-3-(biphenyl-4-ylsulfonyl)-1,3-thiazolidine-2-carboxamide

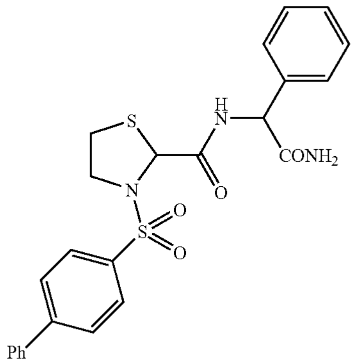 [SMILES: NC(=O)C(NC(=O)C1SCCN1S(=O)(=O)c1ccc(-c2ccccc2)cc1)c1ccccc1]

Compound Ia, e.g., ({[3-(biphenyl-4-ylsulfonyl)-1,3-thiazolidin-2-yl]carbonyl}amino)-(phenyl)acetic acid (500 mg, 1.04 mmol) was dissolved in THF (10 mL). Ammonia in dioxane (0.5N, 3.11 mL, 1.55 mmol) was added followed by HOBt (210 mg, 1.55 mmol) and DMAP (6 mg, 0.05 mmol). EDC.HCl (298 mg, 1.55 mmol) was finally added. The mixture was stirred for 5 hours at RT. As the reaction was complete, it was diluted with EtOAc, washed with 5% citric acid, $NH_4Cl$ sat, $NaHCO_3$ sat, brine and dried over $MgSO_4$. After filtration and evaporation of the solvents, the resulting crude product was purified by flash chromatography (Cyclohexane/EtOAc, gradient from 1:1 to 0:1). Compound Ib, e.g. N-(2-amino-2-oxo-1-phenylethyl)-3-(biphenyl-4-ylsulfonyl)-1,3-thiazolidine-2-carboxamide, was isolated in 90% purity by HPLC (349 mg, 80% yield).

$^1$H NMR (300 MHz, DMSO-d6); 2.64 (m, 1H), 3.04 (m, 1H), 3.78 (m, 2H), 5.34 (m, 1H), 5.84 (m, 1H), 7.29 (m, 4H), 7.47 (m, 4H), 7.76 (m, 2H), 7.90 (m, 4H), 8.77 (m, 1H). $M^+(ESI^+)$: 482; $M^-(ESI^-)$: 480.

Example 59

Preparation of product Ic, e.g. 3-(biphenyl-4-ylsulfonyl)-N-[cyano(phenyl)-methyl]-1,3-thiazolidine-2-carboxamide

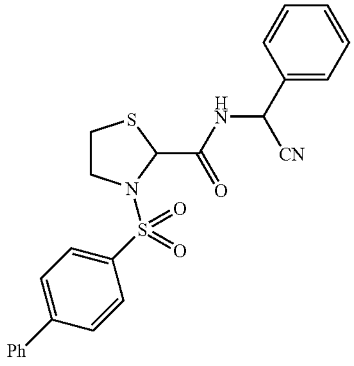 [SMILES: N#CC(NC(=O)C1SCCN1S(=O)(=O)c1ccc(-c2ccccc2)cc1)c1ccccc1]

To a stirred solution of compound 1b, e.g., N-(2-amino-2-oxo-1-phenylethyl)-3-(biphenyl-4-ylsulfonyl)-1,3-thiazolidine-2-carboxamide (385 mg, 0.8 mmol) in DMF (1 mL) at RT was added cyanuric chloride (74 mg, 0.4 mmol) in one portion. After one night, the reaction was done. Water (3 mL) was added and a precipitate was formed. The aqueous phase was extracted with two portions of EtOAc (5 mL). Combined organic phases were washed with 5% aqueous sodium bicarbonate, with water, dried over $MgSO_4$ and concentrated under reduced pressure. A light yellow solid was isolated and was purified by flash chromatography (Cyclohexane/EtOAc gradient form 8:2 to 1:1), affording product Ic, e.g., 3-(biphenyl-4-ylsulfonyl)-N-[cyano(phenyl)methyl]-1,3-thiazolidine-2-carboxamide (257 mg, 69% yield) in 100% purity by HPLC.

$^1$H NMR (300 MHz, $CDCl_3$); 2.61 (m, 1H), 2.99 (m, 1H), 3.72 (m, 2H), 5.35 (s, 0.5H), 5.41 (s, 0.5H), 6.06 (m, 0.5H), 6.17 (m, 0.5H), 7.17 (m, 1H), 7.47 (m, 8H), 7.61 (m, 2H), 7.77 (m, 2H), 7.91 (m, 2H). $M^+$($ESI^+$): 464; $M^-$($ESI^-$): 462.

Example 60

Preparation of product I, e.g. 3-(biphenyl-4-ylsulfonyl)-N-[[5-(2-hydroxyethyl)-1,2,4-oxadiazol-3-yl](phenyl)methyl]-1,3-thiazolidine-2-carboxamide

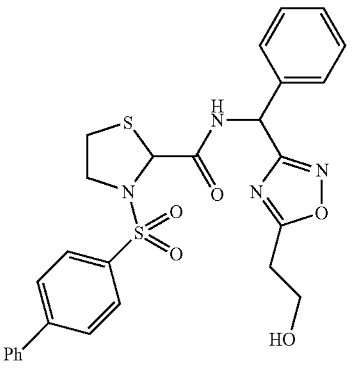 [SMILES: O=C(NC(c1ccccc1)c1noc(CCO)n1)C1SCCN1S(=O)(=O)c1ccc(-c2ccccc2)cc1]

Triethylamine (92 μl, 0.66 mmol) was slowly added to a suspension of product Ic, e.g., 3-(biphenyl-4-ylsulfonyl)-N-[cyano(phenyl)methyl]-1,3-thiazolidine-2-carboxamide, and hydroxylamine.hydrochloride (46 mg, 0.66 mmol) in ethanol (5 mL), under stirring. The reaction mixture was heated under reflux for 16 h, and then cooled to RT. The solvents were removed and the resulting solid was suspended in water and extracted with three portions of EtOAc. Combined organic phases were dried over $MgSO_4$, filtrated and evaporated, affording intermediate Id, e.g., N-[(1R,2Z)-2-amino-2-(hydroxyimino)-1-phenylethyl]-3-(biphenyl-4-ylsulfonyl)-1,3-thiazolidine-2-carboxamide (272 mg, quantitative yield) which was directly used in the next step.

$^1$H NMR (300 MHz, $CDCl_3$); 2.35 (br s, 2H), 2.55 (m, 2H), 3.00 (m, 1H), 3.60-3.93 (m, 2H), 5.30 (s, 0.5H), 5.40 (s, 0.5H),), 5.64 (m, 1H) 7.05-8.17 (m, 14H, H arom.). $M^+$($ESI^+$): 497. $M^-$($ESI^-$): 495.

Carboxylic acid, e.g., 3-tert-butoxypropionic acid (35 mg, 0.24 mmol), was dissolved in THF (2 mL). The resulting solution was cooled down to −15° C. NMM (84 μL, 0.76 mmol), followed by isobutyl chloroformate (33 μL, 0.25 mmol), were added. The mixture was stirred at −15° C. for 30 min. Intermediate Id, e.g. N-[(1R,2Z)-2-amino-2-(hydroxyimino)-1-phenylethyl]-3-(biphenyl-4-ylsulfonyl)-1,3-thiazolidine-2-carboxamide (108 mg, 0.22 mmol) in THF (2 mL) was added dropwise. The mixture was stirred overnight, letting the temperature increasing up to RT. Solvents were evaporated. The resulting oil was dissolved in AcOEt, and washed with sat $NH_4Cl$ and sat $NaHCO_3$. Aqueous phases were extracted with two portions of AcOEt. Combined organic phases were dried over $MgSO_4$, filtrated and evaporated, affording intermediate Id', e.g. 3-(biphenyl-4-ylsulfonyl)-N-[(2E)-2-[(3-tert-butoxypropanoyl)amino]-2-(hydroxyimino)-1-phenylethyl]-1,3-thiazolidine-2-carboxamide (118 mg, 86% yield), which was directly used in the next step.

$M^+$($ESI^+$): 625. $M^-$($ESI^-$): 623.

Intermediate Id', e.g., 3-(biphenyl-4-ylsulfonyl)-N-[(2E)-2-[(3-tert-butoxypropanoyl)amino]-2-(hydroxyimino)-1-phenylethyl]-1,3-thiazolidine-2-carboxamide (118 mg, 0.19 mmol), was suspended in dry toluene. Pyridine (46 μL, 0.56 mmol) was added. The mixture was stirred under reflux. After 7 hours the reaction was complete and the solvents were evaporated.

The crude residue was dissolved in EtOAc, and washed with two portions of brine. Combined aqueous phases were extracted with two portions of EtOAc. Combined organic phases were dried over $MgSO_4$, filtrated and evaporated. The crude product was dissolved in DCM (2.5 mL) and TFA (0.5 mL) was added at 0° C. The mixture was stirred 15 min at 0° C. then overnight at RT. Solvents were evaporated. The crude oil was stirred 5 hours in MeOH, in order to hydrolyze the trifluoroacetic ester formed. After evaporation of the solvents, the desired product was purified by flash chromatography (Cylclohexane/EtoAc, gradient from 8:2 to 0:1), affording product 1, e.g. 3-(biphenyl-4-ylsulfonyl)-N-[[5-(2-hydroxyethyl)-1,2,4-oxadiazol-3-yl](phenyl)methyl]-1,3-thiazolidine-2-carboxamide (25 mg, 24% yield over three steps) in 100% purity by HPLC.

$^1$H NMR (300 MHz, $CDCl_3$); 1.85 (br s, 1H), 2.62 (m, 1H), 3.07 (m, 3H), 3.75 (m, 1H), 4.00 (m, 3H), 5.38 (s, 0.5H), 5.44 (s, 0.5H), 6.37 (m, 1H), 7.40 (m, 8H), 7.66 (m, 5H), 7.91 (m, 2H). $M^+$($ESI^+$): 551; $M^-$($ESI^-$): 549.

Example 61

Preparation of product XXX. e.g. 2-thiazolidinecarboxamide, 3-[[4-(2-fluoro-1,1-dimethylethyl)phenyl]sulfonyl]-N—[(R)-phenyl-2-pyridinylmethyl]

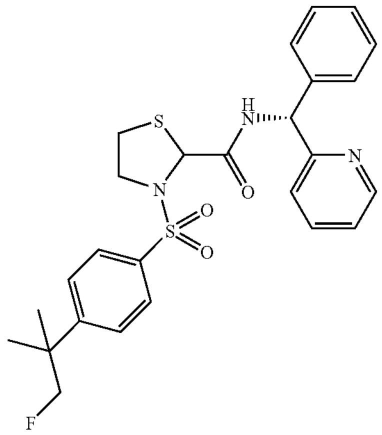 [SMILES: CC(C)(CF)c1ccc(S(=O)(=O)N2CCSC2C(=O)N[C@H](c2ccccc2)c2ccccn2)cc1]

The compound benzeneacetic acid, alpha,alpha-dimethyl-4-[[2-[[[(R)-phenyl-2-pyridinyl-methyl]amino]carbonyl]-3- thiazolidinyl]sulfonyl]-, methyl ester (Example X) (54 mg, 0.1 mmol) was dissolved in 3 mL of anhydrous THF. The solution was cooled down to zero degree and LiBH4 was added (3 mg, 0.15 mmol, 1.5 eq). The reaction mixture was agitated for 2 h. The reaction mixture was quenched by addition of $H_2O$. The organic solvent was evaporated under reduced pressure, and the residue redissolved in EtOAc. The organic layer was washed with $NaHCO_3$ sat., NaCl sat, dried over $MgSO_4$, and evaporated in vacuo to give 2-thiazolidinecarboxamide, 3-[[4-(2-hydroxy-1,1-dimethylethyl)phenyl]sulfonyl]-N—[(R)-phenyl-2-pyridinylmethyl]—as a colorless oil (44 mg, yield: 86%).

$^1$H NMR (300 MHz, $CDCl_3$); δ 8.07 (m, 2H); 7.82-7.97 (m, 3H); 7.28-7.58 (m, 9H); 6.26 (s, 1H); 3.86 (m, 2H); 3.36 (d, 2H); 3.635 (m, 1H); 2.71 (m, 1H); 1.36 (s, 1H) $M^+(ESI^+)$: 512.4. $M^-(ESI^-)$: 510.3.

The compound 2-thiazolidinecarboxamide, 3-[[4-(2-hydroxy-1,1-dimethylethyl)phenyl]sulfonyl]-N—[(R)-phenyl-2-pyridinylmethyl]-(43 mg, 0.08 mmol) was dissolved in 2 mL anhydrous DCM. The solution was cooled down to −78° C., and DAST (0.02 mL, 0.17 mmol, 2 eq) was added. The reaction mixture was stirred for 24 h at −78° C. and warmed to room temperature. The reaction was quenched by addition of $NaHCO_3$ sat. and agitated for 1 h. The product was extracted with DCM (50 mL). The organic layer was dried over $MgSO_4$ and evaporated. The residue was purified by with EtOAc/cHex, 40:60) to give compound 2-thiazolidinecarboxamide, 3-[[4-(2-fluoro-1,1-dimethylethyl)phenyl]sulfonyl]-N—[(R)-phenyl-2-pyridinylmethyl]—as an orange oil (14.8 mg, yield: 36%, 98.1 HPLC purity).

$^1$H-RMN($CH_2Cl_2$) δ 8.58 (m, 2H); 7.83 (t, Jt=8.29, 2H); 7.65 (m, 1H); 7.19-7.40 (m, 9H); 6.10 (s, 1H); 5.46 (s, 1H); 3.95-4.06 (m, 1H); 3.65-3.78 (m, 1H); 2.92-2.99 (m, 3H); 2.55-2.64 (m, 1H); 1.25-1.37 (m, 6H). $^{19}$F-RMN($CH_2Cl_2$) δ-138.6. $M^+(ESI^+)$: 514.2; $M^-(ESI^-)$: 512.2

Example 62

(2S)-3-(1,1'-biphenyl-4-ylsulfonyl)-N—[(R)-phenyl(pyridin-2-yl)methyl]-1,3-thiazolidine-2-carboxamide Following the general strategies and protocols outlined in Example 1, starting from tert-butyl (2S)-2-({[(R)-phenyl(pyridin-2-yl)methyl]amino}-carbonyl)-1,3-thiazolidine-3-carboxylate (Intermediate 6) and [1,1'-biphenyl]-4-sulfonyl chloride, the title compound was obtained in 99% purity by HPLC.

$M^+(ESI^+)$: 516; $M^-(ESI^-)$: 514.

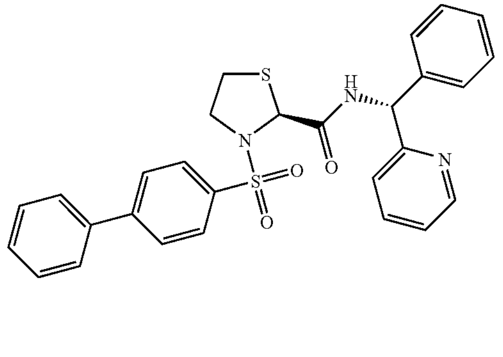 [SMILES: O=C(N[C@H](c1ccccc1)c1ccccn1)[C@@H]1SCCN1S(=O)(=O)c1ccc(-c2ccccc2)cc1]

Example 63

(2S)-3-[(2'-fluorobiphenyl-4-yl)sulfonyl]-N—[(R)-phenyl(pyridin-2-yl)methyl]-1,3-thiazolidine-2-carboxamide Following the general strategies and protocols outlined in Example 1, starting from tert-butyl (2S)-2-({[(R)-phenyl(pyridin-2-yl)methyl]amino}-carbonyl)-1,3-thiazolidine-3-carboxylate (Intermediate 6) and 2'-fluorobiphenyl-4-yl)sulfonyl chloride, the title compound was obtained in 99% purity by HPLC.

$M^+(ESI^+)$: 534.6; $M^-(ESI^-)$: 532.9.

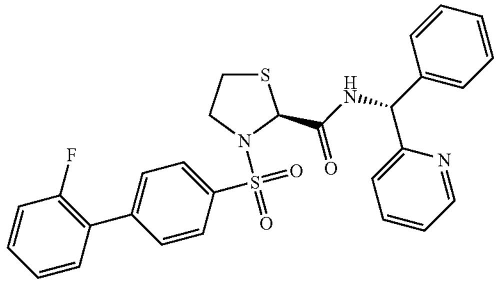 [SMILES: O=C(N[C@H](c1ccccc1)c1ccccn1)[C@@H]1SCCN1S(=O)(=O)c1ccc(-c2ccccc2F)cc1]

Example 64

(2S)-3-(biphenyl-4-ylsulfonyl)-N-[(1S)-1-(4-fluorophenyl)-3-hydroxypropyl]-1,3-thiazolidine-2-carboxamide Following the general strategies and protocols outlined in Example 1, starting from tert-butyl (2S)-2-({[(1S)-3-hydroxy-1-phenylpropyl]amino}carbonyl)-1,3-thiazolidine-3-carboxylate (Intermediate 6) and [1,1'-biphenyl]-4-sulfonyl chloride, the title compound was obtained in 98% purity by HPLC.

$M^+(ESI^+)$: 501.6; $M^-(ESI^-)$: 499.2.

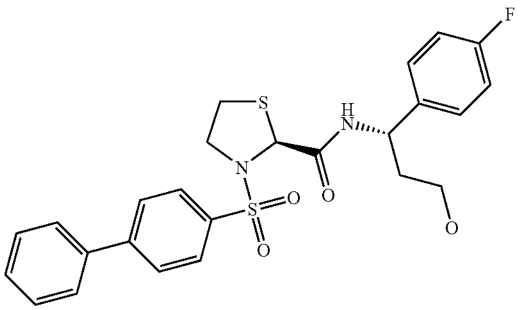 [SMILES: O=C(N[C@@H](CCO)c1ccc(F)cc1)[C@@H]1SCCN1S(=O)(=O)c1ccc(-c2ccccc2)cc1]

Example 65

3-(1,1'-biphenyl-4-ylsulfonyl)-N-[1-(2,6-difluorophenyl)-3-hydroxypropyl]-1,3-thiazolidine-2-carboxamide Following the general strategies and protocols outlined in Example 1, starting tert-butyl (2S)-2-({[(1S)-1-(2,6-difluorophenyl)-3-hydroxypropyl]amino}carbonyl)-1,3-thiazolidine-3-carboxylate (intermediate 6) and [1,1'-biphenyl]-4-sulfonyl chloride, the title compound was obtained in 99% purity by HPLC.

$M^+(ESI^+)$: 519.9; $M^-(ESI^-)$: 517.8

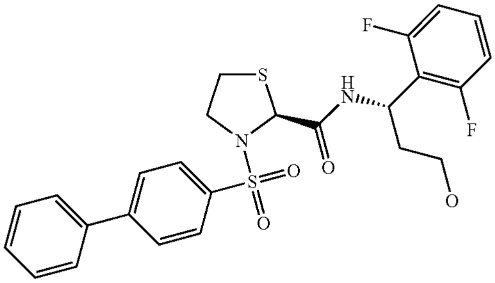 [SMILES: O=C(N[C@@H](CCO)c1c(F)cccc1F)[C@@H]1SCCN1S(=O)(=O)c1ccc(-c2ccccc2)cc1]

Example 66

(2S)—N-[(1S)-1-(4-fluorophenyl)-3-hydroxypropyl]-3-[(2'-fluorobiphenyl-4-yl)sulfonyl]-1,3-thiazolidine-2-carboxamide Following the general strategies and protocols outlined in Example 1, starting tert-butyl (2S)-2-({[(1S)-1-(2,6-difluorophenyl)-3-hydroxypropyl]amino}carbonyl)-1,3-thiazolidine-3-carboxylate (Intermediate 6) and 2'-fluorobiphenyl-4-yl)sulfonyl chloride, the title compound was obtained in 99% purity by HPLC.

$M^+(ESI^+)$: 537.9; $M^-(ESI^-)$: 535.9.

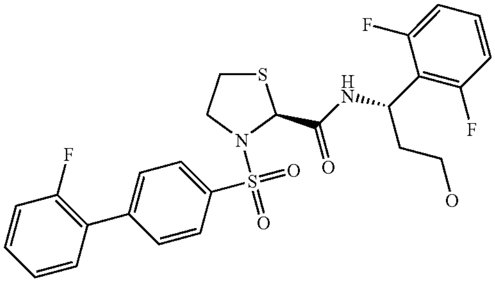 [SMILES: O=C(N[C@@H](CCO)c1c(F)cccc1F)[C@@H]1SCCN1S(=O)(=O)c1ccc(-c2ccccc2F)cc1]

Example 67

(2S)-3-[(2'-fluoro-1,1'-biphenyl-4-yl)sulfonyl]-N-[(1S)-3-hydroxy-1-phenylpropyl]-1,3-thiazolidine-2-carboxamide Following the general strategies and protocols outlined in Example 1, starting tert-butyl (2S)-2-({[(1S)-3-hydroxy-1-phenylpropyl]amino}carbonyl)-1,3-thiazolidine-3-carboxylate (Intermediate 6) and [1,1'-biphenyl]-4-sulfonyl chloride, the title compound was obtained in 98% purity by HPLC.

$M^+(ESI^+)$: 501.9; $M^-(ESI^-)$: 499.5.

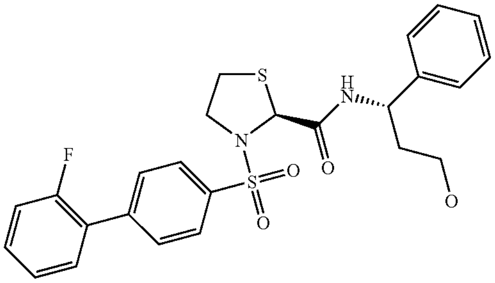 [SMILES: O=C(N[C@@H](CCO)c1ccccc1)[C@@H]1SCCN1S(=O)(=O)c1ccc(-c2ccccc2F)cc1]

Example 68

General protocols for the solution-phase synthesis of 1,3-thiazolidine-2-carboxamide derivatives of general formula (I): e.g., (3S)-3-({[(2S)-3-biphenyl-4-ylsulfonyl)-1,3-thiazolidin-2-yl]carbonyl}amino)-3-(2,6-difluorophenyl)propyl L-valinate, (3S)-3-(2,6-difluorophenyl)-3-[({(2S)-3-[(2'-fluorobiphenyl-4-ylsulfonyl]-1,3-thiazolidin-2-yl}carbonyl)amino] propyl L-valinate, (3S)-3-[({(2S)-3-(biphenyl-4-ylsulfonyl)-1,3-thiazolidin-2-yl]carbonyl}amino)-3-phenylpropyl L-valinate, (3S)-3-[({(2S)-3-[(2'-fluorobiphenyl-4-yl)sulfonyl]-1,3-thiazolidin-2-yl}carbonyl)amino]-3-phenylpropyl L-valinate.

(2S)—N-[(1S)-1-(4-fluorophenyl)-3-hydroxypropyl]-3-[(2'-fluorobiphenyl-4-yl)sulfonyl]-1,3-thiazolidine-2-carboxamide (2.48 g, 4.62 mmol) was dissolved in 40 mL of DMF:DCM (1:1) and DMAP (846 mg, 6.93 mmol) was added. To this solution was added a 5-min pre-incubated solution of HOBt (937 mg, 6.93 mmol), EDC (1.35 g, 6.93 mmol) and Boc-L-valine (1.5 g, 6.93 mmol). The reaction mixture was agitated for 16 h at room temperature. The reaction mixture was diluted with DCM (200 mL) and washed with citric acid 5%, $NH_4Cl$ sat, $NaHCO_3$ sat and brine. The organic layer was dried over $MgSO_4$ and evaporated. The residue was purified by FC 10:90 to 50:50 (EtOAc:cyclohexane) to give the desired product (3S)-3-(2,6-difluorophenyl)-3-[({(2S)-3-[(2'-fluorobiphenyl-4-yl)sulfonyl]-1,3-thiazolidin-2-yl}carbonyl)amino]propyl N-(tert-butoxycarbonyl)-L-valinate a white solid (3.04 g, 89.4%).

Compound (3S)-3-(2,6-difluorophenyl)-3-[({(2S)-3-[(2'-fluorobiphenyl-4-yl)sulfonyl]-1,3-thiazolidin-2-yl}carbonyl)amino]propyl N-(tert-butoxycarbonyl)-L-valinate (3.04 g, 4.13 mmol) was dissolved in DCM (33 mL) at 0 degree and 66 mL of 4M HCl in dioxane was added. The reaction was stirred at 0 degree for 1 h and at r.t. for 3 h. The solvent was evaporated and the residue redissolved in DCM and washed with 10% $NaHCO_3$ and brine. The organic layer was dried over $MgSO_4$ and evaporated to give a white foam. The foam was redissolved in THF and 1 eq of methanesulfonic acid (345 mg) was added, the precipitate was filtered and dried to give the desired product (3S)-3-(2,6-difluorophenyl)-3-[({(2S)-3-[(2'-fluorobiphenyl-4-yl)sulfonyl]-1,3-thiazolidin-2-yl}carbonyl)amino]propyl L-valinate as a white solid (2.53 g, 83.7% yield).

$M^+(ESI^+)$: 636.7; $M^-(ESI^-)$: 634.3.

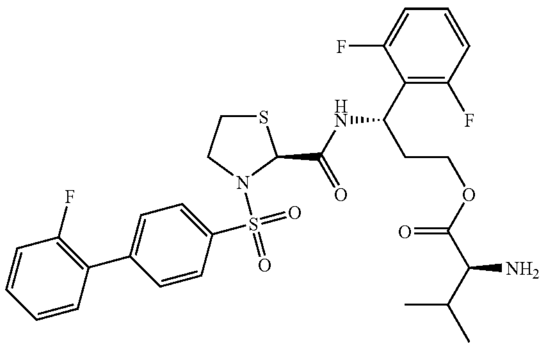 [SMILES: CC(C)[C@H](N)C(=O)OCC[C@H](NC(=O)[C@@H]1SCCN1S(=O)(=O)c1ccc(-c2ccccc2F)cc1)c1c(F)cccc1F]

Example 69

(3S)-3-({[(2S)-3-(biphenyl-4-ylsulfonyl)-1,3-thiazolidin-2-yl]carbonyl}-amino)-3-(2,6-difluorophenyl)propyl L-valinate Following the general strategies and protocols outlined in Example 68, starting from 3-(1,1'-biphenyl-4-ylsulfonyl)-N-[1-(2,6-difluorophenyl)-3-hydroxypropyl]-1,3-thiazolidine-2-carboxamide (Example 65), the title compound was obtained in 99% purity by HPLC.

$M^+(ESI^+)$: 618.9; $M^-(ESI^-)$: 616.5.

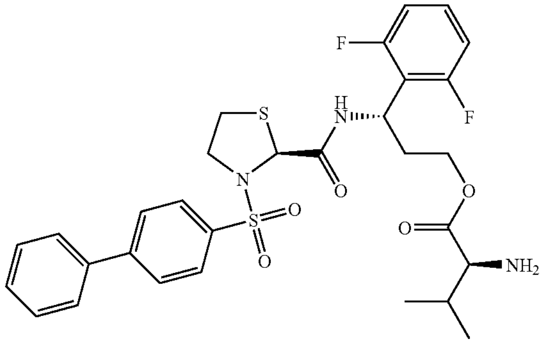 [SMILES: CC(C)[C@H](N)C(=O)OCC[C@H](NC(=O)[C@@H]1SCCN1S(=O)(=O)c1ccc(-c2ccccc2)cc1)c1c(F)cccc1F]

Example 70

(3S)-3-({[(2S)-3-(biphenyl-4-ylsulfonyl)-1,3-thiazolidin-2-yl]carbonyl}-amino)-3-phenylpropyl L-valinate Following the general strategies and protocols outlined in Example 68, starting from (2S)-3-([1,1'-biphenyl]-4-ylsulfonyl)-N-[(1S)-3-hydroxy-1-phenylpropyl]-1,3-thiazolidine-2-carboxamide (Example 1), the title compound was obtained in 99% purity by HPLC.

$M^+(ESI^+)$: 582.9; $M^-(ESI^-)$: 581.3.

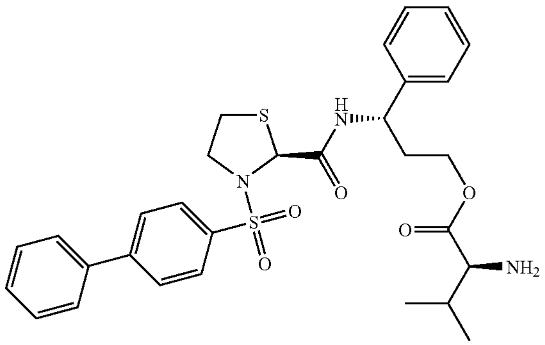 [SMILES: CC(C)[C@H](N)C(=O)OCC[C@H](NC(=O)[C@@H]1SCCN1S(=O)(=O)c1ccc(-c2ccccc2)cc1)c1ccccc1]

Example 71

(3S-3-[({(2S)-3-[(2'-fluorobiphenyl-4-yl)sulfonyl]-1,3-thiazolidin-2-yl}carbonyl)amino]-3-phenylpropyl L-valinate Following the general strategies and protocols outlined in Example 68, starting from (2S)-3-[(2'-fluoro-1,1'-biphenyl-4-yl)sulfonyl]-N-[(1S)-3-hydroxy-1-phenylpropyl]-1,3-thiazolidine-2-carboxamide (Example 67), the title compound was obtained in 99% purity by HPLC.

$M^+(ESI^+)$: 600.8; $M^-(ESI^-)$: 598.6.

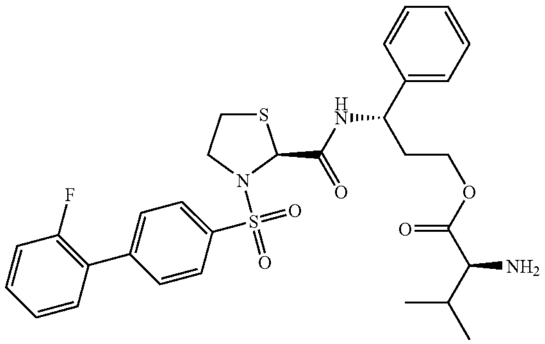 [SMILES: CC(C)[C@H](N)C(=O)OCC[C@H](NC(=O)[C@@H]1SCCN1S(=O)(=O)c1ccc(-c2ccccc2F)cc1)c1ccccc1]

Example 72

(2S)-3-(1,1'-biphenyl-4-ylsulfonyl)-N-[(1S)-3-hydroxy-1-(2,4-difluoro-phenyl)propyl]-1,3-thiazolidine-2-carboxamide Following the general strategies and protocols outlined in Example 1, starting tert-butyl (2S)-2-({[(1S)-1-(2,4-difluorophenyl)-3-hydroxypropyl]amino}carbonyl)-1,3-thiazolidine-3-carboxylate (Intermediate 6) and [1,1'-biphenyl]-4-sulfonyl chloride, the title compound was obtained in 98% purity by HPLC.

$M^+(ESI^+)$: 519.6; $M^-(ESI^-)$: 517.6.

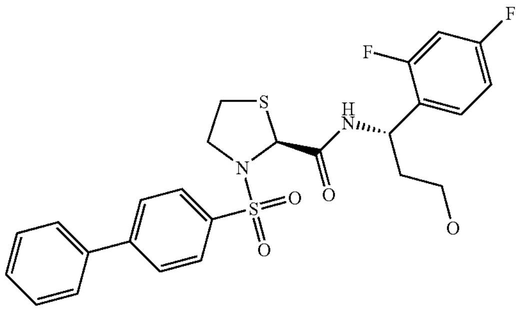 [SMILES: O=C(N[C@@H](CCO)c1ccc(F)cc1F)[C@@H]1SCCN1S(=O)(=O)c1ccc(-c2ccccc2)cc1]

Example 73

Preparation of a Pharmaceutical Formulation

Formulation 1—Tablets

A 1,3-thiazolidine-2-carboxamide compound of formula (II) is admixed as a dry powder with a dry gelatin binder in an approximate 1:2 weight ration. A minor amount of magnesium stearate is added as a lubricant. The mixture is formed into 240-270 mg tablets (80-90 mg of active 1,3-thiazolidine-2-carboxamide compound per tablet) in a tablet press.

Formulation 2—Capsules

A 1,3-thiazolidine-2-carboxamide compound of formula (II) is admixed as a dry powder with a starch diluent in an approximate 1:1 weight ratio. The mixture is filled into 250 mg capsules (125 mg of active 1,3-thiazolidine-2-carboxamide compound per capsule).

Formulation 3—Liquid

A 1,3-thiazolidine-2-carboxamide compound of formula (II), sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.

Formulation 4—Tablets

A 1,3-thiazolidine-2-carboxamide compound of formula (II) is admixed as a dry powder with a dry gelatin binder in an approximate 1:2 weight ratio. A minor amount of magnesium stearate is added as a lubricant. The mixture is formed into 450-900 mg tablets (150-300 mg of active 1,3-thiazolidine-2-carboxamide compound) in a tablet press.

Formulation 5—Injection

A 1,3-thiazolidine-2-carboxamide compound of formula (II) is dissolved in a buffered sterile saline injectable aqueous medium to provide a satisfactory concentration.

Example 51

Biological Assays

The compounds of formula (II), were be subjected to the following in vitro and in vivo biological assays:

1) In vitro competition binding assay on human Prostaglandin $F_{2\alpha}$ receptor using a Scintillating Proximity Assay (SPA)

This assay allows to determine the binding affinity of the test compounds of formula (I) for the human Prostaglandin $F_{2\alpha}$ receptor:

a) Preparation of Prostaglandin $F_{2\alpha}$ Receptor:

Human Prostaglandin $F_{2\alpha}$ receptor (full-length cDNA) was subcloned into the pCEP4 (Invitrogen) vector and transfected together with the hygromycin resistance gene into HEK 293 EBNA cells by Calcium-phosphate co-precipitation method. Antibiotic resistant cells were grown under constant selection pressure in DMEM/F-12 medium supplemented with 2% fetal calf serum, 4 mM L-Glutamine and 8 ml/l Insulin-Transferrin-Selenium-mix (all Invitrogen) and 300 μg/ml hygromycin at 37° C. in a humidified atmosphere of 5% $CO_2$ in air. At 48 h before harvesting, receptor expression was enhanced by adding 5 mM of Na-butyrate. Cells were washed twice with phosphate buffer saline, harvested and pelleted by centrifugation.

Cell pellet was lysed by Dounce homogenisation in 250 mM sucrose, 25 mM Tris-HCl pH 7.5, 10 mM $MgCl_2$, 1 mM EDTA containing proteases inhibitors according to the manufacturer (Boehringer Mannheim) at 4° C. The lysate was centrifuged at 1000 g, 4° C. for 10 min and the supernatant was centrifuged at 160000 g, 4° C. for 60 min. The membranes pellets were resuspended in binding buffer (10 mM MES pH 6.2, 10 mM $MgCl_2$, 1 mM EDTA containing proteases inhibitors), frozen in dry ice ethanol and stored at −80° C.

b) Determination of the Binding Affinity Values for Test Compounds:

In vitro competition binding with Scintillation proximity assay (SPA) was performed in Corning NBS 96 wells plates. Briefly, 100 μl of binding buffer containing 15 to 30 μg of purified membranes, 4 mg/ml of wheat-germ agglutinin (WGA) SPA beads and 1 to 2 nM of $^{3}H$ PGF2-alpha (determined by Scatchard analysis) in 1% DMSO was incubated for 2 hours at room temperature. Non-specific binding was determined in the presence of 1 μM of non-radioactive Prostaglandin $F_{2\alpha}$. The concentrations of compounds (antagonist) used to compete with the radioactive ligand (agonist) were 10 μM, 3 μM, 1 μM, 300 nM, 100 nM, 30 nM, 10 nM, 1 nM, 100 pM, 10 pM. The radioactivity was counted on a Microbeta plate counter and the binding data were analysed using the iterative, non-linear, curve-fitting program, "Prism" (GraphPad Software, Inc).

c) Results—Discussion:

The tested compounds according to formula (II) induced an inhibition (illustrated by $K_i$ values) of the binding of Prostaglandin $F_{2\alpha}$ to its receptor of less than 10 μM. The binding affinity of preferred compounds of formula (II) to human Prostaglandin $F_{2\alpha}$ receptor is illustrated in the below Table 1 by means of the corresponding inhibition constants $K_i$. From the values shown in Table 1, it can be concluded that said test compounds according to formula (II) do show a significant binding to the Prostaglandin $F_{2\alpha}$ receptor.

TABLE 1

Binding affinities of test compounds of general formula (II) to human Prostaglandin $F_{2\alpha}$ receptor, as determined in the scintillation proximity competition binding assay (against Prostaglandin $F_{2\alpha}$ as radioligand).

| Structure | IUPAC Name | Binding affinity for human Prostaglandin $F_{2\alpha}$ receptor $K_i$ (μM) |
|---|---|---|
| 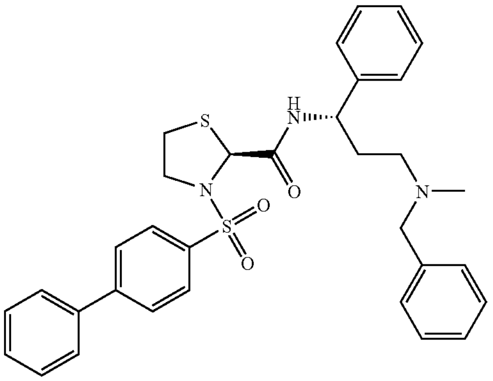 [SMILES: CN(CC[C@H](NC(=O)[C@@H]1SCCN1S(=O)(=O)c1ccc(-c2ccccc2)cc1)c1ccccc1)Cc1ccccc1] | (2S)-N-{(1S)-3-[benzyl(methyl)amino]-1-phenyl]propyl}-3-([1,1'-biphenyl]-4-ylsulfonyl)-1,3-thiazolidine-2-carboxamide | 0.020 |
| 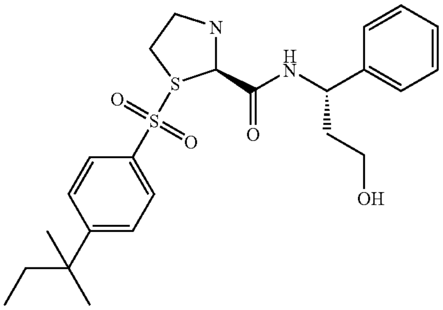 | (2S)-N-[(1S)-3-hydroxy-1-phenylpropyl]-3-[(4-tert-pentylphenyl)sulfonyl]-1,3-thiazolidine-2-carboxamide | 0.120 |
| 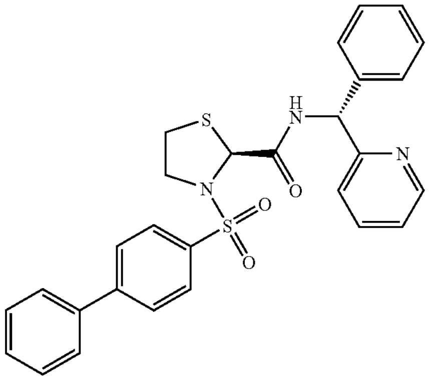 [SMILES: O=C(N[C@H](c1ccccc1)c1ccccn1)[C@@H]1SCCN1S(=O)(=O)c1ccc(-c2ccccc2)cc1] | (2S)-3-([1,1'-biphenyl]-4-ylsulfonyl)-N-[(R)-phenyl(2-pyridinyl)methyl]-1,3-thiazolidine-2-carboxamide | 0.055 |
| 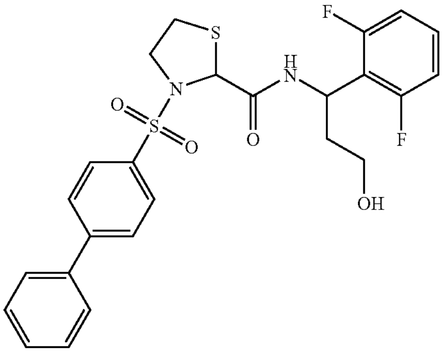 [SMILES: O=C(NC(CCO)c1c(F)cccc1F)C1SCCN1S(=O)(=O)c1ccc(-c2ccccc2)cc1] | 3-([1,1'-biphenyl]-4-ylsulfonyl)-N-[1-(2,6-difluorophenyl)-3-hydroxypropyl]-1,3-thiazolidine-2-carboxamide | 0.050 |

TABLE 1-continued

Binding affinities of test compounds of general formula (II) to human Prostaglandin $F_{2\alpha}$ receptor, as determined in the scintillation proximity competition binding assay (against Prostaglandin $F_{2\alpha}$ as radioligand).

| Structure | IUPAC Name | Binding affinity for human Prostaglandin $F_{2\alpha}$ receptor $K_i$ (μM) |
|---|---|---|
| 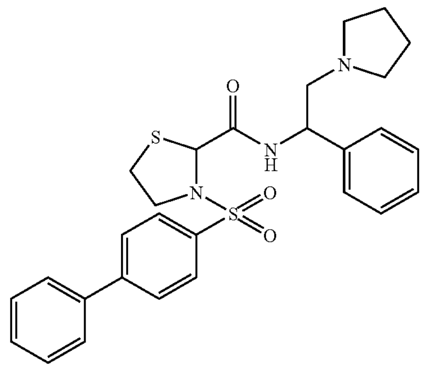 [SMILES: O=C(NC(CN1CCCC1)c1ccccc1)C1SCCN1S(=O)(=O)c1ccc(-c2ccccc2)cc1] | 3-([1,1'-biphenyl]-4-ylsulfonyl)-N-[1-phenyl-2-(1-pyrrolidinyl)ethyl]-1,3-thiazolidine-2-carboxamide | 0.170 |
| 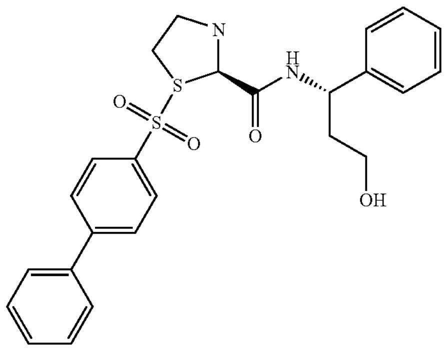 | (2S)-3-([1,1'-biphenyl]-4-ylsulfonyl)-N-[(1S)-3-hydroxy-1-phenylpropyl]-1,3-thiazolidine-2-carboxamide | 0.065 |
| 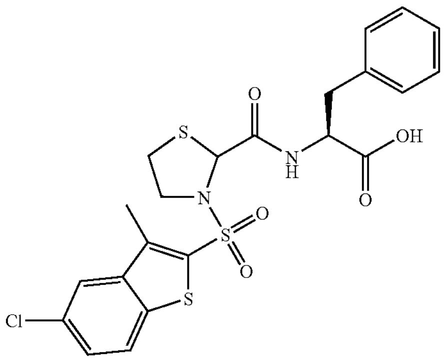 [SMILES: Cc1c(S(=O)(=O)N2CCSC2C(=O)N[C@@H](Cc2ccccc2)C(=O)O)sc2ccc(Cl)cc12] | (2S)-2-[({3-[(5-chloro-3-methyl-1-benzothien-2-yl)sulfonyl]-1,3-thiazolidine-2-yl}carbonyl)amino]-3-phenylpropanoic acid | 0.330 |
| 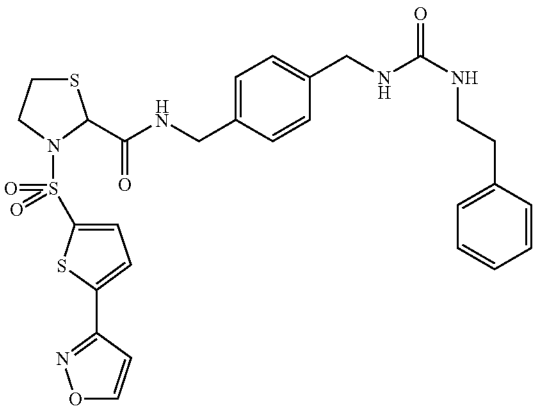 [SMILES: O=C(NCCc1ccccc1)NCc1ccc(CNC(=O)C2SCCN2S(=O)(=O)c2ccc(-c3ccon3)s2)cc1] | 3-{[5-(3-isoxazolyl)-2-thienyl]sulfonyl}-N-{4-[({[(2-phenylethyl)amino]carbonyl}amino)methyl]benzyl}-1,3-thiazolidine-2-carboxamide | 1.10 |

TABLE 1-continued

Binding affinities of test compounds of general formula (II) to human Prostaglandin $F_{2\alpha}$ receptor, as determined in the scintillation proximity competition binding assay (against Prostaglandin $F_{2\alpha}$ as radioligand).

| Structure | IUPAC Name | Binding affinity for human Prostaglandin $F_{2\alpha}$ receptor $K_i$ (μM) |
|---|---|---|
| 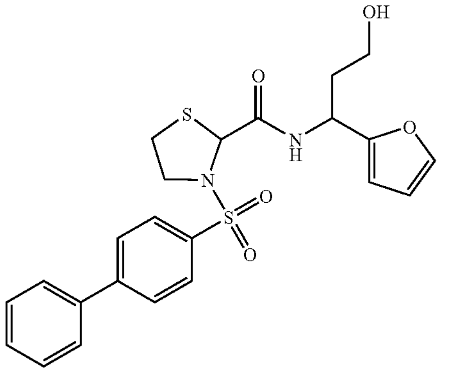 [SMILES: O=C(NC(CCO)c1ccco1)C1SCCN1S(=O)(=O)c1ccc(-c2ccccc2)cc1] | 3-([1,1'-biphenyl]-4-ylsulfonyl)-N-[1-(2-furyl)-3-hydroxypropyl]-1,3-thiazolidine-2-carboxamide | 0.620 |
| 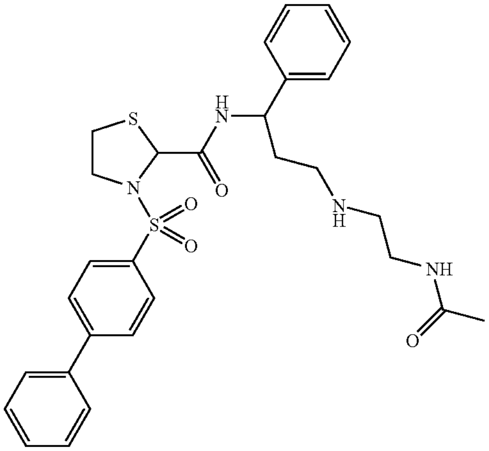 [SMILES: CC(=O)NCCNCCC(NC(=O)C1SCCN1S(=O)(=O)c1ccc(-c2ccccc2)cc1)c1ccccc1] | N-(3-{[2-(acetylamino)ethyl]amino}-1-phenylpropyl)-3-([1,1'-biphenyl]-4-ylsulfonyl)-1,3-thiazolidine-2-carboxamide | 1.15 |

2) In vitro functional assay 1: Inhibition of Prostaglandin $F_{2\alpha}$ induced IP3 (Inositol Triphosphate) Synthesis in HEK/EBNA-cells expressing the Prostaglandin $F_{2\alpha}$ receptor The interaction of Prostaglandin $F_{2\alpha}$ with its receptor leads to IP3 synthesis, a second messenger for $Ca^{2+}$ release from sarcoplasmatic reticulum, involved in the process triggering uterine contractions. The present assay described hereinafter can be used to show the inhibition of the Prostaglandin $F_{2\alpha}$/Prostaglandin $F_{2\alpha}$ receptor mediated IP3 synthesis by test compounds of formula (II).

a) Materials:

293-EBNA cells and pCEP4 vector were purchased from Invitrogen; Fetal Bovine Serum from Cansera; Hygromycin B from Roche Molecular Biochemicals; DMEM-F12 medium, L-Glutamine from Life Technologies Inc.; [$^3$H] Inositol from Perkin Elmer Life Sciences; Prostaglandin $F_{2\alpha}$ ($PGF_{2\alpha}$) from Sigma, AG1-X8 chromatography columns from BioRad, 96 well black/white plates from Corning Inc.

b) Constructs:

The cDNAs of the human Prostaglandin $F_{2\alpha}$ receptor (hFP) and of the rat Prostaglandin $F_{2\alpha}$, receptor (rFP) receptors were subcloned into the expression vector pCEP4 to generate pCEP4hFPuno and pCEP4rFP respectively.

c) Cell culture and transfection:

293-EBNA cells were grown in DMEM-F12 medium supplemented with 2% fetal bovine serum and 4 mM L-glutamine. Cells were transfected by the calcium phosphate precipitation method with the appropriate plasmid and selected for hygromycinB resistance. The surviving colonies were assayed for their ability to retain specific [$^3$H] $PGF_{2\alpha}$ binding. Selected clones were maintained in DMEM-F12 medium supplemented with 4 mM L-glutamine, 300 μg/ml hygromycinB and 2% fetal bovine serum (10% for cells expressing rFP).

d) Inositol Phosphate Measurements:

Cells were detached with PBS/EDTA, washed with inositol-free DMEM-F12 medium and seeded at 80000 cells/well in a Poly-L-Lysine precoated 12 well plate. Cells were labelled with myo-[$^3$H] Inositol at 4 μCi/ml in inositol-free DMEM-F12 supplemented with 1% fetal bovine serum, 4 mM L-glutamine and 300 μg/ml hygromycinB. After 24 hours (rFP expressing cells) or 40 hours (hFP expressing cells), the medium was removed and cells were pre-incubated for 10 min in assay buffer (DMEM-F12 without Inositol, 20 mM Hepes, 0.1% BSA) containing 20 mM LiCl at 37° C. For agonist dose response, cells were then stimulated for 1 hour at room temperature with increasing concentration of $PGF_{2\alpha}$, in assay buffer. For $IC_{50}$ determination of the compounds, cells were incubated with increasing concentrations of test compounds for 10 min at room temperature prior to addition of 30 nM $PGF_{2\alpha}$ (about 2× the $EC_{50}$) and further incubation for 1 hour. For agonist activity determination of the test compounds themselves, the test compounds were added to the cells at 10 μM and 1 μM for 1 hour at room temperature.

In the course of the three above mentioned experiments, the reaction was stopped by addition of 1 ml of stop solution (2.4% perchloric acid) for 10 min. 800 μl were then transferred to 400 μl of neutralizing solution (0.72N KOH, 0.6 M $KHCO_3$), vortexed, and sedimented for at least 2 hours at 4° C. After centrifugation of 15 min. at 2500 g, 1 ml of the supernatant was loaded on a chromatography column, followed by two washes with 10 ml of water. The IP3 to be quantified were eluted with 3 ml elution buffer (1M ammonium formate, 0.1 M formic acid) and radioactivity was counted on a Beckman LS6000TA scintillation counter to measure the amount of phosphorylated [$^3$H] inositol.

e) Results and Discussion:

The activities of the thiazolidine compounds of formula (II) were assessed using the above described in vitro biological assay. Representative values for some example compounds are given in Table 2 below. The values refer to the capacity of the example compounds according to formula (II) to effectively antagonize Prostaglandin $F_{2\alpha}$-induced IP3-synthesis mediated by the Prostaglandin $F_{2\alpha}$ receptor. From the values shown in Table 2, it can be derived that said example test compounds according to formula (II) do exhibit a significant activity as Prostaglandin $F_{2\alpha}$ receptor antagonists, as illustrated by $IC_{50}$ values of generally less than 2 μM.

TABLE 2

Inhibition of IP3 synthesis in HEK EBNA cells expressing the human Prostaglandin $F_{2\alpha}$ receptor, by thiazolidine antagonists of general formula (II).

| Structure | IUPAC-Name | Inhibition of Prostaglandin $F_{2\alpha}$-induced IP3-synthesis, $IC_{50}$ (μM) |
|---|---|---|
| 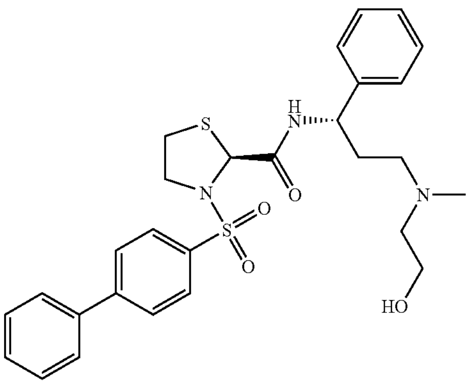 [SMILES: CN(CCO)CC[C@H](NC(=O)[C@@H]1SCCN1S(=O)(=O)c1ccc(-c2ccccc2)cc1)c1ccccc1] | (2S)-3-([1,1'-biphenyl]-4-ylsulfonyl)-N-{(1S)-3-[(2-hydroxyethyl)(methyl)amino]-1-phenylpropyl}-1,3-thiazolidine-2-carboxamide | 0.225 |
| 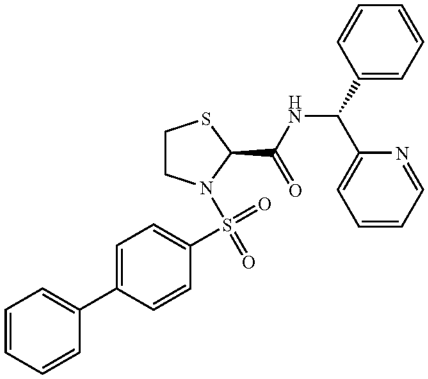 [SMILES: O=C(N[C@H](c1ccccc1)c1ccccn1)[C@@H]1SCCN1S(=O)(=O)c1ccc(-c2ccccc2)cc1] | (2S)-3-([1,1'-biphenyl]-4-ylsulfonyl)-N-[(R)-phenyl(2-pyridinyl)methyl]-1,3-thiazolidine-2-carboxamide | 0.015 |
| 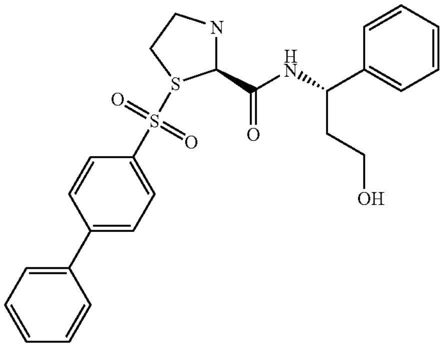 | (2S)-3-([1,1'-biphenyl]-4-ylsulfonyl)-N-[(1S)-3-hydroxy-1-phenylpropyl]-1,3-thiazolidine-2-carboxamide | 0.185 |

3) In vitro functional assay 2: Inhibition of Prostaglandin $F_{2\alpha}$ induced $Ca^{2+}$-mobilization in HEK/EBNA-cells expressing the Prostaglandin $F_{2\alpha}$ receptor, as measured by FLIPR® (Fluorimetric Imaging Plate Reader).

a) Calcium Mobilization Measurements by FLIPR (Fluorometric Imaging Plate Reader)

HEK EBNA cells were seeded at 60000 cells/well in a Poly-L-Lysine precoated black/white bottom 96 well plate. 24 hours later cells were loaded with 4.5 nM Fluo-4 in DMEM-F12 without fetal calf serum for 1-2 hours at 37° C. For Prostaglandin $F_{2\alpha}$ dose response or agonist activity measurement of compounds—after a wash with FLIPR buffer (10 mM Hepes, 145 mM NaCl, 5 mM KCl, 1 mM $MgCl_2$, 10 mM glucose, pH 7.4)—cells were stimulated with increasing concentration of Prostaglandin $F_{2\alpha}$ or test compounds of formula (II). Calcium mobilization was then measured on the FLIPR for 4 min. For $IC_{50}$ determination of the molecules, increasing concentrations of test compounds were added to the cells 30 min prior to the wash step. After the wash with FLIPR buffer, increasing concentrations of test compounds were added to the cells in FLIPR buffer and calcium mobilization was measured for 1 min. Then the cells were stimulated with a concentration of 2 times the $EC_{50}$ of Prostaglandin $F_{2\alpha}$ and calcium mobilization was measured for 4 min.

b) Results and Discussion:

The activities of the thiazolidine derivatives according to formula (II) were assessed using the above described in vitro biological assay. Representative values for some example compounds are given in Table 3 below. The values refer to the capacity of the example compounds according to formula (II) to effectively antagonize Prostaglandin $F_{2\alpha}$-induced intracellular $Ca^{2+}$-mobilization mediated by the Prostaglandin $F_{2\alpha}$-receptor. From the $IC_{50}$-values shown in Table 3 it can be derived that said example test compounds according to formula (II) do exhibit a significant activity as Prostaglandin $F_{2\alpha}$ receptor antagonists, as illustrated by $IC_{50}$ values of generally less than 2 μM.

TABLE 3

Inhibition of $Ca^{2+}$-mobilization in HEK EBNA cells expressing the human Prostaglandin $F_{2\alpha}$ receptor, by thiazolidine antagonists of general formula (II).

| Structure | IUPAC Name | Inhibition of Prostaglandin $F_{2\alpha}$ induced $Ca^{2+}$-mobilization, $IC_{50}$ (μM) |
|---|---|---|
| 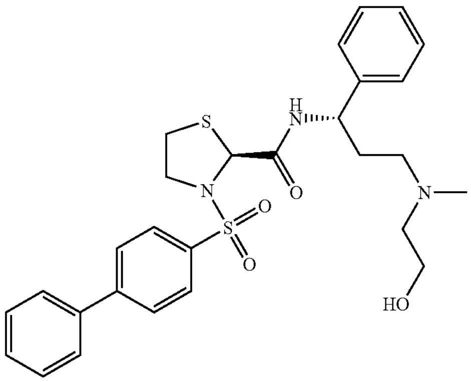 [SMILES: CN(CCO)CC[C@H](NC(=O)[C@@H]1SCCN1S(=O)(=O)c1ccc(-c2ccccc2)cc1)c1ccccc1] | (2S)-3-([1,1'-biphenyl]-4-ylsulfonyl)-N-{(1S)-3-[(2-hydroxyethyl)(methyl)amino]-1-phenylpropyl}-1,3-thiazolidine-2-carboxamide | 0.202 |
| 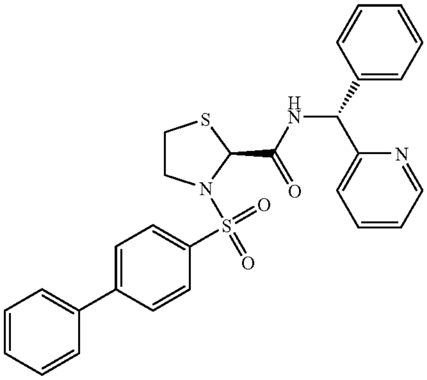 [SMILES: O=C(N[C@H](c1ccccc1)c1ccccn1)[C@@H]1SCCN1S(=O)(=O)c1ccc(-c2ccccc2)cc1] | (2S)-3-([1,1'-biphenyl]-4-ylsulfonyl)-N-[(R)-phenyl(2-pyridinyl)methyl]-1,3-thiazolidine-2-carboxamide | 0.020 |

TABLE 3-continued

Inhibition of $Ca^{2+}$-mobilization in HEK EBNA cells expressing the human Prostaglandin $F_{2\alpha}$ receptor, by thiazolidine antagonists of general formula (II).

| Structure | IUPAC Name | Inhibition of Prostaglandin $F_{2\alpha}$ induced $Ca^{2+}$-mobilization, $IC_{50}$ (μM) |
|---|---|---|
| 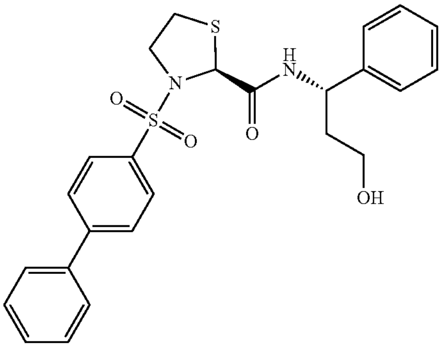 [SMILES: O=C(N[C@@H](CCO)c1ccccc1)[C@@H]1SCCN1S(=O)(=O)c1ccc(-c2ccccc2)cc1] | (2S)-3-([1,1'-biphenyl]-4-ylsulfonyl)-N-[(1S)-3-hydroxy-1-phenylpropyl]-1,3-thiazolidine-2-carboxamide | 0.048 |

4) In vivo assay: Reduction of uterine contractile activity in rats a) $PGF_{2\alpha}$ or fluprostenol-induced uterine contractions in non-pregnant rats (i) Preparation of the Experiment:

Non-pregnant Sprague Dawley female rats (Charles River, Calco, Italy) weighing 200-300 g were used. They received an i.p. injection of 250 μg/kg diethylstilbestrol (DES) 18 and 24 hours before the experiment. On the day of the experiment, they were anaesthetized with urethane (1.05 g/kg, i.p.) and placed on a homeothermic operating table. The trachea was then isolated and cannulated with a suitable polyethylene (PE) tubing. A midline incision at the hypogastrium level was made, one uterine horn exposed and its tubal end closed (near the ovary) by a ligature with surgical silk. About 3 cm posteriorly to the first tie, the uterine horn wall was incited (close to the uterus body) and a PE240 tubing was inserted into the lumen and secured with surgical silk. After filling the internal cavity with 0.2 ml of sterile physiological saline solution, the catheter was connected to an amplifying/recording system (MacLab, ADInstruments Pty Ltd, Castle Hill, Australia) via a P23ID Gould Statham pressure transducer. One jugular vein was then isolated and cannulated with a PE60 catheter connected to a butterfly needle for the intravenous administration of Prostaglandin $F_{2\alpha}$ (Sigma Chem. co., St. Louis, Mo., USA) and (±)fluprostenol (Cayman Chemicals, Ann Arbor, Mich., USA) or test compounds. For the oral administration, the esophagus was cannulated with a PE90 catheter.

For obtaining information regarding the test compound plasma levels, 2, 30, 90 and 210 minutes after the intravenous administration or 30, 60, 120 and 210 minutes after the oral administration, 0.5-ml blood samples were withdrawn from the carotid artery previously cannulated with a PE60 catheter. Plasma was then obtained by standard laboratory procedure and the resulting samples were stored at −20° C. for successive determinations.

After a suitable stabilization period, repeated administrations of Prostaglandin $F_{2\alpha}$ (by a 10-min intravenous infusion) or fluprostenol (by intravenous bolus) were performed every 35 minutes for 9 times totally. The contractile response obtained from the third Prostaglandin $F_{2\alpha}$ or fluprostenol injection was set as 100%. Five minutes before the fourth injection of Prostaglandin $F_{2\alpha}$ and (±) fluprostenol, the test compound of formula (II) (i.e. a FP antagonist) was injected intravenously as a 5-min infusion.

(ii) Results and Discussion:

As each administration of Prostaglandin $F_{2\alpha}$ or fluprostenol induced a train of uterine contractions, the resulting contractile response was quantified by measuring the area under the curve (AUC) of the changes in intraluminal uterine pressure (by Chart V4.04 for Windows software, PowerLab ADInstruments, Castle Hill, Australia) over the first 15 minutes of the 35-min post-injection period (Prostaglandin $F_{2\alpha}$-induced uterine contractions) or the whole 35-min (for fluprostenol). Percent variations of AUCs determined after each Prostaglandin $F_{2\alpha}$ or fluprostenol injection were calculated in comparison to the AUC obtained with the third injection (set as 100%) of Prostaglandin $F_{2\alpha}$ or fluprostenol. The effect of the test compound was expressed at each time-point as the percent inhibition of the above variation values after the administration of each dose of test compound compared to that obtained at the corresponding time-point in the group receiving the vehicle alone. From the inhibition values obtained for each dose-group at the peak effect, a dose-response curve was plotted and, when possible, the relative $ED_{50}$ value calculated (by S-Plus 2000 v.4.6 statistical software, Mathsoft, Inc. Seattle, Wash., USA).

Compound (2S)-3-[(1,1'-biphenyl-4-ylsulfonyl)-N-[(1S)-3-hydroxy-1-phenylpropyl]-1,3-thiazolidine-2-carboxamide for instance for instance, 40 minutes after administration by i.v. route, caused inhibition of uterine contractions of 26%, at a cumulative dose of 30 mg/kg.

b) Spontaneous Uterine Contractions in Late-Term Pregnant Rats:

(i) Preparation of the Experiment:

Late-term pregnant (19-21 days of gestation) Sprague Dawley female rats (Charles River, Calco, Italy) weighing 350-400 g were anesthetized with urethane (1.05 g/kg, i.p.) and placed on a homeothermic operating table. The trachea was isolated and cannulated with a suitable polyethylene (PE) tubing. A midline incision at the hypogastrium level was made, one pregnant uterine horn exposed and its tubal end closed (near the ovary) by a ligature with surgical silk. In the correspondence of the last foetus near the above-mentioned ovary, the uterine horn wall was incited taking care not to injure the adjacent placenta, and a PE240 tubing with a latex balloon (9 mm length when empty, capacity 0.1 ml; Radnoti, Monrovia, Calif., USA) on the top was inserted into the lumen and secured with surgical silk. After filling the internal cavity of the latex balloon with 0.1 ml of sterile physiological saline solution, the catheter was connected to an amplifying/recording system (MacLab, ADInstruments Pty Ltd, Castle Hill, Australia) via a P23ID Gould Statham pressure transducer. One jugular vein was then isolated and cannulated with a PE60 catheter connected to a butterfly needle for the intravenous administration of the vehicle or test compounds.

After a suitable stabilization period, vehicle or increasing doses of the test compound were administered by a 10-min intravenous infusion. Each dose administration was followed by a 30-min recovery period.

(ii) Results and Discussion:

The spontaneous contractile response of the uterus was quantified by evaluating the area under the curve (AUC) of the changes in the intra-luminal uterine pressure over time (by Chart V4.04 for Windows software, PowerLab ADInstruments, Castle Hill, Australia). The effect of the test compound on the spontaneous uterine contraction was evaluated as the percent variation of the AUC calculated in a 10-min interval following the administration of each dose of test compound as compared to the AUC in a 10-min interval before the administration of the first dose of test compound (basal value). When possible, a dose-response curve (of peak effect) was plotted and the relative ED50 value calculated (by S-Plus 2000 v. 4.6 statistical software, Mathsoft, Inc. Seattle, Wash., USA).

Compound (2S)-3-[(1,1'-biphenyl-4-ylsulfonyl)-N-[(1S)-3-hydroxy-1-phenylpropyl]-1,3-thiazolidine-2-carboxamide for instance, upon administration by i.v. route (infusion over 10 minutes), caused inhibition of uterine contractions of >50%, at a cumulative dose of 30 mg/kg—with a calculated $ED_{50}$ value) of 28 mg/kg or 2.8 mg/kg/min, in the experiment outlined above.

What we claim is:

1. A compound, geometrical isomers of said compound, optically active forms of said compound, enantiomers of said compound, diastereomers of said compound, racemate forms of said compound, or pharmaceutically acceptable salts of said compound wherein said compound is represented by formula I,

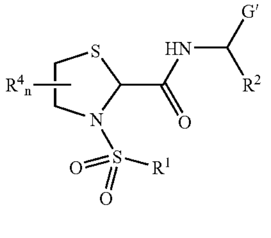

I

G' is selected from the group consisting of aryl, heteroaryl, $C_3$-$C_8$-cycloalkyl, 3 to 8 membered heterocycloalkyl, substituted aryl, substituted heteroaryl, substituted $C_3$-$C_8$-cycloalkyl and substituted 3 to 8 membered heterocycloalkyl, wherein said cycloalkyl or aryl or heteroaryl groups are optionally fused with cycloalkyl or aryl or heteroaryl groups;

$R^1$ is biphenyl or tert-butyl phenyl;

$R^2$ is selected from the group consisting of H, carboxy, acyl, alkoxycarbonyl, $C_1$-$C_5$-alkyl carboxy, $C_1$-$C_5$-alkyl acyl, $C_1$-$C_5$-alkyl alkoxycarbonyl, $C_1$-$C_5$-alkyl acyloxy, $C_1$-$C_5$-alkyl sulfanyl, $C_1$-$C_5$-alkyl sulfinyl, $C_1$-$C_5$-alkyl sulfonyl, $C_1$-$C_5$-alkyl sulfonyloxy, $C_1$-$C_6$-alkyl, $C_2$-$C_6$-alkenyl, $C_2$-$C_6$-alkynyl, aryl, heteroaryl, $C_3$-$C_8$-cycloalkyl, $C_1$-$C_6$-alkyl aryl, $C_2$-$C_6$-alkyl heteroaryl, $C_1$-$C_6$-alkyl cycloalkyl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, substituted carboxy, substituted acyl, substituted alkoxycarbonyl, substituted $C_1$-$C_5$-alkyl carboxy, substituted $C_1$-$C_5$-alkyl acyl, substituted $C_1$-$C_5$-alkyl alkoxycarbonyl, substituted $C_1$-$C_5$-alkyl acyloxy, substituted $C_1$-$C_5$-alkyl sulfanyl, substituted $C_1$-$C_5$-alkyl sulfinyl, substituted $C_1$-$C_5$-alkyl sulfonyl, substituted $C_1$-$C_5$-alkyl sulfonyloxy, substituted $C_1$-$C_6$-alkyl, substituted $C_2$-$C_6$-alkenyl, substituted $C_2$-$C_6$-alkynyl, substituted aryl, substituted heteroaryl, substituted $C_3$-$C_8$-cycloalkyl, substituted $C_1$-$C_6$-alkyl aryl, substituted $C_2$-$C_6$-alkyl heteroaryl, substituted $C_1$-$C_6$-alkyl cycloalkyl, substituted $C_2$-$C_6$-alkenyl aryl, substituted $C_2$-$C_6$-alkenyl heteroaryl, substituted $C_2$-$C_6$-alkynyl aryl, and substituted $C_2$-$C_6$-alkynyl heteroaryl;

$R^4$ is selected from the group consisting of $C_1$-$C_6$-alkyl, $C_2$-$C_6$-alkenyl, $C_2$-$C_6$-alkynyl, substituted $C_1$-$C_6$-alkyl, substituted $C_2$-$C_6$-alkenyl, and substituted $C_2$-$C_6$-alkynyl; and n is an integer from 0 to 2, wherein when G', $R^1$, $R^2$, or $R^4$ represent a substituted group 1 to 5 substituents may be present, which are selected from the group consisting of $C_1$-$C_6$-alkyl, $C_2$-$C_6$-alkenyl, $C_2$-$C_6$-alkynyl, cyclo-alkyl, $C_1$-$C_6$-alkyl aryl, $C_1$-$C_6$-alkyl heteroaryl, $C_1$-$C_6$-alkyl cycloalkyl, $C_1$-$C_6$-alkyl heterocycloalkyl, acyl, acyloxy, alkoxycarbonyl, aryl, heteroaryl, sulfinyl, sulfonyl, alkoxy, sulfanyl, halogen, carboxy, trihalomethyl, cyano, hydroxy, mercapto, and nitro, alternatively the substitution could also comprise ring closure of neighbouring substituents;

wherein said sulfonyl is of the formula —$SO_2$—X wherein X is selected from the group consisting of hydrogen, aryl, heteroaryl, $C_1$-$C_6$-alkyl, halogen-substituted $C_1$-$C_6$-alkyl, $C_1$-$C_6$-alkyl aryl, and $C_1$-$C_6$-alkyl heteroaryl;

said sulfinyl is of the formula —S(O)—Y wherein Y is selected from the group consisting of hydrogen, aryl, heteroaryl, $C_1$-$C_6$-alkyl, halogen-substituted $C_1$-$C_6$-alkyl, $C_1$-$C_6$-alkyl aryl, and $C_1$-$C_6$-alkyl heteroaryl; and said sulfanyl is of the formula —S—Z wherein Z is selected from the group consisting of $C_1$-$C_6$-alkyl, aryl, hetero-aryl, $C_1$-$C_6$-alkyl aryl, and $C_1$-$C_6$-alkyl heteroaryl.

2. A pharmaceutical composition comprising at least one compound according to claim 1 and a pharmaceutically acceptable carrier, diluent or excipient thereof.

3. A method of preparing the compound of formula (I) according to claim 1, comprising:

deprotecting a first compound represented by formula V in the presence of a base and a second compound represented by formula VI to obtain the compound represented by formula I

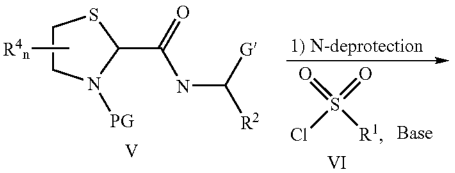

V VI

-continued

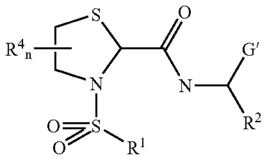

I wherein PG is a protecting group selected from Boc, Fmoc and Cbz.

4. A method of preparing the compound represented by formula I according to claim 1, comprising:

peptide coupling a first compound represented by formula VIII with a second compound represented by formula IV to obtain the compound represented by formula I.

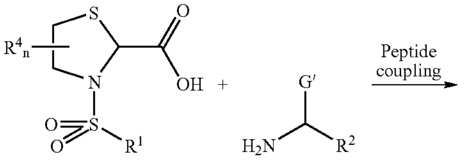

VIII IV

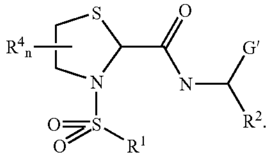

I

5. A compound, geometrical isomers of said compound, optically active forms of said compound, enantiomers of said compound, diastereomers of said compound, racemate forms of said compound, or pharmaceutically acceptable salts of said compound selected from the group consisting of:

3-[(4-tert-butylphenyl)sulfonyl]-N-(3-hydroxy-1-phenylpropyl)-1,3-thiazolidine-2-carboxamide;

(2S)-3-[(4-tert-butylphenyl)sulfonyl]-N-[(1S)-3-hydroxy-1-phenylpropyl]-1,3-thiazolidine-2-carboxamide;

(2R)-3-[(4-tert-butylphenyl)sulfonyl]-N-[(1S)-3-hydroxy-1-phenylpropyl]-1,3-thiazolidine-2-carboxamide;

3-[(4-tert-butylphenyl)sulfonyl]-N-(1-phenylethyl)-1,3-thiazolidine-2-carboxamide;

N-(3-aminobenzyl)-3-[(4-tert-butylphenyl)sulfonyl]-1,3-thiazolidine-2-carboxamide; and N-(4-aminobenzyl)-3-[(4-tert-butylphenyl)sulfonyl]-1,3-thiazolidine-2-carboxamide.

6. The compound of claim 1, wherein n is 0.

7. The compound of claim 1, wherein $R^2$ is a $C_1$-$C_3$ alkyl substituted with hydroxyl.

8. The compound according to claim 1, wherein $R^2$ is a pyridine.

9. The compound according to claim 1, wherein G' is an optionally substituted aryl or heteroaryl group.

10. The compound according to claim 1, wherein G' is a cycicoalkyl or aryl group fused with a heteroaryl group.

11. The compound according to claim , wherein $R^2$ is H.

* * * * *